US011976064B2

(12) United States Patent
Ahmad et al.

(10) Patent No.: US 11,976,064 B2
(45) Date of Patent: *May 7, 2024

(54) TOLL-LIKE RECEPTOR AGONISTS

(71) Applicant: Pfizer Inc., New York, NY (US)

(72) Inventors: Omar Ahmad, Cambridge, MA (US); Andrew Fensome, Harvard, MA (US); Erik Alphie LaChapelle, Uncasville, CT (US); Ethan Lawrence Fisher, Chester, CT (US); Rayomand J. Unwalla, Bedford, MA (US); Jun Xiao, East Lyme, CT (US); Lei Zhang, Auburndale, MA (US)

(73) Assignee: Pfizer Inc., New York, NY (US)

( * ) Notice: Subject to any disclaimer, the term of this patent is extended or adjusted under 35 U.S.C. 154(b) by 82 days.

This patent is subject to a terminal disclaimer.

(21) Appl. No.: 17/738,074

(22) Filed: May 6, 2022

(65) Prior Publication Data

US 2022/0274986 A1 Sep. 1, 2022

Related U.S. Application Data

(63) Continuation of application No. 16/926,933, filed on Jul. 13, 2020, now Pat. No. 11,339,159.

(60) Provisional application No. 62/875,465, filed on Jul. 17, 2019, provisional application No. 62/961,288, filed on Jan. 15, 2020.

(51) Int. Cl.
*A61K 31/4745* (2006.01)
*A61K 31/437* (2006.01)
*C07D 471/04* (2006.01)

(52) U.S. Cl.
CPC .......... *C07D 471/04* (2013.01); *A61K 31/437* (2013.01)

(58) Field of Classification Search
CPC .... A61K 31/437; A61K 31/4745; A61P 35/00
USPC ........................................ 514/303
See application file for complete search history.

(56) References Cited

U.S. PATENT DOCUMENTS 11,339,159 B2 * 5/2022 Ahmad ................... A61P 35/00

FOREIGN PATENT DOCUMENTS

| CN | 108794467 A | 11/2018 |
|----|-------------|---------|
| RU | 2412942 C2 | 2/2011 |
| RU | 2475487 C2 | 2/2013 |
| WO | 1995/02597 | 1/1995 |
| WO | 2005/032484 A2 | 4/2005 |
| WO | 2006/009832 | 1/2006 |
| WO | 2008/135791 A1 | 11/2008 |
| WO | 2015/162075 | 10/2015 |
| WO | 2016/091698 | 6/2016 |
| WO | 2017/102652 | 6/2017 |
| WO | 2017/184735 A1 | 10/2017 |
| WO | 2018/196823 A1 | 11/2018 |

OTHER PUBLICATIONS

Vittori et al., "Antiviral Properties of Deazaadenine Nucleoside Derivatives", Current Medicinal Chemistry, vol. 13 (29) pp. 3529-3552 (2006).
Houston et al., "Potential Inhibitors of S-Adenosylmethionine-Dependent Methyltransfereases. 9.2',3'-Dialdehyde Derivatives of Carbocyclic Purine Nucleosides as Inhibitors of S-Adenosylhomocysteine Hydrolase", J. Med. Chem., vol. 28(4), pp. 471-477 (1985).
Houston et al., "Potential Inhibitors of S-Adenosylmethionine-Dependent Methyltransferases. 8. Molecular Dissections of Carbocyclic 3-Deazaadenosine as Inhibitors of S-Adenosylhomocystein Hydrolase", J. Med. Chem., vol. 28(4), pp. 467-471 (1985).
Gorden et al., "Synthetic TLR agonists reveal functional differences between human TLR7 and TLRB", The Journal of Immunology, American Association of Immunologists, US, vol. 174, No. 3, Feb. 1, 2005 (Feb. 1, 2005), pp. 1259-1268; XP009163641, ISSN: 0022-1767, DOI: 10.4049/JIMMUNOL.174.3.1259.
International Search Report and Written Opinion of the International Searching Authority for International Application No. PCT/IB2020/056605, dated Sep. 9, 2020.
Search Report of ROC (Taiwan) Patent Application No. 109124069 dated May 15, 2021.
English Translation of Search Report of ROC (Taiwan) Patent Application No. 109124069 dated May 15, 2021.
Chi et al., "Anti-tumor Activity of Toll-Like Receptor 7 Agonists", Frontiers in Pharmacology, vol. 8 (304) pp. 1-10 (2017).
Dietsch et al., "Coordinated Activation of Toll-Like Receptor8 (TLR8) and NLRP3 by the TLR8 Agonist, VTX-2337, Ignites Tumoricidal Natural Killer Cell Activity", https://journals.plos.org/plosone/article, pp. 1-11 (2016).
Moghadam et al., "Toll-like receptors: The role in bladder cancer development, progression and immunotherapy, The Scandinavian Foundation for Immunology", 90:e12818 (2019).
Larson, et al., "Design and Synthesis of N1-Modified Imidazoquinoline Agonists for Selective Activation of Toll-like Receptors 7 and 8", ACS Medicinal Chemistry Letters, 2017, 1148-1152, (8).

(Continued)

*Primary Examiner* — Charanjit Aulakh
(74) *Attorney, Agent, or Firm* — Beau Burton

(57) ABSTRACT

The present invention relates to imidazo-pyridinyl compounds, or a pharmaceutically acceptable salt thereof, to pharmaceutical compositions comprising such compounds and salts, and to methods of using such compounds, salts and compositions for the treatment of abnormal cell growth, including cancer, in a subject.

14 Claims, No Drawings

(56) References Cited

OTHER PUBLICATIONS

Salunke, et al., "Structure-Activity Relationships in Human Toll-like Receptor 8-Active 2,3-diamino-furo[2,3-c] pyridines", J. Med. Chem., 2012, 8137-8151, 55(18).
Yoo, et al., "Structure-activity relationships in Toll-like receptor 7 agonistic 1H-imidazo[4,5-c]pyridines", Organic & Biomolecular Chemistry, 2013, 6526-6545, 11.

* cited by examiner

TOLL-LIKE RECEPTOR AGONISTS

BACKGROUND OF THE INVENTION

Toll-like receptors (TLRs) are a family of transmembrane proteins that recognize structurally conserved molecules that are derived from and unique to pathogens, referred to as pathogen-associated molecular patterns (PAMPS). As such, TLRs function in the mammalian immune system as frontline sensors of pathogen-associated molecular patterns, detecting the presence of invading pathogens (Takeuchi and Akira 2010 Cell 140:805-820). TLR engagement in sentinel immune cells causes biosynthesis of selected cytokines (e.g., type I interferons), induction of costimulatory molecules, and increased antigen presentation capacity. These are important molecular mechanisms that activate innate and adaptive immune responses. Accordingly, agonists and antagonists of TLRs find use in modulating immune responses. TLR agonists are typically employed to stimulate immune responses, whereas TLR antagonists are typically employed to inhibit immune responses (Gosu et al 2012. Molecules 17:13503-13529).

The human genome contains 10 known TLRs, of these TLR3, TLR7, TLR8, and TLR9 recognize nucleic acids and their degradation products. The distribution of TLR7, TLR8, and TLR9 is restricted to the endosomal compartments of cells and they are preferentially expressed in cells of the immune system. In the activated dimeric receptor configuration TLR7 and TLR8 recognize single strand RNA at one ligand binding site and the ribonucleoside degradation products guanosine and uridine, respectively, (as well as small molecule ligands with related structural motifs) at a second ligand binding site (Zhang et al 2016 Immunity 45(4); 737-748: Tanji et al 2015 Nat Struct Mol Biol 22: 109-115).

Some small-molecule TLR7 or TLR8 agonists have been identified. Those agonists can be grouped into purine-like molecules, such as 7-thia-8-oxoguanosine (TOG, isatoribine) or the imidazoquinoline-based compounds such as imiquimod. Imiquimod is so far the only approved TLR7 agonist, marketed as a 5% cream (Aldara). It generates approximately 80% 5-year clearance of superficial basal cell carcinomas, which is the most common cancer worldwide, thus demonstrating the importance of TLR7 agonists in cancer immunotherapy. The functional expression of TLR7 appears to be restricted to specific immune cells. Engagement of TLR7 in plasmacytoid dendritic cells leads to the induction of interferon α/β, which plays essential functions in the control of the adaptive immune response (Bao and Liu 2013 Protein Cell 4:40-5).

Engagement of TLR8 in myeloid dendritic cells, monocytes and monocyte-derived dendritic cells induces a prominent pro-inflammatory cytokine profile, characterized by increased production of tumor necrosis factor-a, interleukin-12, and IL-18 (Eigenbrod et al J Immunol, 2015, 195,1092-1099).

Small molecule TLR agonists have also been investigated for use as vaccine adjuvants (Dowling, ImmunoHorizons 2018, 2(6) 185-197).

Thus, virtually all major types of monocytic and dendritic cells can be activated by agonists of TLR7 and TLR8 to become highly effective antigen-presenting cells, thereby promoting an effective innate and adaptive immune response. Most antigen presenting cell types express only one of these two receptors, accordingly small molecules with potent agonist activity against both TLR7 and TLR8 receptors are potentially more effective immune adjuvants than TLR7 agonists alone.

Thus, a TLR7/TLR8 (TLR7/8) small molecule agonist with dual bioactivity could provide further benefit over a more selective TLR7 agonist and would cause innate immune responses in a wider range of antigen presenting cells and other key immune cell types, including plasmacytoid and myeloid dendritic cells, monocytes, and B cells (van Haren et al 2016 J Immunol 197:4413-4424; Ganapathi et al 2015 Plos One 10(8).e0134640). Such potent dual TLR7/8 agonists may also be effective in stimulating effective anti-tumor responses in cancer (Singh et al 2014 J. Immunol 193 4722-4731: Sabado et al 2015 Cancer Immunol Res 3 278-287, Spinetti et al 2016 Oncoimmunol 9; 5(11):e1230578: Patil et al 2016 Mini Rev Med Chem 16:309-322).

Despite the success of Imiquimod (Aldera) in treating superficial basal cell carcinoma, there remains a need for not only more potent TLR7 agonists, but also balanced, potent TLR7/8 agonists to expand treatment options for patients for various cancers. These treatment options could be local administrations which would deliver the drug to the tumor directly, whilst limiting systemic side effects. Alternatively, systemically administered TLR7 agonists or TLR7/8 agonists would have the advantage of being able to reach difficult to administer tumors as well as multiple tumors, through the systemic circulation.

SUMMARY OF THE INVENTION

The present invention provides, in part, compounds of Formula (I), including Formula (Ia) and (Ib), collectively, a compound of the invention, or a pharmaceutically acceptable salt thereof. Such compounds activate the human TLR7 (hTLR7) and also activate the human TLR8 (hTLR8), thereby affecting biological functions. In some embodiments, the invention provides compounds that are dual agonists that are selective for both TLR7 and TLR8 (TLR7/8 agonists). In another embodiment, the invention provides compounds that are agonists that are selective for TLR7. Another embodiment provides pharmaceutical compositions and medicaments comprising the compounds of the invention, or a pharmaceutically acceptable salt thereof, alone or in combination with additional anticancer therapeutic agents.

The present invention also provides, in part, methods for preparing the compounds, pharmaceutically acceptable salts and compositions of the invention, and methods of using the foregoing alone or in combination with additional anticancer therapeutic agents.

In one aspect, the invention provides a compound of Formula (I):

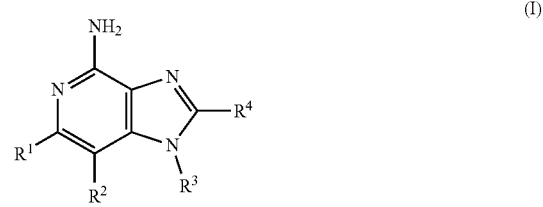

or a pharmaceutically acceptable salt thereof, wherein
$R^1$ and $R^2$ are independently $C_{1-3}$ alkyl; or
$R^1$ and $R^2$ are joined to form a 5- to 7-membered carbocyclic ring, wherein said carbocyclic ring may be saturated or unsaturated;

$R^3$ is

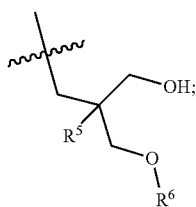

$R^4$ is $C_{1-6}$ alkyl, or $(CH_2)_nO(CH_2)_mCH_3$, wherein the $C_{1-6}$ alkyl or any carbon of the $(CH_2)_nO(CH_2)_mCH_3$ group is substituted with 0 to 3 halogen as valency allows;

$R^5$ is $C_{1-3}$ alkyl, or $OC_{1-3}$ alkyl, wherein the $C_{1-3}$ alkyl is substituted by 0 to 3 F;

$R^6$ is H, or $C_{1-3}$ alkyl, wherein the $C_{1-3}$ alkyl is substituted with 0 to 3 F;

m is 0 to 2; and n is 1 to 3.

In another aspect, the invention provides a pharmaceutical composition comprising a compound of the invention, according to any of the formulae described herein, or a pharmaceutically acceptable salt thereof, and a pharmaceutically acceptable carrier or excipient. In some embodiments, the pharmaceutical composition comprises two or more pharmaceutically acceptable carriers and/or excipients.

In another aspect, the invention also provides therapeutic methods and uses comprising administering a compound of the invention, or a pharmaceutically acceptable salt thereof.

In another aspect, the invention provides a method for the treatment of abnormal cell growth, in particular, cancer, in a subject in need thereof, comprising administering to the subject a therapeutically effective amount of a compound of the invention, or a pharmaceutically acceptable salt thereof. Compounds of the invention may be administered as single agents or may be administered in combination with other anti-cancer therapeutic agents, including standard of care agents appropriate for the particular form of cancer. This also includes use of a compound of the invention, or a pharmaceutically acceptable salt thereof, in the manufacture of a medicament for treating abnormal cell growth, in particular, cancer, in a subject in need thereof.

In another aspect, the invention provides a compound of the invention, or a pharmaceutically acceptable salt thereof, for use as a medicament, in particular a medicament for the treatment of abnormal cell growth, such as cancer.

In yet another aspect, the invention provides the use of a compound of the invention, or a pharmaceutically acceptable salt thereof, for the manufacture of a medicament for the treatment of abnormal cell growth, such as cancer, in a subject.

In another aspect, the invention includes within its scope the pharmaceutically acceptable salts of the compounds of the invention. Accordingly, the phrase "or a pharmaceutically acceptable salt thereof" is implicit in the description of all compounds described herein unless explicitly indicated to the contrary.

DETAILED DESCRIPTION OF THE INVENTION

As provided, the invention concerns a compound of Formula (I) as provided above.

The present invention may be understood more readily by reference to the following detailed description of additional embodiments of the invention and the Examples included herein. It is to be understood that the terminology used herein is provided for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents. The term "about" means having a value falling within an accepted standard of error of the mean, when considered by one of ordinary skill in the art.

The term "alkyl", as used herein, means a straight or branched chain monovalent hydrocarbon group of formula —$C_nH_{(2n+1)}$. Non-limiting examples include methyl, ethyl, propyl, butyl, 2-methyl-propyl, 1,1-dimethylethyl, pentyl and hexyl.

In some instances, the number of carbon atoms in a hydrocarbon group (e.g. alkyl) is indicated by the prefix "$C_x$-$C_y$" or "$C_{x-y}$", wherein x is the minimum and y is the maximum number of carbon atoms in the group. Thus, for example, "($C_1$-$C_6$)alkyl" or "$C_{1-6}$ alkyl" refers to an alkyl substituent containing from 1 to 6 carbon atoms.

The term "halogen", as used herein, refers to fluoride, chloride, bromide, or iodide.

The term "haloalkyl", as used herein, refers to an alkyl group that is substituted with at least one halogen substituent. Where more than one hydrogen atom is replaced with a halogen atom, the halogens may be identical or different. Non-limiting examples include fluoromethyl, difluoromethyl, trifluoromethyl and 2,2,2-trifluoroethyl.

As used herein, a "biotherapeutic agent" means a biological molecule, such as an antibody or fusion protein, that blocks ligand/receptor signaling in any biological pathway that supports tumor maintenance and/or growth or suppresses the anti-tumor immune response.

As used herein, a "chemotherapeutic agent" is a chemical compound useful in the treatment of cancer. Chemotherapeutic agents useful in the treatment methods of the present invention include cytostatic and/or cytotoxic agents. Chemotherapeutic agents include the agent itself or any pharmaceutically acceptable salt, co-crystal, or solvate thereof. Chemotherapeutic agents are further described herein.

As used herein, the following terms are used interchangeably and mean any one or more therapeutic agent, other than a compound of the invention, that is or can be used in the treatment of cancer: "additional anti-cancer therapeutic agent" or "additional chemotherapeutic agent" or "additional therapeutic agent."

A biotherapeutic agent and a chemotherapeutic agent are both examples of an additional anti-cancer therapeutic agent.

As used herein, a "cytotoxic agent" refers to an agent that has a cytotoxic and/or cytostatic effect on a cell and a "cytostatic effect" refers to the inhibition of cell proliferation.

As used herein, a "cytostatic agent" refers to an agent that has a cytostatic effect on a cell, thereby inhibiting the growth and/or expansion of a specific subset of cells (i.e., tumor cells).

As used herein, an "immunomodulating agent" refers to an agent that stimulates the immune response though the production of cytokines and/or antibodies and/or modulating T cell function thereby inhibiting or reducing the growth of a subset of cells (i.e., tumor cells) either directly or indirectly by allowing another agent to be more efficacious.

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, an OX40 agonist that consists essentially of a recited amino acid sequence may also include one or more amino acids, including substitutions of one or more amino acid residues, which do not materially affect the properties of the binding compound.

As used herein, an "effective dosage" or "effective amount" of drug, compound or pharmaceutical composition is an amount sufficient to affect any one or more beneficial or desired, including biochemical, histological and/or behavioral symptoms, of the disease, its complications and intermediate pathological phenotypes presenting during development of the disease. For therapeutic use, a "therapeutically effective amount" refers to that amount of a compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, (4) relieving to some extent (or, preferably, eliminating) one or more signs or symptoms associated with the cancer, (5) decreasing the dose of other medications required to treat the disease, and/or (6) enhancing the effect of another medication, and/or (7) delaying the progression of the disease in a patient.

An effective dosage can be administered in one or more administrations. For the purposes of this invention, an effective dosage of drug, compound, or pharmaceutical composition is an amount sufficient to accomplish prophylactic or therapeutic treatment either directly or indirectly. As is understood in the clinical context, an effective dosage of drug, compound or pharmaceutical composition may or may not be achieved in conjunction with another drug, compound or pharmaceutical composition.

A "pharmaceutical composition" refers to a mixture of one or more of the compounds of the invention, or a pharmaceutically acceptable salt, solvate, hydrate or prodrug thereof as an active ingredient, and at least one pharmaceutically acceptable carrier or excipient. In some embodiments, the pharmaceutical composition comprises two or more pharmaceutically acceptable carriers and/or excipients. In other embodiments, the pharmaceutical composition further comprises at least one additional anticancer therapeutic agent.

In one aspect, the invention provides a pharmaceutical composition comprising a compound of the invention, or a pharmaceutically acceptable salt thereof, and a pharmaceutically acceptable carrier or excipient. In some embodiments, the pharmaceutical composition comprises two or more pharmaceutically acceptable carriers and/or excipients.

In some embodiments, the pharmaceutical composition further comprises at least one additional anti-cancer therapeutic agent. In some such embodiments, the combination provides an additive, greater than additive, or synergistic anti-cancer effect.

"Tumor" as it applies to a subject diagnosed with, or suspected of having, a cancer refers to a malignant or potentially malignant neoplasm or tissue mass of any size and includes primary tumors and secondary neoplasms. A solid tumor is an abnormal growth or mass of tissue that usually does not contain cysts or liquid areas. Examples of solid tumors are sarcomas, carcinomas, and lymphomas. Leukemias (cancers of the blood) generally do not form solid tumors (National Cancer Institute, Dictionary of Cancer Terms).

"Tumor burden" or "tumor load", refers to the total amount of tumorous material distributed throughout the body. Tumor burden refers to the total number of cancer cells or the total size of tumor(s), throughout the body, including lymph nodes and bone marrow. Tumor burden can be determined by a variety of methods known in the art, such as, e.g., using calipers, or while in the body using imaging techniques, e.g., ultrasound, bone scan, computed tomography (CT), or magnetic resonance imaging (MRI) scans.

The term "tumor size" refers to the total size of the tumor which can be measured as the length and width of a tumor. Tumor size may be determined by a variety of methods known in the art, such as, e.g., by measuring the dimensions of tumor(s) upon removal from the subject, e.g., using calipers, or while in the body using imaging techniques, e.g., bone scan, ultrasound, CR or MRI scans.

As used herein, "subject" refers to a human or animal subject. When the subject is a human, the subject may also be referred to as a "patient".

The term "treat" or "treating" a cancer as used herein means to administer a compound of the present invention to a subject having cancer, or diagnosed with cancer, to achieve at least one positive therapeutic effect, such as, for example, reduced number of cancer cells, reduced tumor size, reduced rate of cancer cell infiltration into peripheral organs, or reduced rate of tumor metastases or tumor growth, reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

For the purposes of this invention, beneficial or desired clinical results include, but are not limited to, one or more of the following: reducing the proliferation of (or destroying) neoplastic or cancerous cell; inhibiting metastasis or neoplastic cells; shrinking or decreasing the size of a tumor; remission of the cancer; decreasing symptoms resulting from the cancer; increasing the quality of life of those suffering from the cancer; decreasing the dose of other medications required to treat the cancer; delaying the progression of the cancer; curing the cancer; overcoming one or more resistance mechanisms of the cancer; and/or prolonging survival of patients the cancer. Positive therapeutic effects in cancer can be measured in several ways (see, for example, W. A. Weber, Assessing tumor response to therapy, J. Nucl. Med. 50 Suppl. 1:1S-10S (2009). For example, with respect to tumor growth inhibition (T/C), according to the National Cancer Institute (NCI) standards, a T/C less than or equal to 42% is the minimum level of anti-tumor activity. A T/C<10% is considered a high anti-tumor activity level, with T/C (%)=median tumor volume of the treated/median tumor volume of the control×100.

In some embodiments, the treatment achieved by a compound of the invention is defined by reference to any of the following: partial response (PR), complete response (CR), overall response (OR), progression free survival (PFS), disease free survival (DFS) and overall survival (OS). PFS, also referred to as "Time to Tumor Progression" indicates the length of time during and after treatment that the cancer does not grow and includes the amount of time patients have experienced a CR or PR, as well as the amount of time patients have experienced stable disease (SD). DFS refers to the length of time during and after treatment that the patient remains free of disease. OS refers to a prolongation in life expectancy as compared to naïve or untreated subjects or patients. In some embodiments, response to a combination of the invention is any of PR, CR, PFS, DFS, OR or OS that is assessed using Response Evaluation Criteria in Solid Tumors (RECIST) 1.1 response criteria.

The term "additive" is used to mean that the result of the combination of two compounds, components or targeted agents is no greater than the sum of each compound, component or targeted agent individually.

The term "synergy" or "synergistic" are used to mean that the result of the combination of two compounds, components or targeted agents is greater than the sum of each compound, component or targeted agent individually. This improvement in the disease, condition or disorder being treated is a "synergistic" effect. A "synergistic amount" is an amount of the combination of the two compounds, components or targeted agents that results in a synergistic effect, as "synergistic" is defined herein.

Determining a synergistic interaction between one or two components, the optimum range for the effect and absolute dose ranges of each component for the effect may be definitively measured by administration of the components over different dose ranges, and/or dose ratios to patients in need of treatment. However, the observation of synergy in in vitro models or in vivo models can be predictive of the effect in humans and other species and in vitro models or in vivo models exist, as described herein, to measure a synergistic effect. The results of such studies can also be used to predict effective dose and plasma concentration ratio ranges and the absolute doses and plasma concentrations required in humans and other species such as by the application of pharmacokinetic and/or pharmacodynamics methods.

The treatment regimen for a compound of the invention that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the chi2-test the U-test according to Mann and Whitney, the Kruskal-Wallis test (H-test), Jonckheere-Terpstrattesty and the Wilcon on-test.

The terms "treatment regimen", "dosing protocol" and "dosing regimen" are used interchangeably to refer to the dose and timing of administration of each compound of the invention, alone or in combination with another therapeutic agent.

"Ameliorating" means a lessening or improvement of one or more symptoms upon treatment with a combination described herein, as compared to not administering the combination. "Ameliorating" also includes shortening or reduction in duration of a symptom.

"Abnormal cell growth", as used herein, unless otherwise indicated, refers to cell growth that is independent of normal regulatory mechanisms (e.g., loss of contact inhibition). Abnormal cell growth may be benign (not cancerous), or malignant (cancerous).

The terms "cancer" or "cancerous" refers to any malignant and/or invasive growth or tumor caused by abnormal cell growth. Cancer includes primary cancer that originates at a specific site in the body, a metastatic cancer that has spread from the place in which it started to other parts of the body, a recurrence from the original primary cancer after remission, and a second primary cancer that is a new primary cancer in a patient with a history of previous cancer of a different type from the second primary cancer. Cancer includes solid tumors named for the type of cells that form them, cancer of blood, bone marrow, or the lymphatic system. Examples of solid tumors include sarcomas and carcinomas. Cancers of the blood include leukemia, lymphoma and myeloma. Additional examples of cancer include blastomas and an actinic keratosis. Cancer also includes primary cancer or metastases of a site selected from the group consisting of oral cavity, digestive system, respiratory system, skin, breast, genital system, urinary system, ocular system, nervous system, endocrine system, and lymphoma.

Unless indicated otherwise, all references herein to the inventive compounds include references to salts, solvates, hydrates and complexes thereof, and to solvates, hydrates and complexes of salts thereof, including polymorphs, stereoisomers, and isotopically labelled versions thereof.

Compounds of the invention may exist in the form of pharmaceutically acceptable salts such as, e.g., acid addition salts and base addition salts of the compounds of one of the formulae provided herein. As used herein, the term "pharmaceutically acceptable salt" refers to those salts which retain the biological effectiveness and properties of the parent compound. The phrase "pharmaceutically acceptable salt(s)", as used herein, unless otherwise indicated, includes salts of acidic or basic groups which may be present in the compounds of the formulae disclosed herein.

For example, the compounds of the invention that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

The acids that may be used to prepare pharmaceutically acceptable acid addition salts of such basic compounds of those that form non toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate salts.

Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne 1,4 dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne 1,6 dioate, hexylresorcinate, hydrabamine, hydrobromide, hydrochloride, γ hydroxybutyrate, iodide, isobutyrate, isothionate, lactate, lactobionate, laurate, malate, maleate, malonate, mandelate, mesylate, metaphosphate, methane sulfonate, methylsulfate, monohydrogenphosphate, mucate, napsylate, naphthalene 1 sulfonate, naphthalene 2 sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate and valerate salts.

Illustrative examples of suitable salts include organic salts derived from amino acids, such as glycine and arginine, ammonia, primary, secondary, and tertiary amines and cyclic amines, such as piperidine, morpholine and piperazine, and inorganic salts derived from sodium, calcium, potassium, magnesium, manganese, iron, copper, zinc, aluminum and lithium.

The compounds of the invention that include a basic moiety, such as an amino group, may form pharmaceutically acceptable salts with various amino acids, in addition to the acids mentioned above.

Alternatively, the compounds useful that are acidic in nature may be capable of forming base salts with various pharmacologically acceptable cations. Examples of such salts include the alkali metal or alkaline earth metal salts and particularly, the sodium and potassium salts. These salts are all prepared by conventional techniques. The chemical bases which are used as reagents to prepare the pharmaceutically acceptable base salts of this invention are those which form non toxic base salts with the acidic compounds herein. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The chemical bases that may be used as reagents to prepare pharmaceutically acceptable base salts of the compounds of the invention that are acidic in nature are those that form non toxic base salts with such compounds. Such non toxic base salts include, but are not limited to, those derived from such pharmacologically acceptable cations such as alkali metal cations (e.g., potassium and sodium) and alkaline earth metal cations (e.g., calcium and magnesium), ammonium or water soluble amine addition salts such as N methylglucamine (meglumine), and the lower alkanolammonium and other base salts of pharmaceutically acceptable organic amines.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley VCH, 2002). Methods for making pharmaceutically acceptable salts of compounds of the invention, and of interconverting salt and free base forms, are known to one of skill in the art.

Salts of the present invention can be prepared according to methods known to those of skill in the art. A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non ionized.

It will be understood by those of skill in the art that the compounds of the invention in free base form having a basic functionality may be converted to the acid addition salts by treating with a stoichiometric excess of the appropriate acid. The acid addition salts of the compounds of the invention may be reconverted to the corresponding free base by treating with a stoichiometric excess of a suitable base, such as potassium carbonate or sodium hydroxide, typically in the presence of aqueous solvent, and at a temperature of between about 0° C. and 100° C. The free base form may be isolated by conventional means, such as extraction with an organic solvent. In addition, acid addition salts of the compounds of the invention may be interchanged by taking advantage of differential solubilities of the salts, volatilities or acidities of the acids, or by treating with the appropriately loaded ion exchange resin. For example, the interchange may be affected by the reaction of a salt of the compounds of the invention with a slight stoichiometric excess of an acid of a lower pK than the acid component of the starting salt. This conversion is typically carried out at a temperature between about 0° C. and the boiling point of the solvent being used as the medium for the procedure. Similar exchanges are possible with base addition salts, typically via the intermediacy of the free base form.

The compounds of the invention may exist in both unsolvated and solvated forms. When the solvent or water is tightly bound, the complex will have a well defined stoichiometry independent of humidity. When, however, the solvent or water is weakly bound, as in channel solvates and hygroscopic compounds, the water/solvent content will be dependent on humidity and drying conditions. In such cases, non stoichiometry will be the norm. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug host inclusion complexes wherein, in contrast to the aforementioned solvates, the drug and host are present in stoichiometric or non stoichiometric amounts. Also included are complexes of the drug containing two or more organic and/or inorganic components which may be in stoichiometric or non stoichiometric amounts. The resulting complexes may be ionized, partially ionized, or non ionized. For a review of such complexes, see J Pharm Sci, 64 (8), 1269 1288 by Haleblian (August 1975), the disclosure of which is incorporated herein by reference in its entirety.

The invention also relates to prodrugs of the compounds of the formulae provided herein. Thus, certain derivatives of compounds of the invention which may have little or no pharmacological activity themselves can, when administered to a patient, be converted into the inventive compounds, for example, by hydrolytic cleavage. Such derivatives are referred to as 'prodrugs'. Further information on the use of prodrugs may be found in 'Pro drugs as Novel Delivery Systems, Vol. 14, ACS Symposium Series (T Higuchi and W Stella); 'Bioreversible Carriers in Drug Design', Pergamon Press, 1987 (ed. E B Roche, American Pharmaceutical Association), and Guarino, V. R; Stella, V. J.: *Biotech Pharm. Aspects* 2007 5 (Pt2) 133-187, the disclosures of which are incorporated herein by reference in their entireties.

Prodrugs in accordance with the invention can, for example, be produced by replacing appropriate functionalities present in the inventive compounds with certain moieties known to those skilled in the art as 'pro moieties' as described, for example, in "Design of Prodrugs" by H Bundgaard (Elsevier, 1985), the disclosure of which is incorporated herein by reference in its entirety.

Some non limiting examples of prodrugs in accordance with the invention include:

(i) where the compound contains a carboxylic acid functionality (COOH), an ester thereof, for example, replacement of the hydrogen with ($C_1$-$C_6$)alkyl;

(ii) where the compound contains an alcohol functionality (OH), an ether thereof, for example, replacement of the hydrogen with ($C_1$-$C_6$)alkanoyloxymethyl, or with a phosphate ether group; and (iii) where the compound contains a primary or secondary amino functionality (NH2 or NHR where R≠H), an amide thereof, for example, replacement of one or both hydrogens with a suitably metabolically labile group, such as an amide, carbamate, urea, phosphonate, sulfonate, etc.

Further examples of replacement groups in accordance with the foregoing examples and examples of other prodrug types may be found in the aforementioned references.

Finally, certain inventive compounds may themselves act as prodrugs of other of the inventive compounds.

Also included within the scope of the invention are metabolites of compounds of the formulae described herein, i.e., compounds formed in vivo upon administration of the drug.

The compounds of the formulae provided herein may have asymmetric carbon atoms. The carbon carbon bonds of the compounds of the invention may be depicted herein using a solid line ( —— ) a solid wedge ( ◢ ), or a dotted wedge ( ⋯⋯ ). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included and the attached stereocenter. For example, unless stated otherwise, it is intended that the compounds of the invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Compounds of the invention that have chiral centers may exist as stereoisomers, such as racemates, enantiomers, or diastereomers.

Stereoisomers of the compounds of the formulae herein can include cis and trans isomers, optical isomers such as (R) and (S) enantiomers, diastereomers, geometric isomers, rotational isomers, atropisomers, conformational isomers, and tautomers of the compounds of the invention, including compounds exhibiting more than one type of isomerism; and mixtures thereof (such as racemates and diastereomeric pairs).

Also included are acid addition salts or base addition salts, wherein the counterion is optically active, for example, d lactate or l lysine, or racemic, for example, dl tartrate or dl arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of the invention may exhibit the phenomena of tautomerism and structural isomerism. For example, the compounds may exist in several tautomeric forms, including the enol and imine form, and the keto and enamine form and geometric isomers and mixtures thereof. All such tautomeric forms are included within the scope of compounds of the invention. Tautomers exist as mixtures of a tautomeric set in solution. In solid form, usually one tautomer predominates. Even though one tautomer may be described, the present invention includes all tautomers of the compounds of the formulae provided.

In addition, some of the compounds of the invention may form atropisomers (e.g., substituted biaryls). Atropisomers are conformational stereoisomers which occur when rotation about a single bond in the molecule is prevented, or greatly slowed, as a result of steric interactions with other parts of the molecule and the substituents at both ends of the single bond are unsymmetrical. The interconversion of atropisomers is slow enough to allow separation and isolation under predetermined conditions. The energy barrier to thermal racemization may be determined by the steric hindrance to free rotation of one or more bonds forming a chiral axis.

Where a compound of the invention contains an alkenyl or alkenylene group, geometric cis/trans (or Z/E) isomers are possible. Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC) or superfluid critical chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1 phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The enantiomeric purity of compounds described herein may be described in terms of enantiomeric excess (ee), which indicates the degree to which a sample contains one enantiomer in greater amounts than the other. A racemic mixture has an ee of 0%, while a single completely pure enantiomer has an ee of 100%. Similarly, diastereomeric purity may be described in terms of diasteriomeric excess (de).

The present invention also includes isotopically labeled compounds, which are identical to those recited in one of the formulae provided, but for the fact that one or more atoms are replaced by an atom having an atomic mass or mass number different from the atomic mass or mass number usually found in nature.

Isotopically labeled compounds of the invention can generally be prepared by conventional techniques known to those skilled in the art or by processes analogous to those described herein, using an appropriate isotopically labeled reagent in place of the non labeled reagent otherwise employed.

Examples of isotopes that may be incorporated into compounds of the invention include isotopes of hydrogen, carbon, nitrogen, oxygen, phosphorus, sulfur, fluorine and chlorine, such as, but not limited to, $^2H$, $^3H$, $^{13}C$, $^{14}C$, $^{15}N$, $^{18}O$, $^{17}O$, $^{32}P$, $^{35}S$, $^{18}F$ and $^{36}Cl$. Certain isotopically labeled compounds of the invention, for example those into which radioactive isotopes such as $^3H$ and $^{14}C$ are incorporated, are useful in drug and/or substrate tissue distribution assays. Tritiated, i.e., $^3H$, and carbon 14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half life or reduced dosage requirements and, hence, may be preferred in some circumstances. Isotopically labeled compounds of the invention may generally be prepared by carrying out the procedures disclosed in the Schemes and/or in the Examples and Preparations below, by substituting an isotopically labeled reagent for a non isotopically labeled reagent.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used.

In another embodiment, the invention provides a compound of Formula (Ia)

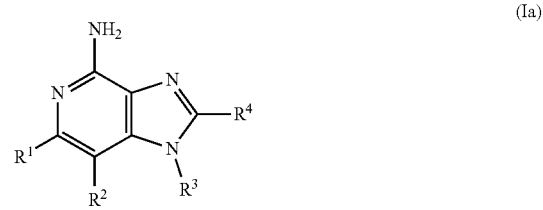

(Ia)

or a pharmaceutically acceptable salt thereof, wherein
$R^1$ and $R^2$ are independently $C_{1-2}$ alkyl; or
$R^1$ and $R^2$ are joined to form a 5- to 7-membered carbocyclic ring, wherein said carbocyclic ring may be saturated or unsaturated;
$R^3$ is

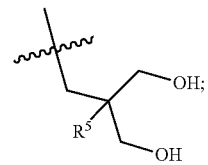

$R^4$ is $C_{3-5}$ alkyl, or $(CH_2)_nO(CH_2)_mCH_3$;
$R^5$ is $C_{1-2}$ alkyl;
m is 1; and
n is 1.

In another embodiment, the invention provides a compound of Formula (Ia), or a pharmaceutically acceptable salt thereof, wherein $R^1$ and $R^2$ are independently $C_{1-2}$ alkyl.

In another embodiment, the invention provides a compound of Formula (Ia), or a pharmaceutically acceptable salt thereof, wherein $R^1$ and $R^2$ are joined to form a 5- to 7-membered carbocyclic ring, wherein said carbocyclic ring may be saturated or unsaturated.

In another embodiment, the invention provides a compound of Formula (Ia), or a pharmaceutically acceptable salt thereof, wherein
$R^1$ and $R^2$ are joined to form a 5- to 7-membered carbocyclic ring, wherein said carbocyclic ring may be saturated; and
$R^4$ is $(CH_2)_nO(CH_2)_mCH_3$.

In another embodiment, the invention provides a compound of Formula (Ia), or a pharmaceutically acceptable salt thereof, wherein the carbocyclic ring is cyclopentyl.

In another embodiment, the invention provides a compound of Formula (Ia), or a pharmaceutically acceptable salt thereof, wherein the carbocyclic ring is cyclohexyl.

In another embodiment, the invention provides a compound of Formula (Ia), or a pharmaceutically acceptable salt thereof, wherein
$R^1$ and $R^2$ are joined to form a 5- to 7-membered carbocyclic ring, wherein said carbocyclic ring may be unsaturated; and
$R^4$ is $C_{3-5}$ alkyl.

In another embodiment, the invention provides a compound of Formula (Ia), or a pharmaceutically acceptable salt thereof, wherein the carbocyclic ring is phenyl.

In another embodiment, the invention provides a compound of Formula (Ib)

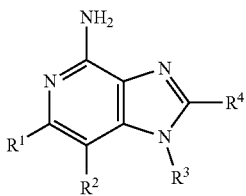

(Ib)

or a pharmaceutically acceptable salt thereof, wherein
$R^1$ and $R^2$ are independently $C_{1-3}$ alkyl; or
$R^1$ and $R^2$ are joined to form a 5- to 7-membered carbocyclic ring, wherein said carbocyclic ring may be saturated or unsaturated;
$R^3$ is

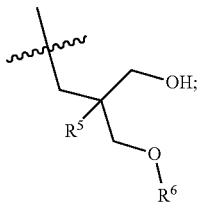

$R^4$ is $C_{1-6}$ alkyl, or $(CH_2)_nO(CH_2)_mCH_3$, wherein said $C_{1-6}$ alkyl or any carbon of the $(CH_2)_nO(CH_2)_mCH_3$ group is substituted with 0 to 3 halogen as valency allows, wherein halogen is F;
$R^5$ is $C_{1-3}$ alkyl, or $OC_{1-3}$ alkyl, wherein the $C_{1-3}$ alkyl is substituted by 0 to 3 F;
$R^6$ is H, or $C_{1-3}$ alkyl, wherein the $C_{1-3}$ alkyl is substituted with 0 to 3 F;
m is 0 to 2; and
n is 1 to 3.

In another embodiment, the invention provides a compound of Formula (Ib), or a pharmaceutically acceptable salt thereof, wherein
$R^1$ and $R^2$ are independently $C_{1-2}$ alkyl; or
$R^1$ and $R^2$ are joined to form a 5- to 7-membered carbocyclic ring, wherein said carbocyclic ring may be saturated or unsaturated;
$R^3$ is

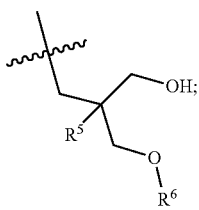

$R^5$ is $C_{1-3}$ alkyl, or $OC_{1-3}$ alkyl, wherein the $C_{1-3}$ alkyl is substituted by 0 to 2 F; and
$R^6$ is H.

In another embodiment, the invention provides a compound of Formula (Ib), or a pharmaceutically acceptable salt thereof, wherein $R^5$ is $C_{1-2}$ alkyl.

In another embodiment, the invention provides a compound of Formula (I), (Ia), (Ib), or a pharmaceutically acceptable salt thereof, wherein $R^4$ is n-propyl, n-butyl, or n-pentyl.

In another embodiment, the invention provides a compound of Formula (I), (Ia), (Ib), or a pharmaceutically acceptable salt thereof, wherein $R^4$ is —$CH_2$—O—$CH_2CH_3$.

In another embodiment, the invention provides a compound of Formula (I), (Ia), (Ib), or a pharmaceutically acceptable salt thereof, wherein $R^5$ is methyl or ethyl.

In another embodiment, the invention provides a compound of Formula (I), (Ia), (Ib), or a pharmaceutically acceptable salt thereof, wherein $R^6$ is H.

Another embodiment of the invention is one or more of each Example described herein, and includes, but is not limited to, the compounds selected from:
2-((4-amino-2-(ethoxymethyl)-6,7-dimethyl-1H-imidazo[4,5-c]pyridin-1-yl)methyl)-2-methylpropane-1,3-diol;
2-((4-amino-2-(ethoxymethyl)-1H-imidazo[4,5-c]quinolin-1-yl)methyl)-2-methylpropane-1,3-diol;
2-((4-amino-2-(ethoxymethyl)-7,8-dihydrocyclopenta[b]imidazo[4,5-d]pyridin-1(6H)-yl)methyl)-2-methylpropane-1,3-diol;
2-((4-amino-2-(ethoxymethyl)-6,7,8,9-tetrahydro-1H-imidazo[4,5-c]quinolin-1-yl)methyl)-2-methylpropane-1,3-diol;
3-(4-amino-2-(ethoxymethyl)-6,7-dimethyl-1H-imidazo[4,5-c]pyridin-1-yl)-2-(methoxymethyl)-2-methylpropan-1-ol;
(R)-3-(4-amino-2-(ethoxymethyl)-6,7-dimethyl-1H-imidazo[4,5-c]pyridin-1-yl)-2-(methoxymethyl)-2-methylpropan-1-ol;
(S)-3-(4-amino-2-(ethoxymethyl)-6,7-dimethyl-1H-imidazo[4,5-c]pyridin-1-yl)-2-(methoxymethyl)-2-methylpropan-1-ol;
2-((4-amino-6,7-dimethyl-2-(2,2,2-trifluoroethyl)-1H-imidazo[4,5-c]pyridin-1-yl)methyl)-2-methylpropane-1,3-diol;
2-((4-amino-2-(ethoxymethyl)-6,7-dimethyl-1H-imidazo[4,5-c]pyridin-1-yl)methyl)-2-ethylpropane-1,3-diol;
2-((4-amino-2-butyl-1H-imidazo[4,5-c]quinolin-1-yl)methyl)-2-methylpropane-1,3-diol;
2-((4-amino-2-butyl-6,7-dimethyl-1H-imidazo[4,5-c]pyridin-1-yl)methyl)-2-methylpropane-1,3-diol; and
2-((4-amino-2-pentyl-1H-imidazo[4,5-c]quinolin-1-yl)methyl)-2-methylpropane-1,3-diol;
or a pharmaceutically acceptable salt thereof.

Another embodiment of the invention is one or more of each Example described herein, and includes, but is not limited to, the compounds selected from:
2-((4-amino-2-butyl-6,7,8,9-tetrahydro-1H-imidazo[4,5-c]quinolin-1-yl)methyl)-2-methylpropane-1,3-diol;
2-((4-amino-2-butyl-7,8-dihydrocyclopenta[b]imidazo[4,5-d]pyridin-1(6H)-yl)methyl)-2-methylpropane-1,3-diol;
2-((4-amino-2-ethyl-1H-imidazo[4,5-c]quinolin-1-yl)methyl)-2-methylpropane-1,3-diol; and
2-((4-amino-2-propyl-1H-imidazo[4,5-c]quinolin-1-yl)methyl)-2-methylpropane-1,3-diol;
or a pharmaceutically acceptable salt thereof.

Another embodiment of the invention provides a pharmaceutical composition comprising the compounds of Formula (I) and any embodiments thereof, or a pharmaceutically acceptable salt thereof, and a pharmaceutically acceptable carrier or excipient.

Another embodiment of the invention provides a method for the treatment of cancer in a subject in need thereof, comprising administering to the subject a therapeutically effective amount of the compounds of Formula (I) and any embodiments thereof, or a pharmaceutically acceptable salt thereof.

Cancers to be treated include squamous cell carcinoma, basal cell carcinomas, myeloma, small-cell lung cancer, non-small cell lung cancer, glioma, Hodgkin's lymphoma, non-Hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, uterine cancer, bladder cancer, including non-muscular invasive bladder cancer, hepatoma, breast cancer, and head and neck cancer.

More particular examples of cancers to be treated include basal cell carcinomas, small-cell lung cancer, non-small cell lung cancer, non-Hodgkin's lymphoma, ovarian cancer, colorectal cancer, kidney cancer, prostate cancer, thyroid cancer, melanoma, pancreatic cancer, bladder cancer (non-muscular invasive bladder cancer), hepatoma, breast cancer, and head and neck cancer.

Another embodiment of the invention concerns treatment of cancers selected from basal cell carcinomas, ovarian cancer, melanoma, non-muscular invasive bladder cancer, breast cancer, and head and neck cancer.

Another embodiment of the invention concerns treatment melanoma, gastrointestinal (tract) cancer, breast cancer, ovarian cancer, and head and neck cancer.

Another embodiment of the invention concerns treatment cancers of the gastrointestinal tract. Such gastrointestinal cancers include cancer of the mouth, esophagus, stomach, biliary system, pancreas, small intestine, large intestine, rectum, and anus.

Another embodiment of the invention concerns treatment of non-muscular invasive bladder cancer.

Another embodiment of the invention concerns the compounds of Formula (I) and any embodiments thereof, or a pharmaceutically acceptable salt thereof, for use in the treatment of cancer in a subject in need thereof.

Another embodiment of the invention concerns the compounds of Formula (I) and any embodiments thereof, or a pharmaceutically acceptable salt thereof, for use in the treatment of cancer, wherein said treatment comprises the administration of an additional therapeutic agent.

In another aspect, the invention provides a method of inhibiting cancer cell proliferation in a subject, comprising administering to the subject a compound of the invention, or a pharmaceutically acceptable salt thereof, in an amount effective to inhibit cell proliferation.

In another aspect, the invention provides a method of inhibiting cancer cell invasiveness in a subject, comprising administering to the subject a compound of the invention, or a pharmaceutically acceptable salt thereof, in an amount effective to inhibit cell invasiveness.

In another aspect, the invention provides a method of inducing apoptosis in cancer cells in a subject, comprising administering to the subject a compound of the invention, or a pharmaceutically acceptable salt thereof, in an amount effective to induce apoptosis.

In another aspect, the invention provides a method of inhibiting cancer cell metastasis in a subject, comprising administering to the subject a compound of the invention, or a pharmaceutically acceptable salt thereof, in an amount effective to inhibit cell metastasis.

In another aspect, the invention provides a method of inhibiting angiogenesis in a subject, comprising administering to the subject a compound of the invention, or a pharmaceutically acceptable salt thereof, in an amount effective to inhibit angiogenesis.

In another aspect, the invention provides a method for the treatment of cancer in a subject in need thereof, comprising administering to the subject a therapeutically effective amount of the compound of the invention, or a pharmaceutically acceptable salt thereof. Said method also includes administering the compound of the invention with at least one additional therapeutic agent.

The invention also provides methods of preventing an infectious disease in a subject in need thereof, comprising administration of a pharmaceutical composition in an amount sufficient to prevent an infectious disease in said subject. That is, in some embodiments, the present disclosure provides prophylactic vaccines. In some embodiments, the mammalian subject is at risk of exposure to an infectious agent. "Preventing" an infectious disease means to protect a subject from developing an infectious disease. In some embodiments, preventing an infectious disease further comprises protecting a subject front being infected with an infectious agent (e g., protecting a subject from developing an acute or a chronic infection). Additionally, the present disclosure provides methods of ameliorating a symptom of an infectious disease in a mammalian subject in need thereof, comprising administration of a pharmaceutical composition in an amount sufficient to ameliorate a symptom of an infectious disease in said subject. That is, in some embodiments the present disclosure provides therapeutic vaccines. In some embodiments, the subject is acutely or chronically infected with an infectious agent. The infectious disease may be a viral (e.g., hepatitis, herpes or human papilloma viruses), bacterial, fungal, or parasitic disease. In some embodiments, the pharmaceutical composition further comprises a viral, bacterial, fungal, or parasitic antigen. "Ameliorating" a symptom of an infectious disease means to improve a symptom preferably diminishing the extent of the disease.

Therapeutic Methods and Uses

The invention further provides therapeutic methods and uses comprising administering the compounds of the invention, or pharmaceutically acceptable salts thereof, alone or in combination with other therapeutic agents or palliative agents.

In one aspect, the invention provides a method for the treatment of abnormal cell growth in a subject in need thereof, comprising administering to the subject a therapeutically effective amount of a compound of the invention, or a pharmaceutically acceptable salt thereof.

In another aspect, the invention provides a method for the treatment of abnormal cell growth in a subject in need thereof, comprising administering to the subject an amount of a compound of the invention, or a pharmaceutically acceptable salt thereof, in combination with an amount of an additional therapeutic agent (e.g., an anticancer therapeutic agent), which amounts are together effective in treating said abnormal cell growth.

In another aspect, the invention provides a compound of the invention, or a pharmaceutically acceptable salt thereof, for use in the treatment of abnormal cell growth in a subject.

In a further aspect, the invention provides the use of a compound of the invention, or a pharmaceutically acceptable salt thereof, for the treatment of abnormal cell growth in a subject.

In another aspect, the invention provides a pharmaceutical composition for use in the treatment of abnormal cell growth in a subject in need thereof, which pharmaceutical composition comprises a compound of the invention, or a pharmaceutically acceptable salt thereof, and a pharmaceutically acceptable carrier or excipient.

In another aspect, the invention provides a compound of the invention, or a pharmaceutically acceptable salt thereof, for use as a medicament, in particular a medicament for the treatment of abnormal cell growth.

In yet another aspect, the invention provides the use of a compound of the invention, or a pharmaceutically acceptable salt thereof, for the manufacture of a medicament for the treatment of abnormal cell growth in a subject.

In frequent embodiments of the methods provided herein, the abnormal cell growth is cancer. Compounds of the invention may be administered as single agents or may be administered in combination with other anti-cancer therapeutic agents, in particular with standard of care agents appropriate for the particular cancer.

In some embodiments, the methods provided result in one or more of the following effects: (1) inhibiting cancer cell proliferation; (2) inhibiting cancer cell invasiveness; (3) inducing apoptosis of cancer cells; (4) inhibiting cancer cell metastasis; or (5) inhibiting angiogenesis.

In some embodiments, the compound of the invention is administered as first line therapy. In other embodiments, the compound of the invention is administered as second (or later) line therapy.

Dosage Forms and Regimens

Administration of the compounds of the invention may be affected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra patient dose escalation as determined by the skilled artisan. Determining appropriate dosages and regimens for administration of the chemotherapeutic agent are well known in the relevant art and would be understood to be encompassed by the skilled artisan once provided the teachings disclosed herein.

The amount of the compound of the invention administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Formulations and Routes of Administration

As used herein, a "pharmaceutically acceptable carrier" refers to a carrier or diluent that does not cause significant irritation to an organism and does not abrogate the biological activity and properties of the administered compound.

The pharmaceutical acceptable carrier may comprise any conventional pharmaceutical carrier or excipient. The choice of carrier and/or excipient will to a large extent depend on factors such as the particular mode of administration, the effect of the carrier or excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulations, solution suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid filled), chews, multi and nano particulates, gels, solid solution, liposome, films (including muco adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast dissolving, fast disintegrating dosage forms such as those described in Expert Opinion in Therapeutic Patents, 11 (6), 981 986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet, dry, or melt granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0 8247 6918 X), the disclosure of which is incorporated herein by reference in its entirety.

Solid formulations for oral administration may be formulated to be immediate and/or modified release. Modified release formulations include delayed, sustained pulsed, controlled, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On line, 25(2), 1 14 (2001). The use of chewing gum to achieve controlled release is described in WO 00/35298. The disclosures of these references are incorporated herein by reference in their entireties.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non aqueous solution or as a dried form to be used in conjunction with a suitable vehicle such as sterile, pyrogen free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility enhancing agents.

Formulations for parenteral administration may be formulated to be immediate and/or modified release. Modified release formulations include delayed, sustained, pulsed, controlled, targeted and programmed release. Thus, compounds of the invention may be formulated as a solid, semi solid, or thixotropic liquid for administration as an implanted depot providing modified release of the active compound. Examples of such formulations include drug coated stents and PGLA microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955 958 by Finnin and Morgan (October 1999). Other means of topical administration include delivery by electroporation, iontophoresis, phonophoresis, sonophoresis and micro needle or needle free (e.g. Powderject™, Bioject™, etc.) injection. The disclosures of these references are incorporated herein by reference in their entireties.

Formulations for topical administration may be formulated to be immediate and/or modified release. Modified release formulations include delayed, sustained, pulsed, controlled, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2 tetrafluoroethane or 1,1,1,2,3,3,3 heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as I leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL lactic coglycolic acid (PGLA). Modified release formulations include delayed, sustained, pulsed, controlled, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed, sustained, pulsed, controlled, targeted and programmed release.

Compounds of the invention may also be administered directly to the eye or ear, typically in the form of drops of a micronized suspension or solution in isotonic, pH adjusted, sterile saline. Other formulations suitable for ocular and aural administration include ointments, biodegradable (e.g. absorbable gel sponges, collagen) and non biodegradable (e.g. silicone) implants, wafers, lenses and particulate or vesicular systems, such as niosomes or liposomes. A polymer such as crossed linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed, sustained, pulsed, controlled, targeted, or programmed release.

Other Technologies

Compounds of the invention may be combined with soluble macromolecular entities, such as cyclodextrin and suitable derivatives thereof or polyethylene glycol containing polymers, in order to improve their solubility, dissolution rate, taste masking, bioavailability and/or stability for use in any of the aforementioned modes of administration.

Drug cyclodextrin complexes, for example, are found to be generally useful for most dosage forms and administration routes. Both inclusion and non inclusion complexes may be used. As an alternative to direct complexation with the drug, the cyclodextrin may be used as an auxiliary additive, i.e. as a carrier, diluent, or solubilizer. Most commonly used for these purposes are alpha, beta and gamma cyclodextrins, examples of which may be found in PCT Publication Nos. WO 91/11172, WO 94/02518 and WO 98/55148, the disclosures of which are incorporated herein by reference in their entireties.

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, and frequently about 0.01 to about 35 mg/kg/day, in single or divided doses. For a 70 kg human, this would amount to about 0.07 mg/day to about 7000 mg/day, more commonly, from about 10 mg/day to about 1000 mg/day. Sometimes, the dosage is about 10, 20, 30, 40, 50, 60, 75, 100, 125, 150, 175, 200, 225, 250, 275, 300, 325, 350, 375, 400, 425, 450, 475, 500, 525, 550, 575, 600, 625, 650, 675, 700, 750, 800, 900 or 1000 mg/day. Sometimes, the dosage is from about 10 mg/day to about 1000 mg/day, from about 10 mg/day to about 750 mg/day, from about 10 mg/day to about 600 mg/day, from about 10 mg/day to about 300 mg/day, from about 10 mg/day to about 150 mg/day, from about 20 mg/day to about 750 mg/day, from about 20 mg/day to about to 600 mg/day, from about 20 mg/day to about to 300 mg/day, from about 20 mg/day to about to 150 mg/day, from about 50 mg/day to about 750 mg/day, from about 50 mg/day to about 600 mg/day, from about 50 mg/day to about 300 mg/day, from about 50 mg/day to about 150 mg/day, from about 75 mg/day to about 750 mg/day, from about 75 mg/day to about 600 mg/day, from about 75 mg/day to about 300 mg/day, or from about 75 mg/day to about 150 mg/day.

In some instances, dosage levels below the lower limit of the aforesaid range may be more than adequate, while in other cases still larger doses may be used without causing any harmful side effect, with such larger doses typically divided into several smaller doses for administration throughout the day.

Kit of Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for co-administration of the compositions. Thus, the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

Combination Therapy

As used herein, the term "combination therapy" refers to the administration of a compound of the invention together with an at least one additional pharmaceutical or medicinal agent (e.g., an anti-cancer therapeutic agent), either sequentially or simultaneously.

As noted herein, the compounds of the invention may be used in combination with one or more additional anti-cancer therapeutic agent. The efficacy of the compounds of the invention in certain tumors may be enhanced by combination with other approved or experimental cancer therapies, e.g., radiation, surgery, chemotherapeutic agents, targeted therapies, agents that inhibit other signaling pathways that are dysregulated in tumors, and other immune enhancing agents, such as PD 1 or PD L1 antagonists and the like.

When a combination therapy is used, the one or more additional anti-cancer therapeutic agents may be administered sequentially or simultaneously with the compound of the invention. In one embodiment, the additional anti-cancer therapeutic agent is administered to a mammal (e.g., a human) prior to administration of the compound of the invention. In another embodiment, the additional anti-cancer therapeutic agent is administered to the mammal after administration of the compound of the invention. In another embodiment, the additional anti-cancer therapeutic agent is administered to the mammal (e.g., a human) simultaneously with the administration of the compound of the invention.

The invention also relates to a pharmaceutical composition for the treatment of abnormal cell growth in a mammal, including a human, which comprises an amount of a compound of the invention, as defined above (including hydrates, solvates and polymorphs of said compound or pharmaceutically acceptable salts thereof), in combination with one or more (preferably one to three) additional anti-cancer therapeutic agents.

Classes of additional chemotherapeutic agents, which can be administered in combination with a compound of this invention, include, but are not limited to: alkylating agents, antimetabolites, kinase inhibitors, spindle poison plant alkaloids, cytotoxic/antitumor antibiotics, topisomerase inhibitors, photosensitizers, anti-estrogens and selective estrogen receptor modulators (SERMs), anti-progesterones, estrogen receptor down-regulators (ERDs), estrogen receptor antagonists, leutinizing hormone-releasing hormone agonists; IL-2 receptor agonist (recombinant cytokines or agonists for cytokine receptors); and anti-sense oligonucleotides or oligonucleotides derivatives that inhibit expression of genes implicated in abnormal cell proliferation or tumor growth.

Other additional chemotherapy agents include not only taxanes or platinum agents but also HER2 targeted agents, e.g., trastuzumab.

In another embodiment, such additional anti-cancer therapeutic agents include compounds derived from the following classes: mitotic inhibitors, alkylating agents, antimetabolites, antitumor antibiotics, anti-angiogenesis agents, topoisomerase I and II inhibitors, plant alkaloids, spindle poison plant alkaloids, KRAS inhibitors; MCT4 inhibitors; MAT2a inhibitors; alk/c-Met/ROS inhibitors (including crizotinib or lorlatinib); mTOR inhibitors (including temsirolimus or gedatolisib); src/abl inhibitors (including bosutinib); cyclin-dependent kinase (CDK) inhibitors (including palbociclib, PF-06873600); erb inhibitors (including dacomitinib); PARP inhibitors (including talazoparib); SMO inhibitors (including glasdegib); EGFR T790M inhibitors; PRMT5 inhibitors; TGFβR1 inhibitors; growth factor inhibitors; cell cycle inhibitors, biological response modifiers; enzyme inhibitors; and cytotoxics.

In another embodiment, such additional anti-cancer therapeutic agents include compounds derived from an anti-angiogenesis agent, including for example tyrosine kinase/vascular endothelial growth factor (VEGF) receptor (VEGFR) inhibitors (including sunitinib, axitinib, sorafenib, and tivozanib), TIE-2 inhibitors, PDGFR inhibitors, angiopoetin inhibitors, PKCβ inhibitors, COX-2 (cyclooxygenase II) inhibitors, integrins (alpha-v/beta-3), MMP-2 (matrix-metalloproteinase 2) inhibitors, and MMP-9 (matrix-metalloproteinase 9) inhibitors. Preferred anti-angiogenesis agents include sunitinib (Sutent™), bevacizumab (Avastin™), axitinib (Inlyta™) SU 14813 (Pfizer), and AG 13958 (Pfizer). Additional anti-angiogenesis agents include vatalanib (CGP 79787), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™ (AE 941), tetrathiomolybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer). Other anti-angiogenesis agents include enzastaurin (LY 317615), midostaurin (CGP 41251), perifosine (KRX 0401), teprenone (Selbex™) and UCN 01 (Kyowa Hakko). Other examples of anti-angiogenesis agents include celecoxib (Celebrex™), parecoxib (Dynastat™), deracoxib (SC 59046), lumiracoxib (Preige™), valdecoxib (Bextra™), rofecoxib (Vioxx™), iguratimod (Careram™), IP 751 (Invedus), SC-58125 (Pharmacia) and etoricoxib (Arcoxia™). Yet further anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™, Naprosyn™), diclofenac (Voltaren™), indomethacin (Indocin™) sulindac (Clinoril™), tolmetin (Tolectin™), etodolac (Lodine™), ketorolac (Toradol™), and oxaprozin (Daypro™). Yet further anti-angiogenesis agents include ABT 510 (Abbott), apratastat (TMI 005), AZD 8955 (AstraZeneca), incyclinide (Metastat™), and PCK 3145 (Procyon). Yet further anti-angiogenesis agents include acitretin (Neotigason™), plitidepsin (aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™), squalamine (EVIZON™) thalidomide (Thalomid™), Ukrain™ (NSC 631570), Vitaxin™ (MEDI 522), and zoledronic acid (Zometa™).

In another embodiment, such additional anti-cancer therapeutic agents include compounds derived from hormonal agents and antagonists. Examples include where anti-hormonal agents act to regulate or inhibit hormone action on tumors such as anti-estrogens and selective estrogen receptor modulators (SERMs), and a selective estrogen receptor degrader (SERD) including tamoxifen, raloxifene, droloxifene, 4-hydroxytamoxifen, trioxifene, keoxifene, LY117018, onapristone, toremifene (Fareston), and fulvestrant. Examples also include aromatase inhibitors that inhibit the enzyme aromatase, which regulates estrogen production in the adrenal glands, and include compounds like 4(5)-imidazoles, aminoglutethimide, megestrol acetate, exemestane, formestane, fadrozole, vorozole, letrozole, and anastrozole; and anti-androgens such as flutamide, nilutamide, bicalutamide, leuprolide, fluridil, apalutamide, enzalutamide, cimetidine and goserelin.

In another embodiment, such additional anti-cancer therapeutic agents include compounds derived from signal transduction inhibitors, such as inhibitors of protein tyrosine kinases and/or serine/threonine kinases: a signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EGF inhibitor, ErbB-1 (EGFR), ErbB-2, pan erb, IGF1R inhibitors, MEK (including binimetinib (Mektovi™)), c-Kit inhibitors, FLT-3 inhibitors, K-Ras inhibitors, PI3 kinase inhibitors, JAK inhibitors, STAT inhibitors, Raf kinase inhibitors, BRAF (including encorafenib (Braftovi™)), Akt inhibitors, mTOR inhibitor, P70S6 kinase inhibitors, inhibitors of the WNT pathway and multi-targeted kinase inhibitors.

In another embodiment, such additional anti-cancer therapeutic agents include docetaxel, paclitaxel, paclitaxel protein-bound particles, cisplatin, carboplatin, oxaliplatin, capecitabine, gemcitabine or vinorelbine.

In another embodiment, such additional anti-cancer therapeutic agents include compounds derived from an epigenetic modulator, where examples include an inhibitor of EZH2 (including PF-06821497), SMARCA4, PBRM1, ARID1A, ARID2, ARID1B, DNMT3A, TET2, MLL1/2/3, NSD1/2, SETD2, BRD4, DOT1L, HKMTsanti, PRMT1-9, LSD1, UTX, IDH1/2 or BCL6.

In another embodiment, such additional anti-cancer therapeutic agents include compounds that are immuno-oncology agents, including immunomodulatory agents.

In another embodiment, combinations with pattern recognition receptors (PRRs) are contemplated. PRRs are receptors that are expressed by cells of the immune system and that recognize a variety of molecules associated with pathogens and/or cell damage or death. PRRs are involved in both the innate immune response and the adaptive immune response. PRR agonists may be used to stimulate the immune response in a subject. There are multiple classes of PRR molecules, including toll-like receptors (TLRs), RIG-I-like receptors (RLRs), nucleotide-binding oligomerization domain (NOD)-like receptors (NLRs), C-type lectin receptors (CLRs), and Stimulator of Interferon Genes (STING) protein.

The STING protein functions as both a cytosolic DNA sensor and an adaptor protein in Type 1 interferon signaling. The terms "STING" and "stimulator of interferon genes" refer to any form of the STING protein, as well as variants, isoforms, and species homologs that retain at least a part of the activity of STING. Unless indicated differently, such as by specific reference to human STING, STING includes all mammalian species of native sequence STING, e.g. human, monkey, and mouse STING is also known as—TMEM173.

"STING agonist" as used herein means, any molecule, which upon binding to STING, (1) stimulates or activates STING, (2) enhances, increases, promotes, induces, or prolongs an activity, function, or presence of STING, or (3) enhances, increases, promotes, or induces the expression of STING. STING agonists useful in the any of the treatment method, medicaments and uses of the present invention include, for example, nucleic acid ligands which bind STING.

Examples of STING agonists that are useful in the treatment methods, medicaments, and uses of the present invention include various immunostimulatory nucleic acids, such as synthetic double stranded DNA, cyclic di-GMP, cyclic-GMP-AMP (cGAMP), synthetic cyclic dinucleotides (CDN) such as MK-1454 and ADU-S100 (MIW815), and small molecules such as WO2019027858, WO20180093964, WO2017175156, WO2017175147.

Therapeutic antibodies may have specificity against a variety of different antigens. For example, therapeutic antibodies may be directed to a tumor associated-antigen, such that binding of the antibody to the antigen promotes death of the cell expressing the antigen. In other example, therapeutic antibodies may be directed to an antigen on an immune cell, such that binding of the antibody prevents downregulation of the activity of the cell expressing the antigen (and thereby promotes activity of the cell expressing the antigen). In some situations, a therapeutic antibody may function through multiple different mechanisms (for example, it may both i) promote death of the cell expressing the antigen, and ii) prevent the antigen from causing down-regulation of the activity of immune cells in contact with the cell expressing the antigen).

In another embodiment, such additional anti-cancer therapeutic agents include antibodies that would be blocking or inhibitory at the target: CTLA-4 (including ipilimumab or tremelimumab), PD-1 or PD-L1 (including atezolizumab, avelumab, cemiplimab, durvalumab, nivolumab, or pembrolizumab), LAG-3, TIM-3, or TIGIT.

In another embodiment, such additional anti-cancer therapeutic agents include antibodies that are agonists of 4-1BB, OX40, GITR, ICOS, or CD40.

In another embodiment the anti-cancer therapy may be a CAR-T-cell therapy.

Examples of a therapeutic antibody include: an anti-OX40 antibody, an anti-4-1BB antibody, an anti-HER2 antibody (including an anti-HER2 antibody-drug conjugate (ADC)), a bispecific anti-CD47/anti-PD-L1 antibody, and a bispecific anti-P-cadherin/anti-CD3 antibody. Examples of cytotoxic agents that may be incorporated in an ADC include an anthracycline, an auristatin, a dolastatin, a combretastatin, a duocarmycin, a pyrrolobenzodiazepine dimer, an indolinobenzodiazepine dimer, an enediyne, a geldanamycin, a maytansine, a puromycin, a taxane, a vinca alkaloid, a camptothecin, a tubulysin, a hemiasterlin, a spliceostatin, a pladienolide, and stereoisomers, isosteres, analogs, or derivatives thereof. Exemplary immunomodulating agents that may be incorporated in an ADC include gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, cytokines, stem cell growth factors, lymphotoxins, tumor necrosis factor (TNF), hematopoietic factors, interleukins (e.g., interleukin-1 (IL-1), IL-2, IL-3, IL-6, IL-10, IL-12, IL-15, IL-18, and IL-21), colony stimulating factors (e.g., granulocyte-colony stimulating factor (G-CSF) and granulocyte macrophage-colony stimulating factor (GM-CSF)), interferons (e.g., interferons-.alpha., -.beta. and -.gamma), the stem cell growth factor designated "S 1 factor," erythropoietin and thrombopoietin, or a combination thereof.

Additional examples of therapeutic antibodies may include the following antigens where exemplary antibodies directed to the antigen are also included below (in brackets/parenthesis after the antigen). The antigens as follow may also be referred to as "target antigens" or the like herein. Target antigens for therapeutic antibodies herein include, for example: 4-1BB (e.g. utomilumab); 5T4; A33; alpha-folate receptor 1 (e.g. mirvetuximab soravtansine); Alk-1; BCMA [e.g. see U.S. Pat. No. 9,969,809]; BTN1A1 (e.g. see WO2018222689); CA-125 (e.g. abagovomab); Carboanhydrase IX; CCR2; CCR4 (e.g. mogamulizumab); CCR5 (e.g. leronlimab); CCR8; CD3 [e.g. blinatumomab (CD3/CD19 bispecific), CD3/P-cadherin bispecific, CD3/BCMA bispecific] CD19 (e.g. blinatumomab, MOR208); CD20 (e.g. ibritumomab tiuxetan, obinutuzumab, ofatumumab, rituximab, ublituximab); CD22 (inotuzumab ozogamicin, moxetumomab pasudotox); CD25; CD28; CD30 (e.g. brentuximab vedotin); CD33 (e.g. gemtuzumab ozogamicin); CD38 (e.g. daratumumab, isatuximab), CD40; CD-40L; CD44v6; CD47 (e.g. Hu5F9-G4, CC-90002, SRF231, B6H12); CD52 (e.g. alemtuzumab); CD56; CD63; CD79 (e.g. polatuzumab vedotin); CD80; CD123; CD276/B7-H3 (e.g. omburtamab); CDH17; CEA; ClhCG; CTLA-4 (e.g. ipilimumab, tremelimumab), CXCR4; desmoglein 4; DLL3 (e.g. rovalpituzumab tesirine); DLL4; E-cadherin; EDA; EDB; EFNA4; EGFR (e.g. cetuximab, depatuxizumab mafodotin, necitumumab, panitumumab); EGFRvIII; Endosialin; EpCAM (e.g. oportuzumab monatox); FAP; Fetal Acetylcholine Receptor; FLT3 (e.g. see WO2018/220584); GD2 (e.g. dinutuximab, 3F8); GD3; GITR; GloboH; GM1; GM2; HER2/neu [e.g. margetuximab, pertuzumab, trastuzumab; ado-trastuzumab emtansine, trastuzumab duocarmazine, [see U.S. Pat. No. 8,828,401]; HER3; HER4; ICOS; IL-10; ITG-AvB6; LAG-3 (e.g. relatlimab); Lewis-Y; LG; Ly-6; M-CSF [see U.S. Pat. No. 7,326,414]; MCSP; mesothelin; MUC1; MUC2; MUC3; MUC4; MUC5AC; MUC5B; MUC7; MUC16; Notch1; Notch3; Nectin-4 (e.g. enfortumab vedotin); OX40 [see U.S. Pat. No. 7,960,515]; P-Cadherin [see WO2016/001810]; PCDHB2; PDGFRA (e.g. olaratumab); Plasma Cell Antigen; PolySA; PSCA; PSMA; PTK7 [see U.S. Pat. No. 9,409,995]; Ror1; SAS; SCRx6; SLAMF7 (e.g. elotuzumab); SHH; SIRPa (e.g. ED9, EffiDEM); STEAP; TGF-beta; TIGIT; TIM-3; TMPRSS3; TNF-alpha precursor; TROP-2 (e.g sacituzumab govitecan); TSPAN8; VEGF (e.g. bevacizumab, brolucizumab); VEGFR1 (e.g. ranibizumab); VEGFR2 (e.g. ramucirumab, ranibizumab); Wue-1.

Exemplary imaging agents that may be included in an ADC include fluorescein, rhodamine, lanthanide phosphors, and their derivatives thereof, or a radioisotope bound to a chelator. Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5,-TAMRA), tetramethylrhodamine (TMR), and sulforhodamine (SR) (e.g., SR101). Examples of chelators include, but are not limited to, 1,4,7,10-tetraazacyclododecane-N,N',N'',N'''-tetraacetic acid (DOTA), 1,4,7-triazacyclononane-1,4,7-triacetic acid (NOTA), 1,4,7-triazacyclononane, 1-glutaric acid-4,7-acetic acid (deferoxamine), diethylenetriaminepentaacetic acid (DTPA), and 1,2-bis(o-aminophenoxy)ethane-N,N,N',N'-tetraacetic acid) (BAPTA).

Exemplary therapeutic proteins that may be included in an ADC include a toxin, a hormone, an enzyme, and a growth factor.

Exemplary biocompatible polymers that may be incorporated in an ADC include water-soluble polymers, such as polyethylene glycol (PEG) or its derivatives thereof and zwitterion-containing biocompatible polymers (e.g., a phosphorylcholine containing polymer).

Exemplary biocompatible polymers that may be incorporated in an ADC include anti-sense oligonucleotides.

The invention also concerns the use of radiation in combination with any anti-cancer therapeutic agent administered herein. More specifically, compounds of the invention can be administered in combination with additional therapies, such as radiation therapy and/or chemotherapy.

Chemical Synthesis

The following schemes and written descriptions provide general details regarding the preparation of the compounds of the invention.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of Formula (I), and compounds that fall within Formula (I), e.g., compounds of Formulas (I), (Ia) or (Ib), and the like.

In addition, the skilled person will appreciate that it may be necessary or desirable at any stage in the synthesis of compounds of the invention to protect one or more sensitive groups, to prevent undesirable side reactions. In particular, it may be necessary or desirable to protect amino or alcohol groups. The protecting groups (PGs) used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 2 ("Protection for the Hydroxyl Group, Including 1,2- and 1,3-Diols"), incorporated herein by reference, which also describes methods for the removal of such groups.

All of the derivatives of Formula (I) can be prepared by the procedures described in the general methods presented below or by routine modifications thereof. The present invention also encompasses any one or more of these processes for preparing the derivatives of Formula (I), in addition to any novel intermediates used therein. The person skilled in the art will appreciate that the following reactions may be heated thermally or under microwave irradiation or under flow chemistry conditions.

It will be further appreciated that it may be necessary or desirable to carry out the transformations in a different order from that described in the schemes, or to modify one or more of the transformations, to provide the desired compound of the invention.

According to a first process, compounds of Formula (I) may be prepared from compounds of intermediate (i) as illustrated by Scheme 1.

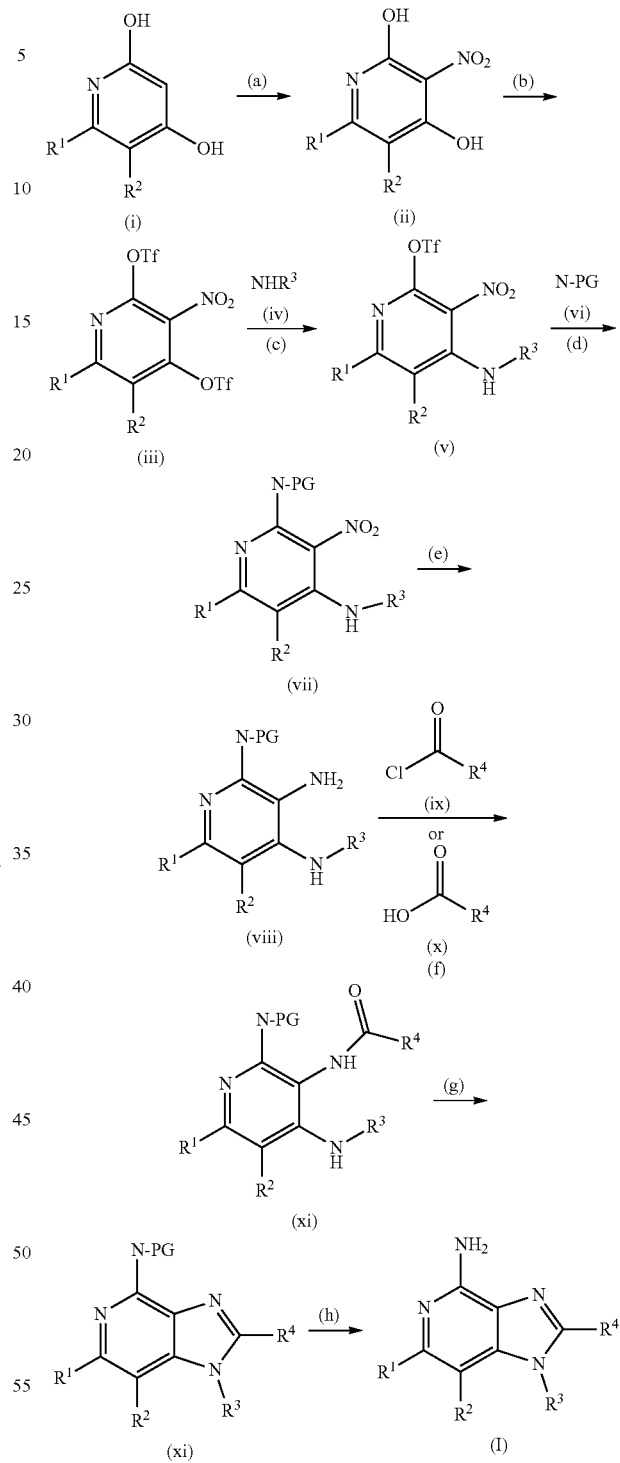

Scheme 1

Possible PGs include 4-methoxybenzyl, N,N-bis-(4-methoxybenzyl), tert-octyl or other suitable amine protecting group; N,N-bis-(4-methoxybenzyl) has been used most frequently for compounds of Formula (I).

Intermediates (i), (iv), (vi), (ix), (x) are commercially available or may be synthesized by those of ordinary skill in the art according to the literature or preparations described herein. For the Schemes discussed herein, when compounds of Formula (I) have chiral centers, the respective enantiomers may be separated via chiral separation of the racemate as required. Also, when R³ contains a protecting group such as a ketal or silyl, suitable deprotection conditions may be employed as necessary, such as methanesulfonic acid in dichloromethane/methanol/water.

Intermediate (ii) may be prepared from intermediate (i) according to step (a), a nitration reaction. Typical methods employ use of a suitable nitrating agent and suitable organic or inorganic solvent. Preferred conditions comprise use of nitric acid in sulfuric acid at 10° C.

Intermediate (iii) may be prepared from intermediate (ii) according to step (b), a triflate forming reaction. Typical methods employ use of trifluoromethanesulfonic anhydride with a suitable organic or inorganic base in a suitable organic solvent at reduced temperatures. Preferred conditions comprise use of triethylamine in dichloroethane at 0° C.

Intermediate (v) may be prepared from intermediate (iii) according to step (c), a nucleophilic aromatic substitution reaction with intermediate (iv). Typical methods employ use of a suitable organic or inorganic base in a suitable organic solvent at RT or elevated temperatures either thermally, under microwave irradiation, or flow chemistry conditions. Preferred conditions comprise use of triethylamine in dichloroethane.

Intermediate (vii) may be prepared from intermediate (v) according to step (d), a nucleophilic aromatic substitution reaction with intermediate (vi). Typical methods employ use of a suitable organic or inorganic base in a suitable organic solvent at RT or elevated temperatures either thermally, under microwave irradiation, or flow chemistry conditions. For example, use of Bis(4-methoxybenzyl)amine with triethylamine in dichloroethane at 50° C. heated thermally or use of tert-Octylamine with triethylamine in toluene at 75° C.

Intermediate (viii) may be prepared from intermediate (vii) according to step (e), a nitro reduction step. Typical methods employ hydrogenation conditions with a suitable hydrogen source and suitable hydrogenation catalyst in a suitable organic solvent at RT or at elevated temperatures heated thermally, under microwave irradiation, or flow chemistry conditions or use of a suitable metal and suitable hydrogen or proton donor in a suitable organic solvent. Preferred conditions comprise use of zinc dust and ammonium formate in methanol.

Intermediate (xi) may be prepared from intermediate (viii) according to step (f), an amide bond forming step with intermediate (ix) or (x). Typical methods employ use of intermediate (ix) with a suitable organic or inorganic base in a suitable organic solvent or use of intermediate (x) with a suitable amide coupling reagent and a suitable organic or inorganic base in a suitable organic solvent. Typical conditions use triethylamine and dichloromethane when using intermediate (ix). Typical conditions use 50 wt % propylphosphonic acid anhydride solution in ethylacetate, triethylamine and ethyl acetate when using intermediate (x).

Intermediate (xii) may be prepared from intermediate (xi) according to step (g), an imidazole ring formation. Typical methods employ basic conditions utilizing a suitable organic or inorganic base at elevated temperatures either thermally or under microwave irradiation or flow chemistry conditions; alternatively, acidic conditions utilizing a suitable organic or inorganic acid at elevated temperatures either thermally or under microwave irradiation or flow chemistry conditions. Alternatively, a suitable dehydrating agent in a suitable organic solvent at elevated temperatures either thermally or under microwave irradiation or flow chemistry conditions. Preferred conditions comprise use of sodium hydroxide in ethanol at 80° C. heated thermally or triphenylphosphine and triethylamine in carbon tetrachloride at 80° C. heated thermally.

Compounds of Formula (I) may be prepared from intermediate (xii) according to step (h), a removal of PG and those contained in R³ if present, eg. silyl or ketal. Typical deprotection methods comprise a suitable organic or inorganic acid in a suitable organic solvent at RT or at elevated temperatures either thermally or under microwave irradiation or flow chemistry conditions. Preferred conditions comprise methanesulfonic acid in dichloromethane at 45° C. heated thermally followed by addition of methanol and water.

Alternatively, compounds of Formula (I) may be prepared from intermediate (iii), as illustrated by Scheme 2.

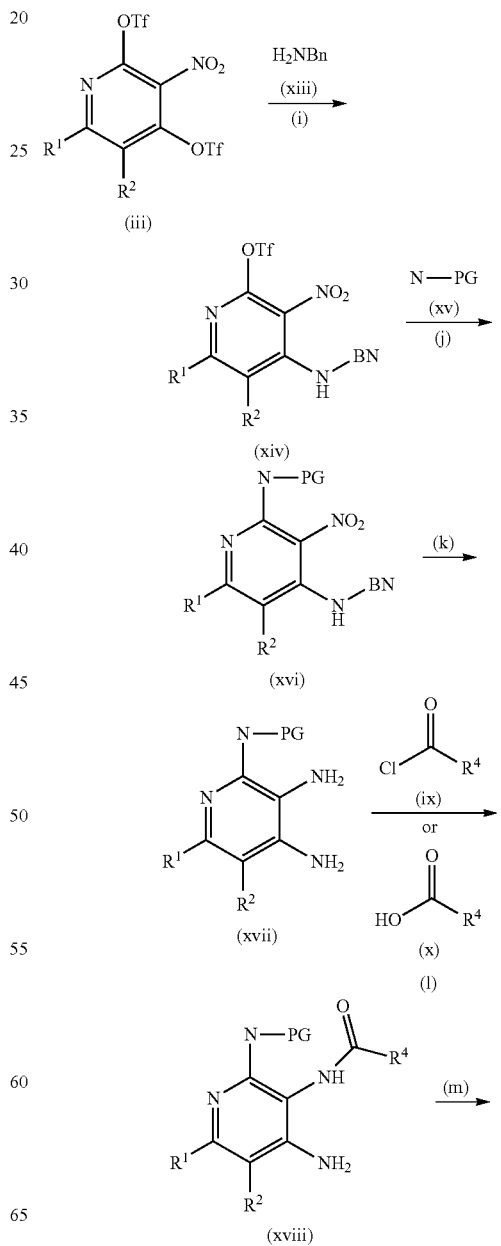

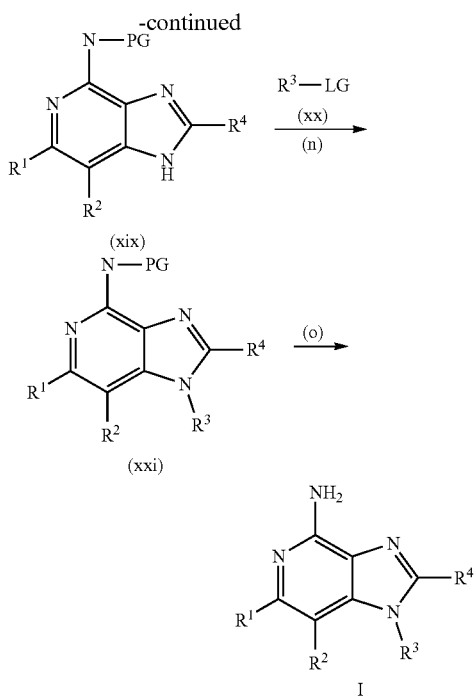

Possible amino PGs include 4-methoxybenzyl, N,N-bis (4-methoxybenzyl), tert-octyl, with tert-octyl being used most frequently in the examples.

A leaving group (LG) is a functional group to assist with a specific reaction and includes OH, Cl, Br, I, OMs, OTs, and OTf, with OH being used most frequently in the examples.

Intermediates (ix), (x), (xiii), (xv) are commercially available or may be synthesized by those skilled in the art according to the literature or preparations described herein.

Intermediate (xiv) may be prepared from intermediate (iii) according to step (i), a nucleophilic aromatic substitution reaction with intermediate (xiii). Typical methods employ use of a suitable organic or inorganic base in a suitable organic solvent at RT or elevated temperatures either thermally, under microwave irradiation, or flow chemistry conditions. Preferred conditions comprise use of triethylamine in dichloroethane.

Intermediate (xvi) may be prepared from intermediate (xiv) according to step (j), a nucleophilic aromatic substitution reaction with intermediate (xv). Typical methods employ use of a suitable organic or inorganic base in a suitable organic solvent at RT or elevated temperatures either thermally, under microwave irradiation, or flow chemistry conditions. Preferred conditions comprise use of bis (4-methoxybenzyl)amine with triethylamine in dichloroethane at 50° C. heated thermally or use of tert-Octylamine with triethylamine in toluene at 75° C.

Intermediate (xvii) may be prepared from intermediate (xvi) according to step (k), a tandem nitro reduction and debenzylation step. Typical methods employ hydrogenation conditions with a suitable hydrogen source and suitable hydrogenation catalyst in a suitable organic solvent at RT or at elevated temperatures heated thermally, under microwave irradiation, or flow chemistry conditions. Preferred conditions comprise use of ammonium formate and 30% palladium on carbon in ethanol at 55° C.

Intermediate (xviii) may be prepared from intermediate (xvii) according to step (I), an amide bond forming step with intermediate (ix) or (x). Typical methods employ use of intermediate (ix) with a suitable organic or inorganic base in a suitable organic solvent or use of intermediate (x) with a suitable amide coupling reagent and a suitable organic or inorganic base in a suitable organic solvent. Preferred conditions comprise use of intermediate (ix) with triethylamine and dichloromethane at 0° C.

Intermediate (xix) may be prepared from intermediate (xviii) according to step (m), an imidazole ring formation. Typical methods employ basic conditions utilizing a suitable organic or inorganic base at elevated temperatures either thermally, under microwave irradiation, or flow chemistry conditions; acidic conditions utilizing a suitable organic or inorganic acid at elevated temperatures either thermally, under microwave irradiation, or flow chemistry conditions, or a suitable dehydrating agent in a suitable organic solvent at elevated temperatures either thermally, under microwave irradiation, or flow chemistry conditions. Preferred conditions comprise use of sodium hydroxide in ethanol at 75° C. heated thermally Intermediate (xxi) may be prepared from intermediate (xix) according to step (n), a nucleophilic substitution reaction or Mitsunobu reaction with intermediate (xx). Typical methods comprise a suitable organic or inorganic base in a suitable organic solvent at RT or elevated temperatures either thermally, under microwave irradiation, or flow chemistry conditions. Alternatively, when LG is a hydroxyl group by treatment with a suitable phosphine and suitable azodicarboxylate (or combination of both in a single reagent) in a suitable organic solvent at RT or elevated temperatures either thermally, under microwave irradiation, or flow chemistry conditions. Preferred conditions, where LG is a hydroxyl group, comprise use of cyanomethylenetributylphosphorane in toluene at 90° C. or 100° C. heated thermally.

Compounds of Formula (I) may be prepared from intermediate (xxi) according to step (o), a removal of PG and any PG contained in $R^3$ if present, for example a ketal or silane. Typical methods comprise a suitable organic or inorganic acid in a suitable organic solvent at RT or at elevated temperatures either thermally, under microwave irradiation, or flow chemistry conditions. Preferred conditions comprise methanesulfonic acid in hexafluoroisopropanol or trifluoroacetic acid in dichloromethane followed by addition of methanol.

In executing the synthesis of the compounds of the invention, one skilled in the art will monitor reactions with common methods that include thin-layer chromatography (TLC), liquid chromatography/mass spectroscopy (LCMS), and nuclear magnetic resonance (NMR).

One skilled in the art will also recognize that the compounds of the invention may be prepared as mixtures of diastereomers or geometric isomers (e.g., cis and trans substitution on a cycloalkane ring). These isomers can be separated by standard chromatographic techniques, such as normal phase chromatography on silica gel, reverse phase preparative high pressure liquid chromatography or supercritical fluid chromatography. One skilled in the art will also recognize that some compounds of the invention are chiral and thus may be prepared as racemic or scalemic mixtures of enantiomers. Several methods are available and are well known to those skilled in the art for the separation of enantiomers.

EXAMPLES

Except where otherwise noted, reactions were run under an atmosphere of nitrogen. Chromatography on silica gel was carried out using 250-400 mesh silica gel using pressurized nitrogen (~10-15 psi) to drive solvent through the column ("flash chromatography"). Where indicated, solutions and reaction mixtures were concentrated by rotary evaporation under vacuum.

$^1$H and $^{19}$F Nuclear magnetic resonance (NMR) spectra were in all cases consistent with the proposed structures. Characteristic chemical shifts (δ) are given in parts-per-million downfield from tetramethylsilane (for $^1$H-NMR) using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; d$_6$-DMSO, deuterodimethylsulfoxide; and CD$_3$OD, deuteromethanol. Where appropriate, tautomers may be recorded within the NMR data; and some exchangeable protons may not be visible.

Mass spectra, MS (m/z), were recorded using either electrospray ionization (ESI) or atmospheric pressure chemical ionization (APCI). Where relevant and unless otherwise stated, the m/z data provided are for isotopes $^{19}$F, $^{35}$Cl, $^{79}$Br and $^{127}$I.

The nomenclature is written as described by IUPAC (International Union of Pure and Applied Chemistry generated within Perkin Elmers Chemdraw 18.0.

In the non-limiting Examples and Preparations that are set out herein, the following the abbreviations apply:

AcOH is acetic acid;
aq is aqueous;
Bn is benzyl;
br is broad;
tBu is tert-butyl;
° C. is degrees Celsius;
CO$_2$ is carbon dioxide;
CMBP is Cyanomethylenetributylphosphorane;
Cs$_2$CO$_3$ is cesium carbonate;
DCE is dichloroethane;
DCM is dichloromethane; methylene chloride;
DIPEA/DIEA is N-ethyldiisopropylamine, N,N-diisopropylethylamine;
DMA is dimethylacetamide;
DMF is N,N-dimethylformamide;
DMSO is dimethyl sulphoxide;
ee is enantiomeric excess;
EtOAc is ethyl acetate;
EtOH is ethanol;
Et$_3$N is triethylamine;
g is gram;
HCO$_2$NH$_4$ is ammonium formate;
HCl is hydrochloric acid;
HFIP is 1,1,1,3,3,3-hexafluoroisopropanol;
HNO$_3$ is nitric acid;
HPLC is high pressure liquid chromatography;
H$_2$O is water;
H$_2$SO$_4$ is sulfuric acid;
Hr or hr is hour;
IPA/iPrOH is isopropanol;
L is litre;
LCMS is liquid chromatography mass spectrometry;
LiAlH$_4$ is lithium aluminium hydride;
LiOH is lithium hydroxide;
M is molar;
MeCN is acetonitrile;
MeI is methyl iodide;
MeOH is methanol;
mg is milligram;
MgSO$_4$ is magnesium sulphate;
MHz is mega Hertz;
min is minutes;
mL is milli litre;
mmol is millimole;
mol is mole;
MS m/z is mass spectrum peak;
MsOH is methanesulfonic acid;
NaH is sodium hydride;
NaHCO$_3$ is sodium hydrogencarbonate;
NaOH is sodium hydroxide;
Na$_2$SO$_4$ is sodium sulphate;
NH$_3$ is ammonia;
NH$_4$OH is ammonium hydroxide;
NH(PMB)$_2$ is bis(4-methoxybenzyl)amine;
NMR is nuclear magnetic resonance;
Pd/C is palladium on carbon;
pH is power of hydrogen;
ppm is parts per million;
psi is pounds per square inch;
Rt is retention time;
RT is room temperature;
TBDMS is tertbutyldimethylsilyl;
TBSCl is tertbutylimethylsilyl chloride;
TBME/MTBE is tert-butyl dimethyl ether;
TEA is triethylamine;
Tf$_2$O is trifluoromethanesulfonic anhydride;
TFA is trifluoroacetic acid;
TFAA is trifluoroacetic anhydride;
THF is tetrahydrofuran;
TLC is thin layer chromatography;
TsOH is p-Toluenesulfonic acid;
Zn is zinc;
µL is microlitre;
µmol is micromol Chiral separations were used to separate enantiomers of some intermediates during the preparation of the compounds of the invention. When such separation was done, the separated enantiomers were designated as ENT-1 or ENT-2, according to their order of elution. For compounds with two chiral centers, the stereoisomers at each stereocenter were separated at different times. The designation of ENT-1 or ENT-2 of an intermediate or an example refers to the chiral center for the separation done at that step. It is recognized that when stereoisomers at a chiral center are separated in a compound with two or more centers, the separated enantiomers are diastereomers of each other. The ENT-1 or ENT-2 designation is used herein for consistency and refers to the separated chiral center. By way of example, but not limitation, Examples 6 and 7 have a chiral center. The enantiomers were separated as the last step. The chiral center is drawn as the two possibilities, but it is not known which example is which enantiomer. Therefore, the (R) and (S) designation is not associated with either Example 6 or 7. If the separation occurs on an intermediate in these preparations, after a mixture is subjected to separation procedures, the chiral center is identified with "abs" near that center, with the understanding that the separated enantiomers may not be enantiomerically pure and the specific orientation of that bond is not drawn because the enantiomer was not confirmed. Typically, the enriched enantiomer at each chiral center is >90% of the isolated material. Efforts are also undertaken to enrich the enantiomeric purity at a center to be >98% of the mixture and even >99%.

The optical rotation of an enantiomer can be measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated either by the absence of drawn or described stereochemistry, or by the presence of (+/−) adjacent to the structure; in this latter case, indicated stereochemistry represents the relative (rather than absolute) configuration of the compound's substituents.

Wherein preparative TLC or silica gel chromatography have been used, one skilled in the art may choose any combination of solvents to purify the desired compound.

Example (1): 2-((4-amino-2-(ethoxymethyl)-6,7-dimethyl-1H-imidazo[4,5-c]pyridin-1-yl)methyl)propane-1,3-diol Trifluoroacetate Salt

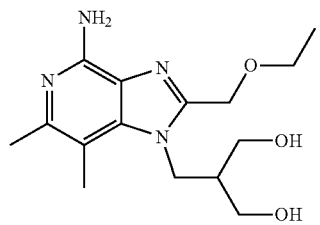 [SMILES: CCOCc1nc2c(N)nc(C)c(C)c2n1CC(CO)CO]

Step 1: Synthesis of 4-(benzylamino)-5,6-dimethyl-3-nitropyridin-2-yl trifluoromethanesulfonate

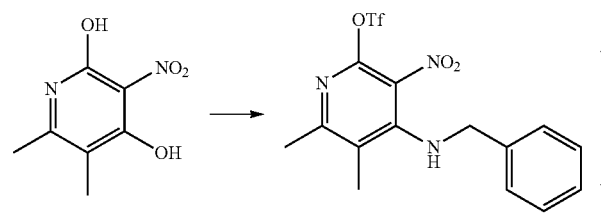

To a round bottom flask under nitrogen was added 5,6-dimethyl-3-nitropyridine-2,4-diol (7.56 g, 41.05 mmol) in dichloromethane (300 ml). To this was added triethylamine (12.5 g, 123 mmol, 17.2 ml) and the reaction cooled to 0° C. Triflic anhydride (23.2 g, 82.1 mmol, 13.8 ml) was added dropwise over 8 min. The reaction was stirred at 0° C. for 1.5 hrs. To this was added benzyl amine (4.84 g, 45.2 mmol, 4.93 ml) and the reaction warmed to RT and stirred for 3 hrs. The reaction mixture was washed with water (2×100 ml) and brine (1×100 ml). The organics were dried over anhydrous sodium sulfate, filtered and concentrated. The residue was purified by silica gel chromatography (Heptane: Ethyl acetate 0-50% gradient) to provide the title compound. Yield: 12.4 g, 30.5 mmol, 74.3%. LCMS m/z 406.2 [M+H]⁺. $^1$H NMR (400 MHz, CDCl$_3$) δ 7.34-7.44; (m, 3H), 7.28-7.31; (m, 2H), 5.24; (br. s., 1H), 4.31; (d, J=5.07 Hz, 2H), 2.47; (s, 3H), 2.12-2.20; (m, 3H).

Step 2: Synthesis of N4-benzyl-5,6-dimethyl-3-nitro-N2-(2,4,4-trimethylpentan-2-yl)pyridine-2,4-diamine

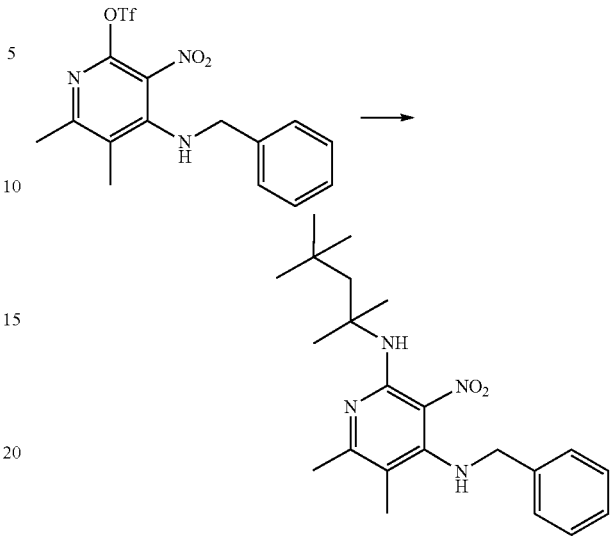

A round bottom flask was charged with added 4-(benzylamino)-5,6-dimethyl-3-nitropyridin-2-yl trifluoromethanesulfonate (12.4 g, 30.5 mmol) and toluene (100 ml). Triethylamine (4.63 g, 45.7 mmol, 6.38 ml) was added followed by tert-Octylamine (5.91 g, 45.7 mmol, 7.34 ml). Reaction was heated at 75° C. for 16 hrs. tert-Octylamine (5.91 g, 45.7 mmol, 7.34 ml) was added and the reaction was heated at 75° C. for 48 hrs. The solution was concentrated on Celite®, and purified by silica gel chromatography (Heptane:Ethyl Acetate 0-50% gradient.) to provide the title compound as a red oil. Yield: 8.93 g, 23.2 mmol, 76.2%. LCMS m/z 386.4 [M+H]⁺. $^1$H NMR (400 MHz, CDCl$_3$) δ 8.76; (s, 1H), 8.38; (br. s., 1H), 7.32-7.39; (m, 2H), 7.27-7.31; (m, J=3.12, 3.12 Hz, 3H), 4.46; (d, J=4.29 Hz, 2H), 2.33; (s, 3H), 2.14; (s, 3H), 1.99; (s, 2H), 1.56; (s, 6H), 0.98; (s, 9H).

Step 3: Synthesis of 5,6-dimethyl-N2-(2,4,4-trimethylpentan-2-yl)pyridine-2,3,4-triamine

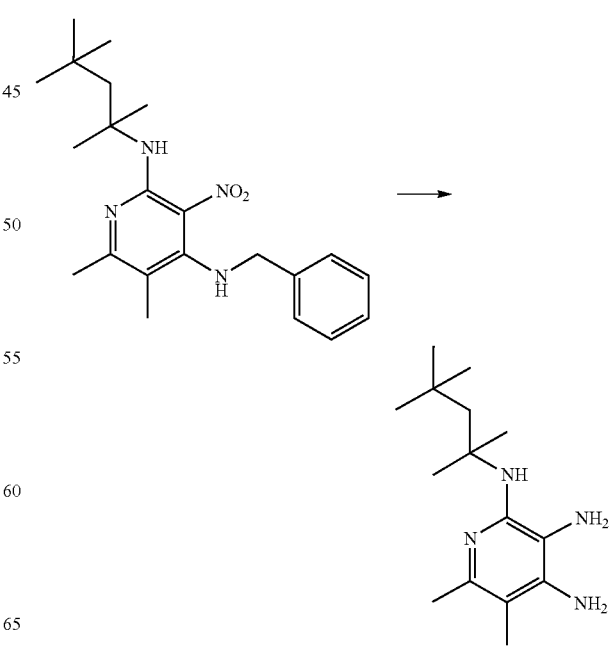

To a round bottom flask with N4-benzyl-5,6-dimethyl-3-nitro-N2-(2,4,4-trimethylpentan-2-yl)pyridine-2,4-diamine (8.90 g, 23.2 mmol) and ethanol (150 ml) was added ammonium formate (14.6 g, 231 mmol). Palladium on carbon (200 mg, 30% Pd) was added and the reaction was stirred at 55° C. for 2 hrs. The reaction mixture was then cooled to RT and filtered through Celite® and the filtrate concentrated. The residue was stirred in ethyl acetate for 1 hr then solids removed by filtration through Celite®. The filtrate was concentrated to provide the title compound as an orange gum. Yield: 5.6 g, 21.2 mmol, 91.5%. LCMS m/z 265.3 [M+H]$^+$. $^1$H NMR (600 MHz, CDCl$_3$) δ 8.62; (s, 1H), 2.40; (s, 3H), 1.98; (s, 3H), 1.66; (s, 2H), 1.29; (s, 6H), 1.05; (s, 9H).

Step 4: Synthesis of 2-(ethoxymethyl)-6,7-dimethyl-N-(2,4,4-trimethylpentan-2-yl)-1H-imidazo[4,5-c]pyridin-4-amine

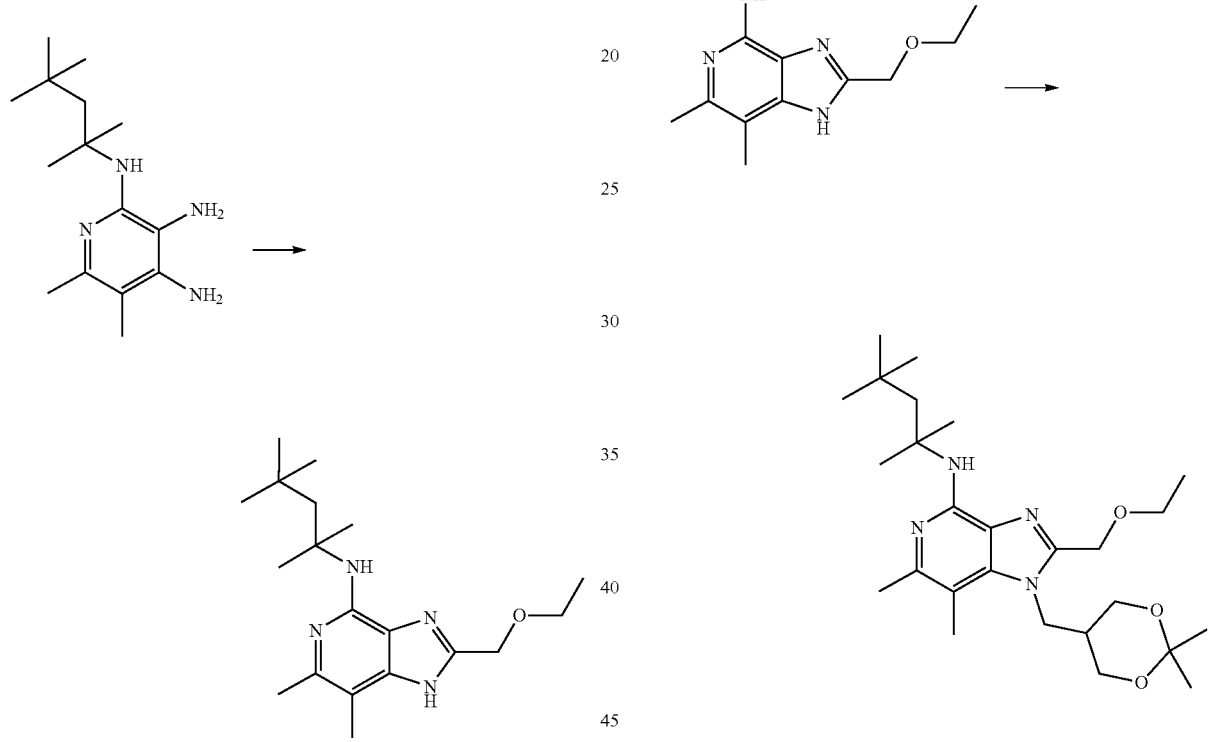

A solution of 5,6-dimethyl-N2-(2,4,4-trimethylpentan-2-yl)pyridine-2,3,4-triamine (5.60 g, 21.2 mmol) and dichloromethane (100 ml) was cooled to 0° C. To this was added 2-ethoxyacetyl chloride (2.73 g, 22.2 mmol, 2.44 ml) followed by triethylamine (3.21 g, 31.8 mmol, 4.43 ml). The reaction was stirred at 0° C. for 1.5 hrs. The reaction was diluted with dichloromethane (100 ml) and the organics washed with water (2×50 ml). The organics were dried over anhydrous sodium sulfate, filtered and concentrated. The residue was diluted with ethanol (100 ml) and sodium hydroxide (5.08 g, 127 mmol, 8.47 ml, 15N) was added. The reaction mixture was heated at 75° C. for 16 hrs. The reaction was cooled to RT and diluted with ethyl acetate and washed with water (2×). The combined aqueous was washed with ethyl acetate. The combined organics were dried over anhydrous sodium sulfate, filtered and concentrated. The residue was purified by silica gel chromatography (Heptane:Ethyl Acetate, 0-100% gradient) to provide the title compound. Yield: 1.40 g, 4.21 mmol, 19.8%. LCMS m/z 333.1 [M+H]$^+$. $^1$H NMR (400 MHz, CDCl$_3$) δ 9.10; (br. s., 1H), 4.96; (br. s., 1H), 4.73; (s, 2H), 3.65; (q, J=7.02 Hz, 2H), 2.42; (s, 3H), 2.25; (s, 3H), 2.07; (s, 2H), 1.59; (s, 6H), 1.29; (t, J=7.02 Hz, 3H), 0.99; (s, 9H).

Step 5: Synthesis of 1-((2,2-dimethyl-1,3-dioxan-5-yl)methyl)-2-(ethoxymethyl)-6,7-dimethyl-N-(2,4,4-trimethylpentan-2-yl)-1H-imidazo[4,5-c]pyridin-4-amine To a solution of 2-(ethoxymethyl)-6,7-dimethyl-N-(2,4,4-trimethylpentan-2-yl)-1H-imidazo[4,5-c]pyridin-4-amine (125 mg, 0.376 mmol), (2,2-dimethyl-1,3-dioxan-5-yl)methanol (68.7 mg, 0.470 mmol) in toluene (2 ml) was added cyanomethylenetributylphosphorane (136 mg, 0.564 mmol, 0.564 ml, 1M in toluene) and the reaction was heated at 90° C. for 1.5 hrs then cooled to RT and stirred for 16 hrs. Cyanomethylenetributylphosphorane (136 mg, 0.564 mmol, 0.564 ml, 1M in toluene) was added and the reaction stirred at 90° C. for 1.5 hrs. The reaction mixture was absorbed on silica gel and purified by silica gel chromatography (Heptane:Ethyl acetate 0-100% gradient.) to provide the title compound. Yield: 72 mg, 0.156 mmol, 42%. LCMS m/z 461.3 [M+H]$^+$. $^1$H NMR (400 MHz, CDCl$_3$) δ 5.13; (s, 1H), 4.79; (s, 2H), 4.62; (d, J=7.81 Hz, 2H), 4.02; (dd, J=2.93, 12.29 Hz, 2H), 3.60; (q, J=7.02 Hz, 2H), 3.51; (d, J=10.93 Hz, 2H), 2.43; (s, 3H), 2.38; (s, 3H), 2.06; (s, 2H), 1.90-1.98; (m, 1H), 1.58; (s, 6H), 1.47; (s, 6H), 1.24; (t, J=7.02 Hz, 3H), 0.99; (s, 9H).

43

Step 6: Synthesis of Example 1: 2-((4-amino-2-(ethoxymethyl)-6,7-dimethyl-1H-imidazo[4,5-c]pyridin-1-yl)methyl)propane-1,3-diol Trifluoroacetate Salt

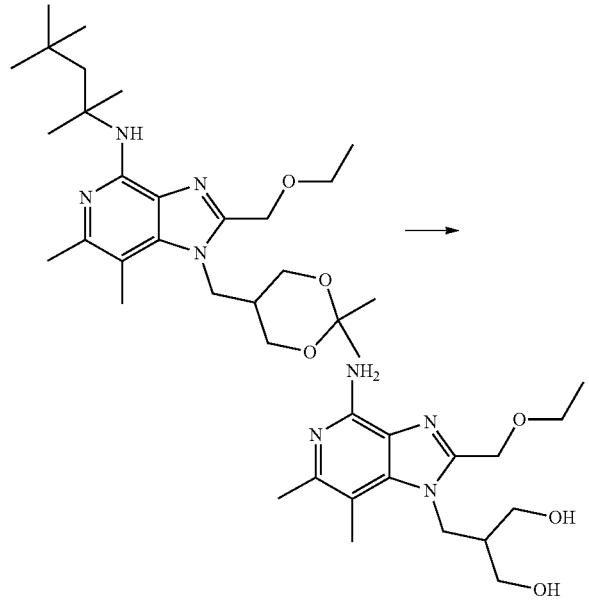

A solution of 1-((2,2-dimethyl-1,3-dioxan-5-yl)methyl)-2-(ethoxymethyl)-6,7-dimethyl-N-(2,4,4-trimethylpentan-2-yl)-1H-imidazo[4,5- c]pyridin-4-amine (72 mg, 0.16 mmol) in a 4:1 mixture of dichloromethane:trifluoroacetic acid (5 ml) was stirred at RT for 30min. Methanol (10 ml) was added and the reaction stirred at RT for 1.5 hrs. The reaction was concentrated and the residue was dissolved in dimethyl sulfoxide (1 ml) and purified by reversed phase HPLC. (Column: Waters Sunfire C18 19×100, 5u; Mobile phase A: 0.05% TFA in water (v/v); Mobile phase B: 0.05% TFA in acetonitrile (v/v); Gradient: HOLD at 95.0% $H_2O$/5.0% Acetonitrile for 1.0 min, 95.0% $H_2O$/5.0% Acetonitrile linear to 0% $H_2O$/100% Acetonitrile in 9.0 min, HOLD at 0% $H_2O$/100% Acetonitrile to 10.0 min. Flow: 25 mL/min.). Yield: 18.1 mg, 0.043 mmol, 27% HPLC Retention Time: 1.17 min (Column: Waters Atlantis® dc18 4.6×50, 5u; Mobile phase A: 0.05% TFA in water (v/v); Mobile phase B: 0.05% TFA in acetonitrile (v/v); Gradient: 95.0% $H_2O$/5.0% Acetonitrile linear to 5% $H_2O$/95% Acetonitrile in 4.0 min, HOLD at 5% $H_2O$/95% Acetonitrile to 5.0 min. Flow: 2 mL/min.); HPLC m/z 309.4 $[M+H]^+$.

Example (2): 2-((4-amino-2-(ethoxymethyl)-6,7-dimethyl-1H-imidazo[4,5-c]pyridin-1-yl)methyl)-2-methylpropane-1,3-diol

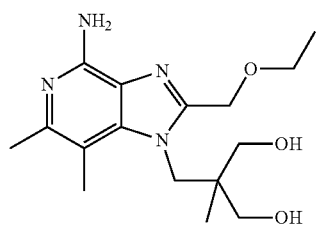 [SMILES: CCOCc1nc2c(N)nc(C)c(C)c2n1CC(C)(CO)CO]

44

Step 1: Synthesis of 5,6-dimethyl-3-nitropyridine-2,4-diol

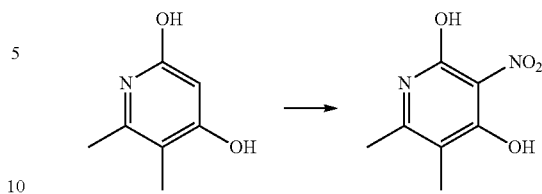

To 5,6-dimethylpyridine-2,4-diol (40.0 g, 287 mmol) (*Org. Lett.*, 2003, 5 (25), pp 4779-4782) at 18° C. was added concentrated sulfuric acid (174 ml). The reaction was cooled to 0° C. at which point nitric acid (68-70%, 45.8 ml) was added over 1.5 hrs, maintaining internal temperature below 10° C. After addition was complete the reaction was stirred at 10° C. for 30 min. This reaction was combined with a second reaction from 40 g 5,6-dimethylpyridine-2,4-diol. The combined reaction mixture was poured into ice-water (2 L). The yellow precipitate was collected by filtration and washed with water (5×200 ml) and MTBE (5×100 ml). The collected solids were dried under vacuum to provide the title compound as a yellow solid. Combined Yield: 50 g, 271.7 mmol, 47% yield based on 80 g starting pyridine. $^1$H NMR (400 MHz, DMSO-$d_6$) 12.34; (br s, 1H), 11.90; (br s, 1H), 2.21; (s, 3H), 1.90; (s, 3H).

Step 2: Synthesis of N2,N2-bis(4-methoxybenzyl)-5,6-dimethyl-3-nitro-N4-((2,2,5-trimethyl-1,3-dioxan-5-yl)methyl)pyridine-2,4-diamine

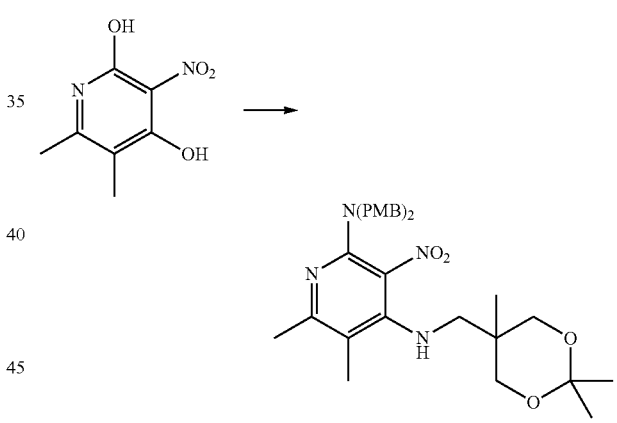

To a solution of 5,6-dimethyl-3-nitropyridine-2,4-diol (70.0 g, 380.1 mmol) in dichloroethane (1.4 L) cooled to 0° C. was added triethylamine (80.8 g, 798 mmol). Trifluoromethanesulfonic anhydride (220 g, 779 mmol) was added over 30 min at 0° C. The reaction was stirred at 0° C. for 1.5 hr. Triethylamine (42.3 g, 418 mmol) was added followed by portionwise addition of (2,2,5-trimethyl-1,3-dioxan-5-yl)methanamine (72.6 g, 456 mmol) (*Prepared from Organic & Biomolecular Chemistry*, 14(2), 483-494; 2016). The reaction was stirred at 0° C. for 20 min then stirred at 15° C. for 18 hrs. The reaction was cooled to 0° C. at which point triethylamine (115 g, 1.14 mol) was added followed by Bis(4-methoxybenzyl)amine (127 g, 494 mmol). The reaction was then stirred at 50° C. for 12 hrs. The solvent was removed and the residue was purified via silica gel column chromatography (Petroleum Ether:Ethyl Acetate gradient 0-10%). Product fractions were collected and evaporated to 10% volume. Solids were collected via filtration and filter cake washed with petroleum ether (3×50 ml). The filtrate was concentrated and purified via silica gel column chromatography (Petroleum Ether:Ethyl Acetate gradient 0-10%). Product fractions were collected and evaporated to 10% volume. Solids were collected via filtration and the filter cake washed with petroleum ether (3×20 ml), providing the title compound as a yellow solid. Yield: 98 g, 173.6 mmol, 45.7%. LCMS m/z 564.9 [M+H]⁺. ¹H NMR (400 MHz, CDCl₃) δ 7.05; (d, J=8.78 Hz, 4H), 6.80; (d, J=8.78 Hz, 4H), 6.47; (t, J=6.15 Hz, 1H), 4.34; (s, 4H), 3.79; (s, 6H), 3.54-3.67; (m, 4H), 3.42; (d, J=6.02 Hz, 2H), 2.35; (s, 3H), 2.21; (s, 3H), 1.43; (s, 3H), 1.41; (s, 3H), 0.83; (s, 3H).

Step 3: Synthesis of N2,N2-bis(4-methoxybenzyl)-5,6-dimethyl-N4-((2,2,5-trimethyl-1,3-dioxan-5-yl)methyl)pyridine-2,3,4-triamine

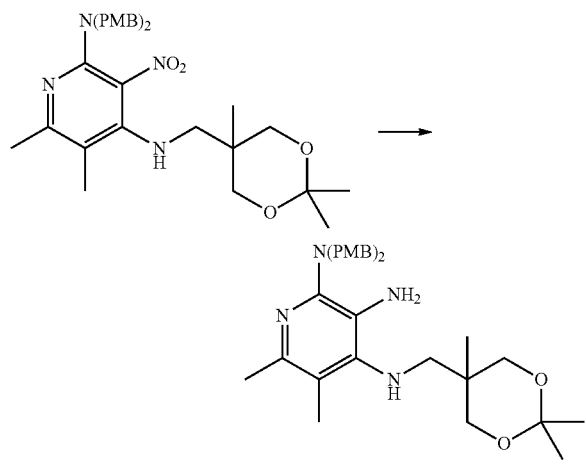

To a solution of N2,N2-bis(4-methoxybenzyl)-5,6-dimethyl-3-nitro-N4-((2,2,5-trimethyl-1,3-dioxan-5-yl)methyl)pyridine-2,4-diamine (57.0 g, 100.9 mmol) in methanol (673 ml) was added ammonium formate (63.7 g, 1.01 mol) and then Zinc Dust (66.0 g, 1.01 mol). The reaction was stirred for 10 min at 15° C. The reaction mixture was filtered through Celite® and the filtrate concentrated. The residue was dissolved in ethyl acetate and water slowly added to form a white precipitate. The aqueous layer was extracted with ethyl acetate. The combined organics were washed with brine, dried over anhydrous sodium sulfate, filtered and concentrated to provide the title compound as a brown oil. Used without further purification Yield: 50.0 g, 96.4 mmol, 95.5%. LCMS m/z 535.0 [M+H]⁺.

Step 4: Synthesis of N-(2-(bis(4-methoxybenzyl)amino)-5,6-dimethyl-4-(((2,2,5-trimethyl-1,3-dioxan-5-yl)methyl)amino)pyridin-3-yl)-2-ethoxyacetamide

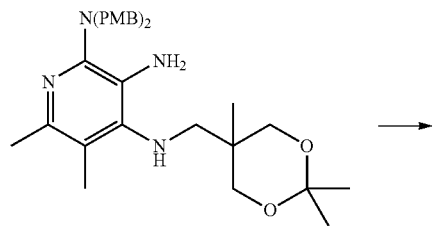

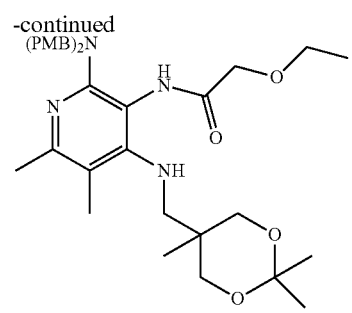

To a solution of N2,N2-bis(4-methoxybenzyl)-5,6-dimethyl-N4-((2,2,5-trimethyl-1,3-dioxan-5-yl)methyl)pyridine-2,3,4-triamine (100 g, 192.8 mmol) in dichloromethane (1L) was added triethylamine (97.5 g, 964 mmol, 134 ml). The reaction was cooled to 0° C. at which point 2-ethoxyacetyl chloride (37.8 g, 308 mmol) was added dropwise. The ice bath was removed and the reaction stirred at 25° C. for 16 hrs. The solvent was removed, and the product used without further purification. Yield: 150 g, 192.8 mmol, assumed quantitative.

Step 5: Synthesis of 2-(ethoxymethyl)-N,N-bis(4-methoxybenzyl)-6,7-dimethyl-1-((2,2,5-trimethyl-1,3-dioxan-5-yl)methyl)-1H-imidazo[4,5-c]pyridin-4-amine

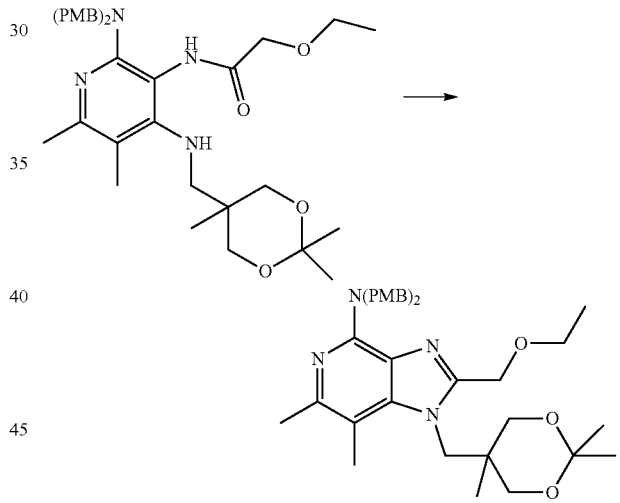

To a solution of crude N-(2-(bis(4-methoxybenzyl)amino)-5,6-dimethyl-4-(((2,2,5-trimethyl-1,3-dioxan-5-yl)methyl)amino)pyridin-3-yl)-2- ethoxyacetamide from the above reaction in ethanol (3.45 L cooled to 0° C.) was added sodium hydroxide (64.4 ml, 15N aqueous). After addition the reaction was heated to reflux for 16 hrs. The reaction was cooled to 15° C. at which point a white precipitate formed. The solids were filtered and the filter cake washed with water and MTBE. The white solids were dissolved in ethyl acetate (1 L) and the organic layer was washed with brine, dried over anhydrous sodium sulfate, filtered and concentrated. The residue was purified by silica gel chromatography (Ethyl Acetate: Petroleum Ether gradient 0-45%.) to provide product. This material was combined with an additional 7.2 g of product from a different batch and stirred for 20 min in a 2:1 solution of petroleum ether:MTBE. The solids were filtered and dried on vacuum to provide the title compound as a white solid. Combined yield: 94.52 g, 157 mmol, 76% yield. LCMS m/z 603.0 [M+H]⁺. ¹H NMR (600 MHz, DMSO-d₆) δ 7.16; (d, J=8.22 Hz, 4H), 6.83; (d, J=8.80 Hz, 4H), 4.82-5.27; (m, 6H), 4.36-4.80; (m, 4H), 3.70; (s, 6H), 3.51-3.68; (m, 2H), 3.40-3.46; (m, 2H), 2.41; (s, 3H), 2.34; (s, 3H), 1.39; (s, 3H), 1.34; (s, 3H), 1.07; (t, J=7.04 Hz, 3H), 0.56; (s, 3H).

Step 6: Synthesis of Example (2): 2-((4-amino-2-(ethoxymethyl)-6,7-dimethyl-1H-imidazo[4,5-c]pyridin-1-yl)methyl)-2- methylpropane-1,3-diol

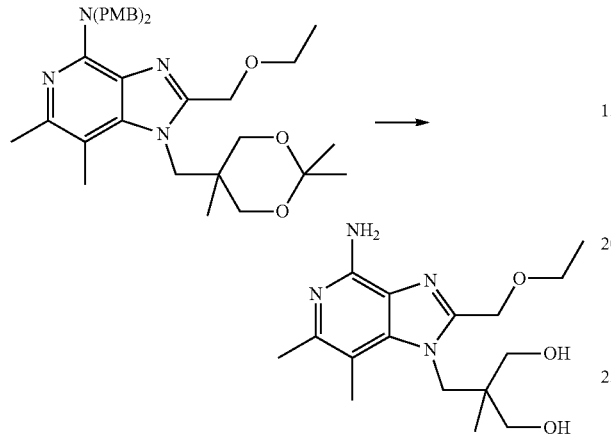

To a solution of 2-(ethoxymethyl)-N,N-bis(4-methoxybenzyl)-6,7-dimethyl-1-((2,2,5-trimethyl-1,3-dioxan-5-yl)methyl)-1H-imidazo[4,5-c]pyridin-4-amine (477 mg, 0.791 mmol) and dichloromethane (3 ml) in a vial was added concentrated hydrochloric acid (7.91 mmol, 0.66 ml) dropwise. The vial was capped and the reaction was stirred at RT for 2 hrs then heated at 50° C. for 1 hr. Additional concentrated hydrochloric acid (4.8 mmol, 0.40 ml) was added and the reaction continued heating at 50° C. for 30 min. The reaction was then cooled to RT and stirred for 16 hrs. Water (2 ml) was added and the aqueous was washed with dichloromethane (2×3 ml). The aqueous was brought to pH 9 with solid sodium carbonate. The reaction was then heated to reflux and cooled to 4° C. The solids were filtered and washed with water (5 ml) and ether (5 ml) and dried under vacuum to provide the title compound as a white solid. Yield. 194 mg, 0.602 mmol, 76.0%. LCMS m/z 323.3 [M+H]⁺. ¹H NMR (400 MHz, DMSO-d₆) δ 5.76; (s, 2H), 4.91-5.09; (m, 1H), 4.69-4.90; (m, 2H), 4.27-4.59; (m, 3H), 3.39-3.56; (m, 2H), 3.29-3.37; (m, 1H, assumed, partially obscured by H₂O), 3.14-3.29; (m, 2H), 2.95-3.13; (m, 1H), 2.41; (s, 3H), 2.29; (s, 3H), 1.06-1.14; (m, 3H), 0.48; (s, 3H).

Example (3): 2-((4-amino-2-(ethoxymethyl)-1H-imidazo[4,5-c]quinolin-1-yl)methyl)-2-methylpropane-1,3-diol

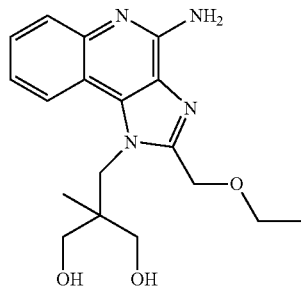 [SMILES: CCOCc1nc2c(N)nc3ccccc3c2n1CC(C)(CO)CO]

Prepared in a manner similar to 2-((4-amino-2-(ethoxymethyl)-6,7-dimethyl-1H-imidazo[4,5-c]pyridin-1-yl)methyl)-2-methylpropane-1,3- diol starting from quinoline-2,4-diol. 18.5 mg prepared. LCMS m/z 345.4 [M+H]⁺. ¹H NMR (400 MHz, DMSO-d₆) δ ppm 0.58; (s, 3 H) 1.15; (t, J=7.02 Hz, 3 H) 3.07-3.77; (m, 7 H) 4.58-5.26; (m, 5 H) 7.52; (t, J=8.0 Hz, 1 H) 7.71; (t, J=8.0 Hz, 1 H) 7.79; (d, J=8.0 Hz, 1 H) 8.74; (d, J=8.0 Hz, 1 H) 9.19; (br s, 1 H)

Example (4): 2-((4-amino-2-(ethoxymethyl)-7,8-dihydrocyclopenta[b]imidazo[4,5-d]pyridin-1(6H)-yl)methyl)-2-methylpropane-1,3-diol

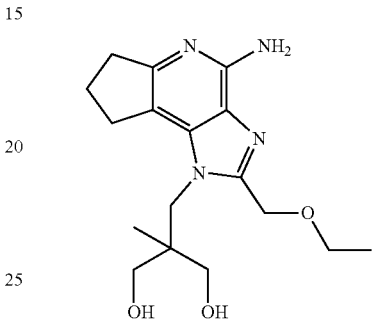

Prepared in a manner similar to 2-((4-amino-2-(ethoxymethyl)-6,7-dimethyl-1H-imidazo[4,5-c]pyridin-1-yl)methyl)-2-methylpropane-1,3- diol starting from 6,7-dihydro-5H-cyclopenta[b]pyridine-2,4-diol, 60 mg prepared. LCMS Retention Time: 0.715 min (Column: ACQUITY UPLC BEH C18 50*2.1 mm, 1.7 um; Mobile phase A: 0.05% NH₄OH in water (v/v); Mobile phase B: Acetonitrile; Gradient: HOLD at 100% H₂O for 0.10 min, 100% H₂O to 0% H₂O/100% Acetonitrile in 0.90 min, HOLD at 0% H₂O/100% Acetonitrile for 0.2 min. Flow: 1.0 mL/min.). LCMS m/z 335.3 [M+H]⁺. ¹H NMR (CDCl₃, 400 MHz), characteristic peaks: δ 5.1-5.3; (m, 2H), 4.8-5.0; (m, 2H), 4.1-4.8; (m, 3H), 3.5-3.8; (m, 6H), 3.1-3.3; (m, 2H), 2.9-3.0; (m, 2H), 2.1-2.2; (m, 2H), 1.26; (t, 3H, J=7.0 Hz), 0.65; (s, 3H).

Example (5): 2-((4-amino-2-(ethoxymethyl)-6,7,8,9-tetrahydro-1H-imidazo[4,5-c]quinolin-1-yl)methyl)-2-methylpropane-1,3-diol Formate Salt

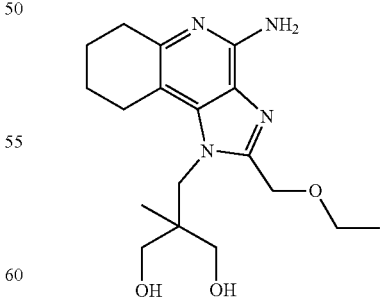

Prepared in a manner similar to 2-((4-amino-2-(ethoxymethyl)-6,7-dimethyl-1H-imidazo[4,5-c]pyridin-1-yl)methyl)-2-methylpropane-1,3- diol starting from 6,7-dihydro-5H-cyclopenta[b]pyridine-2,4-diol, 34 mg prepared. LCMS Retention Time: 0.621 min (Column: ACQUITY UPLC BEH C18 50*2.1 mm, 1.7 um; Mobile phase A: 0.05% NH$_4$OH in water (v/v); Mobile phase B: Acetonitrile; Gradient: 95% H$_2$O/5% Acetonitrile to 0% H$_2$O/100% Acetonitrile over 1 min, HOLD at 0% H$_2$O/100% Acetonitrile for 0.2 min. Flow: 1.0 mL/min.). LCMS m/z 349.2 [M+H]$^+$. $^1$H NMR (Methanol-d4, 400 MHz), characteristic peaks: δ 8.4-8.6; (m, 1H), 4.63; (s, 2H), 3.59-3.68; (m, 2H), 3.1-3.6; (m, 5H, assumed, partially obscured by solvent), 2.8-3.0; (m, 3H), 1.72-2.06; (m, 4H), 1.22; (t, 3H, J=7.0 Hz), 0.60; (s, 3H).

Examples (6) and (7): (R)-3-(4-amino-2-(ethoxymethyl)-6,7-dimethyl-1H-imidazo[4,5-c]pyridin-1-yl)-2-(methoxymethyl)-2- methylpropan-1-ol and (S)-3-(4-amino-2-(ethoxymethyl)-6,7-dimethyl-1H-imidazo[4,5-c]pyridin-1-yl)-2-(methoxymethyl)-2-methylpropan-1-ol

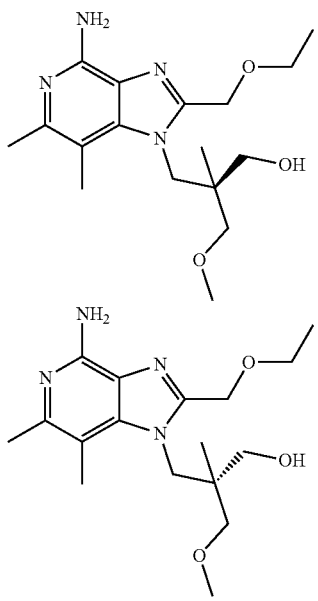

Step 1: Synthesis of (2,2,5-trimethyl-1,3-dioxan-5-yl)methanol

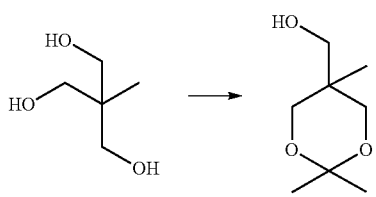

To a stirred solution of 2-(hydroxymethyl)-2-methylpropane-1,3-diol (50.0 g, 416.2 mmol) and 2,2-dimethoxypropane (65.0 g, 624.0 mmol) was added acetone (46 ml) and p-toluenesulfonic acid (3.96 g, 20. 8 mmol). The reaction mixture was heated at 30° C. for 12 hrs.

The reaction was cooled to RT and a solution of sodium bicarbonate (12 g) in water (400 ml) was added. The aqueous was extracted with ethyl acetate and the organic layer was washed with brine, dried over anhydrous sodium sulfate, filtered and concentrated to provide the title compound as a white solid. Yield: 52.9 g, 330.2 mmol, 79.3%.

$^1$H NMR (400 MHz, DMSO-d$_6$) δ 4.58; (t, J=5.40 Hz, 1H), 3.53-3.57; (m, 2H), 3.41-3.45; (m, 2H), 3.33-3.36; (m, 2H, partial obscured by solvent), 1.32; (s, 3H), 1.26; (s, 3H), 0.74; (s, 3H).

Step 2: Synthesis of 5-(methoxymethyl)-2,2,5-trimethyl-1,3-dioxane

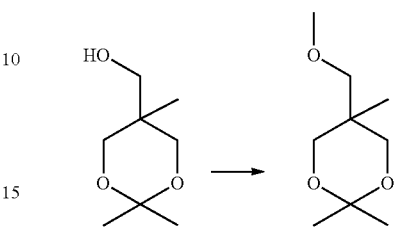

To a suspension of sodium hydride (33.8 g, 844 mmol, 60% dispersion in mineral oil) in toluene (1.35 L) cooled to 0° C. was added (2,2,5-trimethyl-1,3-dioxan-5-yl)methanol (67.6 g, 421.9 mmol) and the reaction was stirred at 0° C. for 10 min and then stirred to 40° C. for 18 hrs. The reaction was cooled to 0° C., methyl iodide (135 g, 951.1 mmol) was added and the reaction stirred at 15° C. for 60 h. The reaction mixture was diluted with water (300 ml) and the aqueous extracted with petroleum ether (3×100 ml). The combined organic layer was concentrated to provide the title compound as a yellow oil. Yield: 60.0 g, 344.4 mmol, 81.6%. $^1$H NMR (400 MHz, DMSO-d$_6$) δ 3.51-3.57; (m, 2H), 3.43-3.49; (m, 2H), 3.28; (s, 2H), 3.25; (s, 3H), 1.33; (s, 3H), 1.27; (s, 3H), 0.79; (s, 3H).

Step 3: Synthesis of 2-(methoxymethyl)-2-methylpropane-1,3-diol

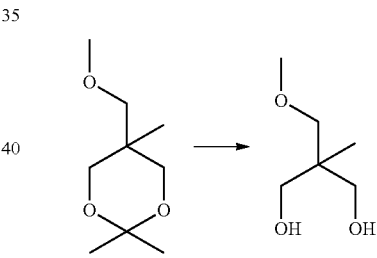

To a suspension of 5-(methoxymethyl)-2,2,5-trimethyl-1, 3-dioxane (55.0 g, 315.7 mmol) in methanol (316 ml) cooled to 0° C. was added hydrochloric acid (31.6 ml, 3M aqueous). The reaction mixture was stirred at 25° C. for 30 min. The reaction mixture was concentrated and to the residue was added water (100 ml). The aqueous was extracted with petroleum ether (3×200 ml) and then lyophilized to provide the title compound as a yellow oil. Yield: 32.2 g, 239.8 mmol, 75.9%. $^1$H NMR (400 MHz, CDCl$_3$) δ 3.65-3.69; (m, 2H), 3.62; (s, 2H), 3.54-3.58; (m, 2H), 3.37; (s, 2H), 3.34; (s, 3H), 0.81; (s, 3H).

Step 4: Synthesis of 3-((tert-butyldimethylsilyl)oxy)-2-(methoxymethyl)-2-methylpropan-1-ol

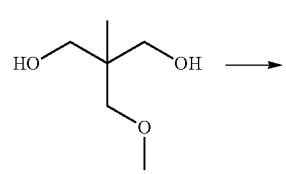

-continued

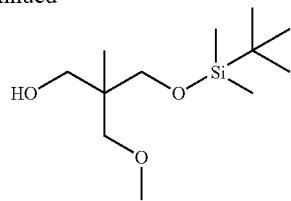

To a solution of 2-(methoxymethyl)-2-methylpropane-1, 3-diol (515 mg, 3.84 mmol) in tetrahydrofuran (25 ml) cooled to 0° C., was added sodium hydride (144 mg, 3.61 mmol, 60% dispersion in mineral oil). The reaction was stirred at 0° C. for 15 min. tert-Butyldimethylsilyl chloride (579 mg, 3.84 mmol) in tetrahydrofuran (5 ml) was added dropwise. The reaction mixture was stirred at 0° C. for 30 min and at RT for 3 hrs. The reaction was then diluted with methanol (1 ml), saturated aqueous sodium bicarbonate (10 ml) and water (15 ml). The aqueous was extracted with dichloromethane (2×40 ml). The combined organics were dried over anhydrous sodium sulfate, filtered and concentrated. The residue was purified by silica gel chromatography (Heptane:Ethyl Acetate, gradient 0-60%) to provide the title compound, Yield: 446 mg, 1.80 mmol, 46.8%. $^1$H NMR (400 MHz, CDCl$_3$) δ 3.55-3.64; (m, 4H), 3.37; (d, J=3.90 Hz, 2H), 3.35; (s, 3H), 0.90-0.91; (s, 9H), 0.82; (s, 3H), 0.05-0.08; (s, 6H).

Step 5: Synthesis of 1-(3-((tert-butyldimethylsilyl)oxy)-2-(methoxymethyl)-2-methylpropyl)-2-(ethoxymethyl)-6,7-dimethyl-N-(2,4,4-trimethylpentan-2-yl)-1H- imidazo[4,5-c]pyridin-4- amine

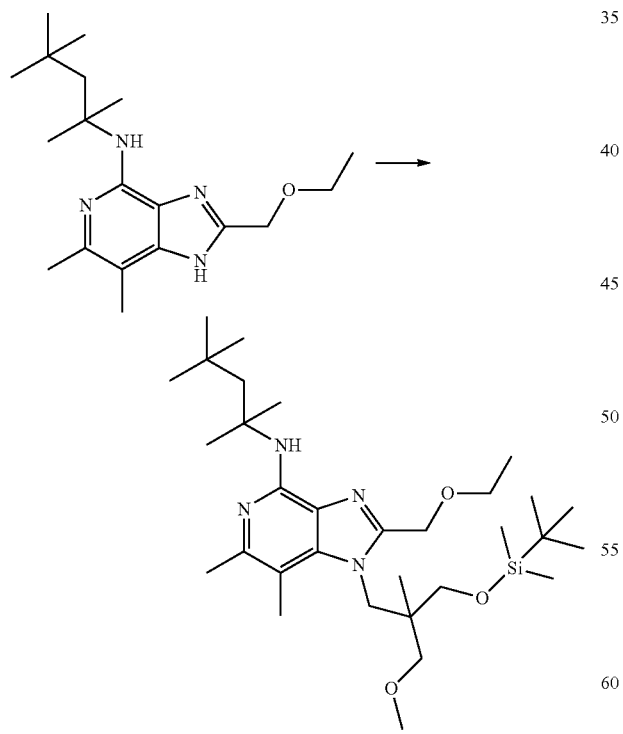

To a solution of 2-(ethoxymethyl)-6,7-dimethyl-N-(2,4,4-trimethylpentan-2-yl)-1H-imidazo[4,5-c]pyridin-4-amine (69 mg, 0.21 mmol) and 3-((tert-butyldimethylsilyl)oxy)-2-(methoxymethyl)-2-methylpropan-1-ol (111 mg, 0.42 mmol) in toluene (1 ml) was added cyanomethylenetributylphosphorane (125 mg, 0.519 mmol, 0.519 ml, 1.0M in acetonitrile). The reaction was stirred at 100° C. for 16 hrs. The reaction mixture was absorbed on silica gel and purified by silica gel chromatography (Heptane:Ethylacetate, gradient 0-60%) to provide the title compound. Yield: 69 mg, 0.12 mmol, 59%. LCMS m/z 563.7 [M+H]$^+$. $^1$H NMR (400 MHz, MeOD) δ 4.38-4.78; (m, 4H), 3.44-3.65; (m, 4H), 3.02-3.22; (m, 2H), 2.47; (s, 3H), 2.41; (s, 3H), 2.08; (br. s., 2H), 1.56; (s, 6H), 1.25-1.35; (m, 4H), 1.19; (t, J=6.83 Hz, 3H), 0.94; (s, 9H), 0.92; (s, 9H), 0.69; (s, 3H), 0.07; (s, 6H).

Step 6: Synthesis of Example (6) and (7) (R)-3-(4-amino-2-(ethoxymethyl)-6,7-dimethyl-1H-imidazo[4,5-c]pyridin-1-yl)-2- (methoxymethyl)-2- methylpropan-1-ol and (S)-3-(4-amino-2-(ethoxymethyl)-6,7-dimethyl-1H-imidazo[4,5-c]pyridin-1-yl)-2-(methoxymethyl)-2-methylpropan-1-

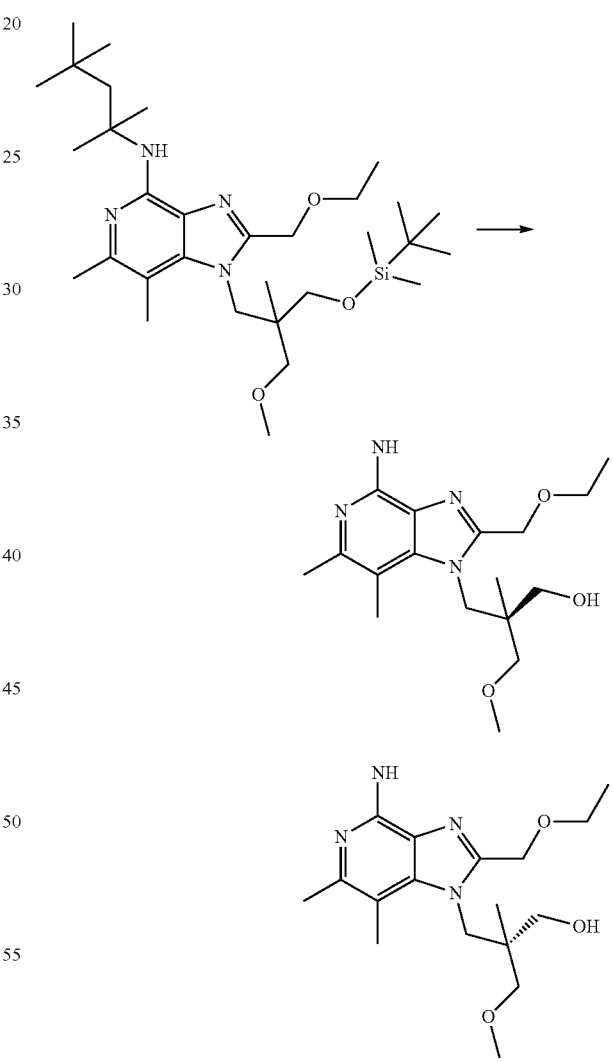

To a solution of 1-(3-((tert-butyldimethylsilyl)oxy)-2-(methoxymethyl)-2-methylpropyl)-2-(ethoxymethyl)-6,7-dimethyl-N-(2,4,4-trimethylpentan-2- yl)-1H-imidazo[4,5-c]pyridin-4-amine (69 mg, 0.12 mmol) in hexafluoroisopropanol (5.0 ml) was added methanesulfonic acid (70.7 mg, 0.735 mmol, 0.048 ml). The reaction was stirred for 5 hrs at RT. The reaction mixture was diluted with saturated aqueous sodium bicarbonate and washed with ethyl acetate (1×) and dichloromethane (1×). Organics were combined, dried over anhydrous sodium sulfate, filtered and concentrated. The residue was purified by silica gel chromatography (Dichloromethane: Methanol, 0-30% gradient). The product was collected, concentrated and filtered through a nylon disk. Solvent was removed to provide 41 mg of racemate. The racemate was then dissolved in 1 ml ethanol and purified by supercritical fluid chromatography. (Column: Phenomenex Lux Cellulose 4 5 um 21×250 mm); Mobile phase A: Methanol w/0.2% Ammonium Hydroxide (v/v); Mobile phase B: $CO_2$ (v/v); Gradient: 70.0% $CO_2$/30.0% Methanol w/0.2% Ammonium Hydroxide Isocratic over 5 min. Flow: 75 mL/min. Back Pressure: 120 Bar), to afford Ent 1 as Example (6): 13.8 mg, 0.041 mmol, 33.6%, 99% ee, and Ent 2 as Example (7): 13.1 mg, 0.039 mmol, 31.9%, 99% ee. SFC retention time Ent 1 as Example (6): 3.04 min, m/z 337.5 [M+H]$^+$, SFC retention time Ent 2 as Example (7): 4.15 min, m/z 337.5 [M+H]+(Column: Phenomenex Lux Cellulose 4 5 um 4.6×100 mm; Mobile phase A: Methanol w/0.2% Ammonium Hydroxide (v/v); Mobile phase B: $CO_2$ (v/v); Gradient: 60.0% $CO_2$/0.0% Methanol w/0.2% Ammonium Hydroxide Isocratic over 5 min. Flow: 1.5 mL/min. Back Pressure: 120 Bar). The specific stereochemistry of Example (6) and Example (7) is not assigned. but each enantiomer is 99% ee as provided above.

Example (8): 2-((4-amino-6,7-dimethyl-2-(2,2,2-trifluoroethyl)-1H-imidazo[4,5-c]pyridin-1-yl)methyl)-2-methylpropane-1,3- diol Trifluoroacetate Salt

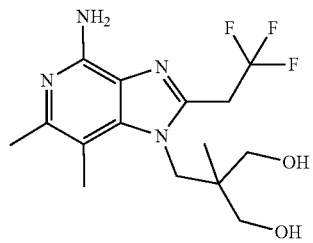 [SMILES: Cc1nc(N)c2nc(CC(F)(F)F)n(CC(C)(CO)CO)c2c1C]

Step 1: Synthesis of N-(2-(bis(4-methoxybenzyl)amino)-5,6-dimethyl-4-(((2,2,5-trimethyl-1,3-dioxan-5-yl)methyl)amino)pyridin-3-yl)-3,3,3-trifluoropropanamide

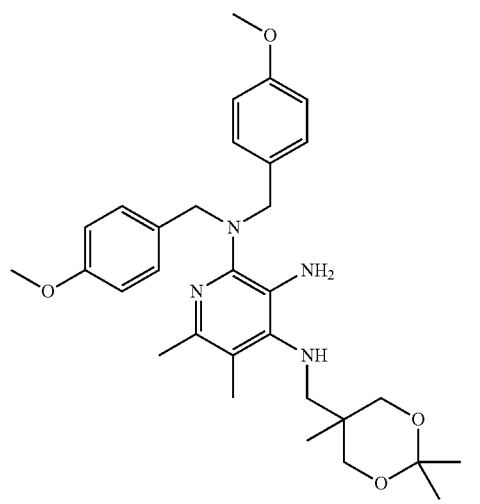

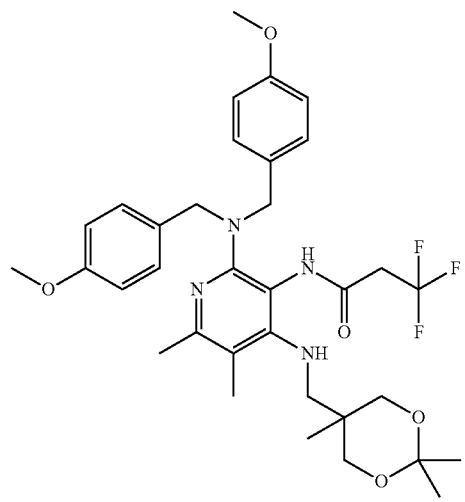

To a solution of 3,3,3-trifluoropropionic acid (15.1 mg, 0.118 mmol, 0.0104 ml) was added N2,N2-bis(4-methoxybenzyl)-5,6-dimethyl-N4-((2,2,5-trimethyl-1,3-dioxan-5-yl)methyl)pyridine-2,3,4-triamine (60 mg, 0.11 mmol) and triethylamine (22.7 mg, 0.224 mmol, 0.031 ml). Propylphosphonic acid anhydride (143 mg, 0.224 mmol, 0.101 ml, 50% in ethyl acetate) was added and the reaction stirred at RT for 1 hr. Water was added and the aqueous washed twice with ethyl acetate. The organics were combined and dried over anhydrous sodium sulfate, filtered and concentrated. The crude compound was used in the subsequent step without further purification or analysis, Yield: 60 mg, 0.093 mmol, 83%.

Step 2: Synthesis of N,N-bis(4-methoxybenzyl)-6,7-dimethyl-2-(2,2,2-trifluoroethyl)-1-((2,2,5-trimethyl-1,3-dioxan-5-yl)methyl)-1H- imidazo[4,5-c]pyridin-4-amine

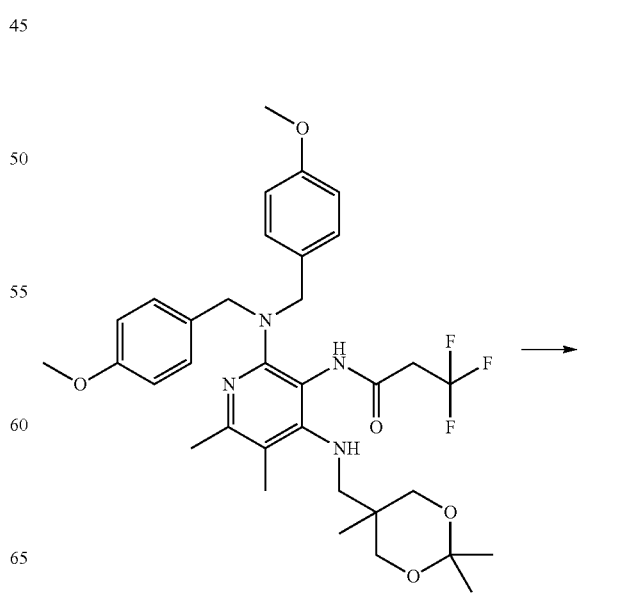

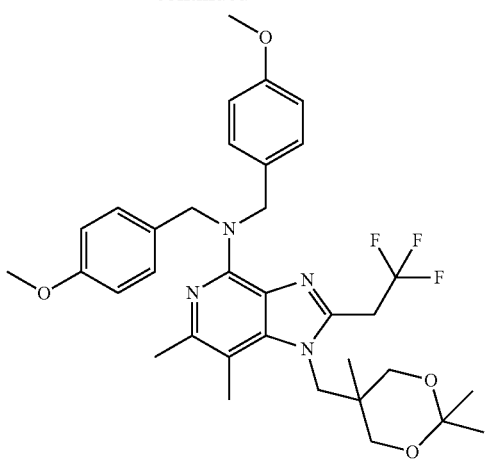

To a solution of N-(2-(bis(4-methoxybenzyl)amino)-5,6-dimethyl-4-(((2,2,5-trimethyl-1,3-dioxan-5-yl)methyl)amino)pyridin-3-yl)-3,3,3- trifluoropropanamide (40 mg, 0.062 mmol) was added carbon tetrachloride (1 ml). To this was added triethylamine (18.8 mg, 0.186 mmol, 0.026 ml) and triphenylphosphine (48.8 mg, 0.186 mmol). The reaction was heated at 80° C. for 16 hrs.

The reaction mixture was then cooled to RT and filtered through Celite® and filter cake washed with ethyl acetate. The filtrate was concentrated, and the residue was purified by silica gel chromatography (Heptane: Ethyl Acetate, gradient 0-30%) to provide title compound. Yield: 10 mg, 0.016 mmol, 26%. $^1$H NMR (400 MHz, CDCl$_3$) δ 7.27-7.30; (m, 4H, assumed, partially obscured by residual CHCl$_3$), 6.82; (d, J=8.59 Hz, 4H), 5.25-5.37; (m, 2H), 4.83-5.01; (m, 3H), 4.33-4.58; (m, 2H), 3.79; (s, 6H), 3.76-3.84; (m, 1H, assumed, partially obscured by peak at 3.79 ppm), 3.60-3.74; (m, 2H), 3.48-3.56; (m, 1H), 3.19-3.27; (m, 1H), 2.45; (s, 3H), 2.44; (s, 3H), 1.50; (s, 3H), 1.48; (s, 3H), 0.63; (s, 3H). LCMS m/z 627.5 [M+H]$^+$.

Step 3: Synthesis of Example (8): 2-((4-amino-6,7-dimethyl-2-(2,2,2-trifluoroethyl)-1H-imidazo[4,5-c]pyridin-1-yl)methyl)-2-methylpropane-1,3-diol Trifluoroacetate Salt

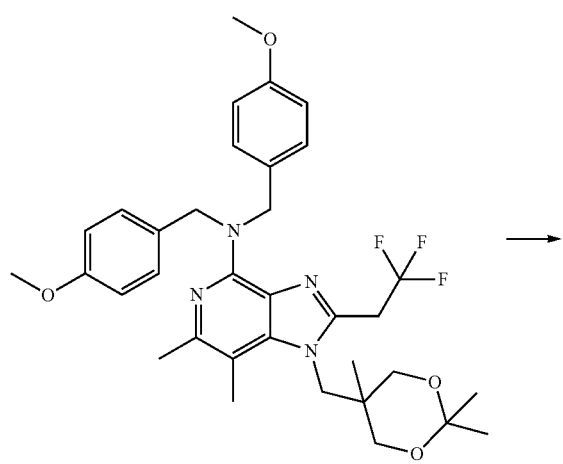

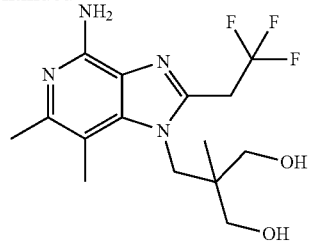

To a solution of N,N-bis(4-methoxybenzyl)-6,7-dimethyl-2-(2,2,2-trifluoroethyl)-1-((2,2,5-trimethyl-1,3-dioxan-5-yl)methyl)-1H-imidazo[4,5-c]pyridin-4-amine (10 mg, 0.016 mmol) in hexafluoroisopropanol (0.5 ml) was added methanesulfonic acid (2 drops). The reaction was stirred at RT for 3 hrs. The reaction was then concentrated and the residue was diluted with 1 ml dimethyl sulfoxide and purified via reversed phase HPLC (Column: Waters Sunfire C18 19×100, 5u; Mobile phase A: 0.05% TFA in water (v/v); Mobile phase B: 0.05% TFA in acetonitrile (v/v); Gradient: 95.0% H$_2$O/5.0% Acetonitrile linear to 70% H$_2$O /30% Acetonitrile in 8.5 min to 0% H$_2$O/100% MeCN to 9.0 min, HOLD at 0% H$_2$O/100% Acetonitrile from 9.0 to 10.0 min. Flow: 25 mL/min.) to provide title compound, yield: 5.5 mg, 0.012, 75%; HPLC Retention Time: 1.31 min. (Column: Waters Atlantis® dc18 4.6×50, 5u; Mobile phase A: 0.05% TFA in water (v/v); Mobile phase B: 0.05% TFA in acetonitrile (v/v); 95.0% H$_2$O/5.0% Acetonitrile linear to 5% H$_2$O/95% Acetonitrile in 4.0min, HOLD at 5% H$_2$O/95% Acetonitrile to 5.0 min. Flow: 2 mL/min.). HPLC m/z 347.5 [M+H]$^+$.

Example (9): 2-((4-amino-2-(ethoxymethyl)-6,7-dimethyl-1H-imidazo[4,5-c]pyridin-1-yl)methyl)-2-ethylpropane-1,3-diol Trifluoroacetate Salt

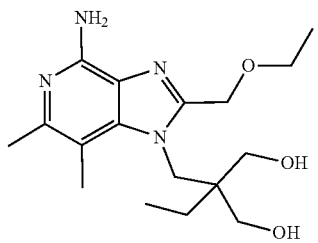 [SMILES: CCOCc1nc2c(N)nc(C)c(C)c2n1CC(CC)(CO)CO]

Prepared in a manner similar to Example (2), by utilizing (5-ethyl-2,2-dimethyl-1,3-dioxan-5-yl)methanol (Polymer Chemistry, 8(3), 592-604; 2017), in step 5. The product was isolated by reversed-phase HPLC (Column: Waters Sunfire C18 19×100, 5u; Mobile phase A: 0.05% TFA in water (v/v); Mobile phase B: 0.05% TFA in acetonitrile (v/v); Gradient: 95.0% H$_2$O/5.0% Acetonitrile linear to 45% H$_2$O/55% Acetonitrile in 8.5min to 0% H$_2$O/100% MeCN to 9.0min, HOLD at 0% H$_2$O/100% Acetonitrile from 9.0 to 10.0 min. Flow: 25 mL/min.) to afford the title compound, yield: 25.2 mg, 0.056 mmol, 46.7%; HPLC Retention Time: 1.35 min (Column: Waters Atlantis® dc18 4.6×50, 5u; Mobile phase A: 0.05% TFA in water (v/v); Mobile phase B: 0.05% TFA in acetonitrile (v/v); 95.0% H$_2$O/5.0% Acetonitrile linear to 5% H$_2$O/95% Acetonitrile in 4.0 min, HOLD at 5% H$_2$O/ 95% Acetonitrile to 5.0 min. Flow: 2 mL/min.); HPLC m/z 337.5 [M+H]$^+$.

Example (10): 2-((4-amino-2-butyl-1H-imidazo[4,5-c]quinolin-1-yl)methyl)-2-methylpropane-1,3-diol

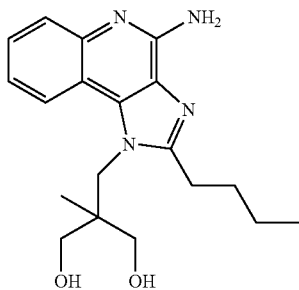 [SMILES: CCCCc1nc2c(N)nc3ccccc3c2n1CC(C)(CO)CO]

Prepared in a manner similar to Example (1) 2-((4-amino-2-(ethoxymethyl)-6,7-dimethyl-1H-imidazo[4,5-c]pyridin-1-yl)methyl)-2- methylpropane-1,3-diol starting from quinoline-2,4-diol in step 1 and utilizing valeroyl chloride in step 4. 37.8 mg prepared. HPLC retention time: 1.69 min (Column: Waters Atlantis® dc18 4.6×50, 5u; Mobile phase A: 0.05% TFA in water (v/v); Mobile phase B: 0.05% TFA in acetonitrile (v/v); Gradient: 95.0% $H_2O$/5.0% Acetonitrile linear to 5% $H_2O$/95% Acetonitrile in 4.0 min, HOLD at 5% $H_2O$/95% Acetonitrile to 5.0 min. Flow: 2 mL/min.). HPLC m/z 343.5 $[M+H]^+$.

Example (11): 2-((4-amino-2-butyl-6,7-dimethyl-1H-imidazo[4,5-c]pyridin-1-yl)methyl)-2-methyl-propane-1,3-diol

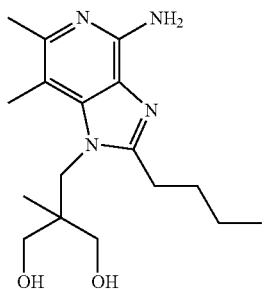 [SMILES: CCCCc1nc2c(N)nc(C)c(C)c2n1CC(C)(CO)CO]

Prepared in a manner similar to 2-((4-amino-2-(ethoxymethyl)-6,7-dimethyl-1H-imidazo[4,5-c]pyridin-1-yl) methyl)-2-methylpropane-1,3- diol utilizing valeroyl chloride in Example 1, step 4. 260 mg prepared. $^1$H NMR (DMSO-$d_6$, 400 MHz) δ 5.56; (s, 2H), 4.8-5.0; (m, 2H), 4.3-4.5; (m, 1H), 4.1-4.3; (m, 1H), 3.1-3.3; (m, 3H), 3.0-3.1; (m, 1H), 2.8-3.0; (m, 2H), 2.40; (s, 3H), 2.28; (s, 3H), 1.6-1.7; (m, 2H), 1.3-1.4; (m, 2H), 0.91; (t, 3H, J=7.2 Hz), 0.45; (s, 3H). LCMS m/z 321.2 $[M+H]^+$.

Example (12): 2-((4-amino-2-pentyl-1H-imidazo[4,5-c]quinolin-1-yl)methyl)-2-methylpropane-1,3-diol

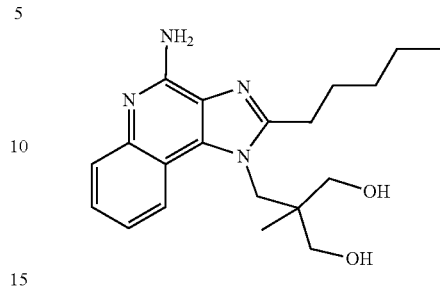

Prepared in a manner similar to Example (1) 2-((4-amino-2-(ethoxymethyl)-6,7-dimethyl-1H-imidazo[4,5-c]pyridin-1-yl)methyl)-2- methylpropane-1,3-diol starting from quinoline-2,4-diol in step 1 and utilizing Hexanoyl chloride in step 4. 31.2 mg prepared. HPLC retention time: 1.88 min (Column: Waters Atlantis® dc18 4.6×50, 5u; Mobile phase A: 0.05% TFA in water (v/v); Mobile phase B: 0.05% TFA in acetonitrile (v/v); Gradient: 95.0% $H_2O$/5.0% Acetonitrile linear to 5% $H_2O$/95% Acetonitrile in 4.0 min, HOLD at 5% $H_2O$/95% Acetonitrile to 5.0 min. Flow: 2 mL/min.). HPLC m/z 357.5 $[M+H]^+$.

Example (13): 2-((4-amino-2-butyl-6,7,8,9-tetrahydro-1H-imidazo[4,5-c]quinolin-1-yl)methyl)-2-methylpropane-1,3-diol Formate Salt

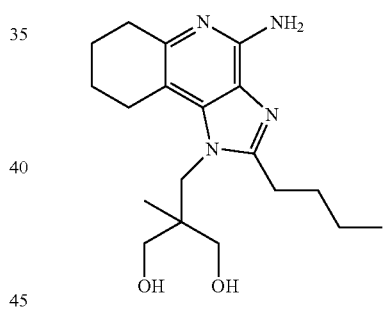

Step 1: Synthesis of 3-nitro-5,6,7,8-tetrahydroquinoline-2,4-diol

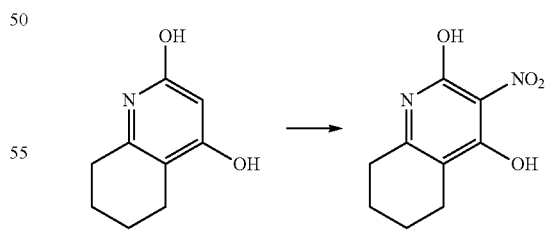

To a 2 L flask was added sulfuric acid (275 ml). The reaction was cooled in an ice bath and 5,6,7,8-tetrahydroquinoline-2,4-diol (65 g, 390 mmol) was added portionwise over 15 minutes. The reaction stirred for an additional 10 minutes. Nitric acid (39.6 ml, 885 mmol) was added portionwise at a rate maintaining the internal reaction temperature below 30° C. The reaction was stirred at RT for an additional 2 hours. The reaction was slowly poured into ice (2 L), the solids filtered and washed with water. The solids were dried under vacuum at 50° C. Yield: 52.2 g, 390 mmol, 63%. ¹H NMR (400 MHz, DMSO-d₆) δ ppm 12.25; (br s, 1 H), 11.75; (br s, 1 H), 2.48; (m, 2 H), 2.34; (m, 2 H), 1.66; (m, 4 H). LCMS m/z 211.2 [M+H].

Step 2: Synthesis of 2,4-dichloro-3-nitro-5,6,7,8-tetrahydroquinoline

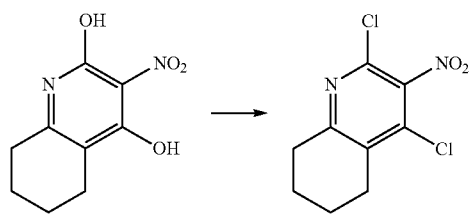 [SMILES: O=[N+]([O-])c1c(O)nc2c(c1O)CCCC2 ; O=[N+]([O-])c1c(Cl)nc2c(c1Cl)CCCC2]

To a 500 ml flask was added 3-nitro-5,6,7,8-tetrahydroquinoline-2,4-diol (13.1 g, 53.0 mmol), dichloroethane (70.0 mL), phosphorous (V) oxychloride (65.1 g, 425 mmol, 40.0 ml). The reaction was heated at 80° C. for 16 hours. The reaction was then cooled to RT and evaporated followed by evaporation from toluene (2×). The residue was filtered through a silica plug with dichloromethane and the eluent was evaporated to provide a brown/orange waxy solid. Yield: 9.2 g, 37.2 mmol, 70%. ¹H NMR (400 MHz, CDCl₃) δ 2.92-3.02; (m, 2H), 2.77-2.85; (m, 2H), 1.85-1.95; (m, 4H). GCMS m/z 246.0. Additional material was prepared using similar conditions.

Step 3: Synthesis of 2-chloro-3-nitro-N-((2,2,5-trimethyl-1,3-dioxan-5-yl)methyl)-5,6,7,8-tetrahydroquinolin-4-amine

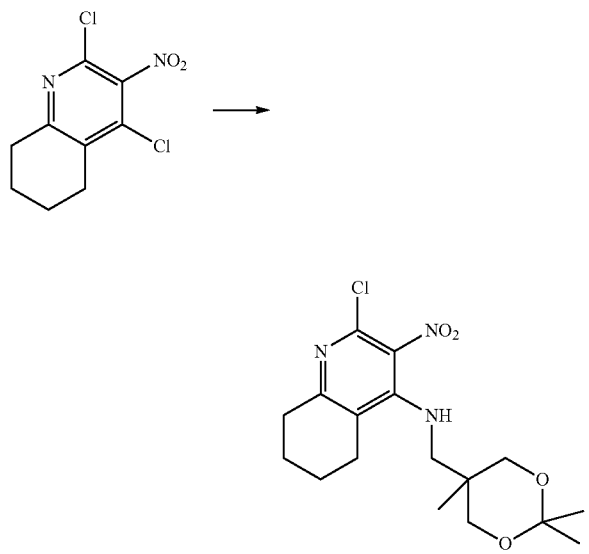 [SMILES: O=[N+]([O-])c1c(Cl)nc2c(c1Cl)CCCC2 ; CC1(CNc2c3c(nc(Cl)c2[N+](=O)[O-])CCCC3)COC(C)(C)OC1]

To 2,4-dichloro-3-nitro-5,6,7,8-tetrahydroquinoline (10.9 g, 44.5 mmol) and dimethylacetamide (55 mL, contains 20% water). Triethylamine (9 g, 89.0 mmol, 12.4 mL) and then (2,2,5-trimethyl-1,3-dioxan-5-yl)methanamine (12.7 g, 80.1 mmol) was added and the reaction was heated at 35° C. for 16 hours. The reaction was cooled to 0° C., water (70 mL) added and reaction stirred for 45 min. The solids were filtered and washed with water to provide title compound as an orange solid. Yield: 14.78 g, 39.96 mmol, 89.8%. ¹H NMR (400 MHz, CDCl₃) δ 5.57; (br. s., 1H), 3.67-3.78; (m, 4H), 3.21; (d, J=4.68 Hz, 2H), 2.83; (t, J=5.66 Hz, 2H), 2.48; (t, J=5.66 Hz, 2H), 1.78-1.92; (m, 4H), 1.47; (d, J=5.85 Hz, 6H), 0.87; (s, 3H). LCMS m/z 370.4 [M+H].

Step 4: Synthesis of N2,N2-bis(4-methoxybenzyl)-3-nitro-N4-((2,2,5-trimethyl-1,3-dioxan-5-yl)methyl)-5,6,7,8-tetrahydroquinoline-2,4-diamine

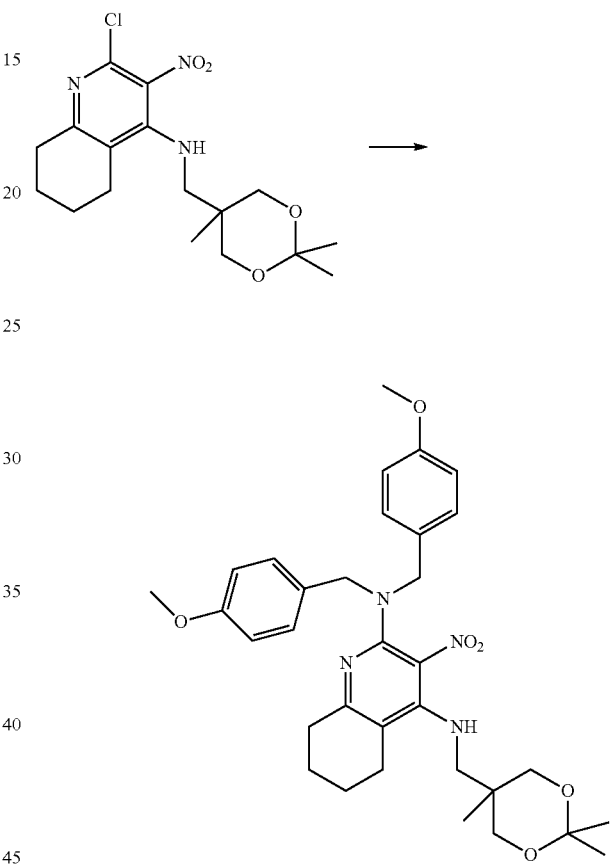

To 2-chloro-3-nitro-N-((2,2,5-trimethyl-1,3-dioxan-5-yl)methyl)-5,6,7,8-tetrahydroquinolin-4-amine (12.98 g, 35.09 mmol) was added Bis(4-methoxybenzyl)amine (27.1 g, 105 mmol) and isopropanol (65 mL). The reaction was refluxed for 51 hours then stirred at RT for 16 hours. The reaction was the diluted dichloromethane (100 mL) and filtered through Celite®. The solids were washed with dichloromethane (50 mL). The organics were concentrated and diluted with ethanol (40 mL) and stirred at RT for 16 hrs. The solids were filtered, and flask washed with ethanol (60 mL). The solids were washed with ethanol (30 mL) and dried under vacuum to provide a yellow solid. Yield: 14.5 g, 24.6 mmol, 70.0%. ¹H NMR (400 MHz, CDCl₃) δ 7.07-7.12; (m, 4H), 6.76-6.84; (m, 4H), 6.39; (t, J=5.66 Hz, 1H), 4.30; (s, 4H), 3.79; (s, 6H), 3.55-3.67; (m, 4H), 3.45; (d, J=5.85 Hz, 2H), 2.73; (t, J=6.44 Hz, 2H), 2.66; (t, J=5.85 Hz, 2H), 1.72-1.86; (m, 4H), 1.44; (s, 3H), 1.41; (s, 3H), 0.82-0.88; (m, 3H). LCMS m/z 591.4 [M+H].

Step 5: N2,N2-bis(4-methoxybenzyl)-N4-((2,2,5-trimethyl-1,3-dioxan-5-yl)methyl)-5,6,7,8-tetrahydroquinoline-2,3,4-triamine

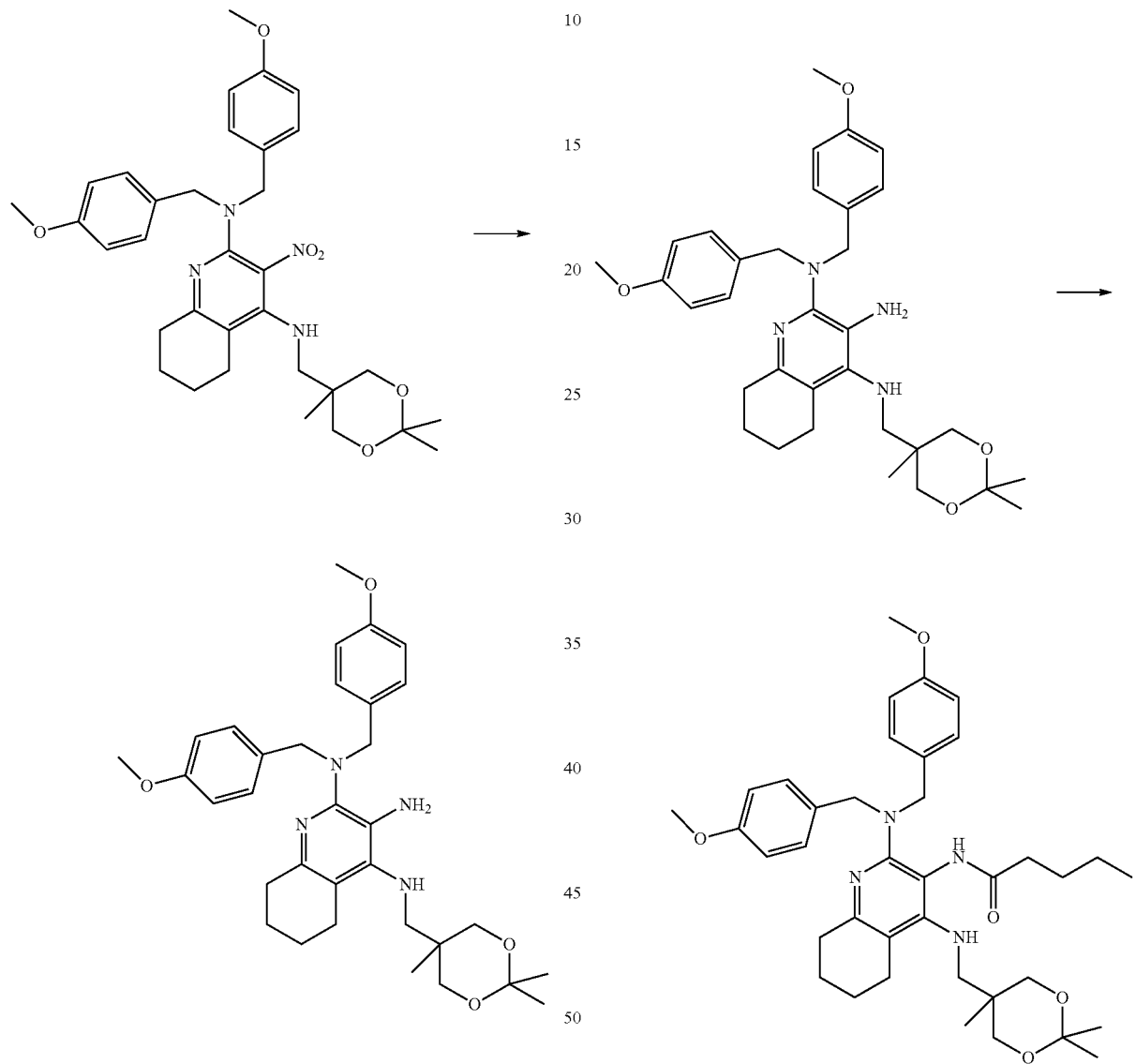

Step 6: Synthesis of N-(2-(bis(4-methoxybenzyl)amino)-4-(((2,2,5-trimethyl-1,3-dioxan-5-yl)methyl)amino)-5,6,7,8-tetrahydroquinolin-3-yl)pentanamide To N2,N2-bis(4-methoxybenzyl)-3-nitro-N4-((2,2,5-trimethyl-1,3-dioxan-5-yl)methyl)-5,6,7,8-tetrahydroquinoline-2,4-diamine (7.2 g, 12.2 mmol) was added methanol (40.6 mL), ammonium formate (3.84 g, 60.9 mmol), and zinc dust (3.99 g, 60.9 mmol). The reaction was stirred for 25 minutes. The reaction was filtered through a pad of Celite® and filtrate concentrated. The residue was dissolved in ethyl acetate, washed with water, brine and the organic was dried over anhydrous sodium sulfate. The reaction was filtered and concentrated to provide title compound. Yield: 6.83 g, 12.19 mmol, 100%. $^1$H NMR (400 MHz, CHLOROFORM-d) δ ppm 7.21; (d, J=8.59 Hz, 4 H), 6.81; (d, J=8.59 Hz, 4 H), 4.15; (s, 4 H), 3.99; (s, 2 H), 3.76-3.83; (m, 8 H), 3.63-3.70; (m, 2 H), 3.21 (br s, 2 H), 2.74; (br t, J=5.66 Hz, 2 H), 2.55; (br t, J=5.46 Hz, 2 H), 1.74-1.87; (m, 4 H), 1.48; (s, 3 H), 1.46; (s, 3 H), 0.93; (s, 3 H) LCMS m/z 561.5 [M+H].

To N2,N2-bis(4-methoxybenzyl)-N4-((2,2,5-trimethyl-1,3-dioxan-5-yl)methyl)-5,6,7,8-tetra-hydroquinoline-2,3,4-triamine (6.84 g, 12.19 mmol) was added dichloromethane (60.9 mL), water (30.5 mL) and sodium bicarbonate (2.56 g, 30.5 mmol). Valeryl chloride (1.62 g, 13.4 mmol, 1.59 mL) was added dropwise over 1 minute and then stirred for 55 minutes. The organic layer was separated and the aqueous washed with dichloromethane. The combined organic layers were washed with brine, dried over anhydrous sodium sulfate, filtered and concentrated to provide title compound which was used without further purification. Yield: 7.86 g, 12.19 mmol. LCMS m/z 645.7 [M+H].

Step 7: Synthesis of 2-butyl-N,N-bis(4-methoxybenzyl)-1-((2,2,5-trimethyl-1,3-dioxan-5-yl)methyl)-6,7,8,9-tetrahydro-1H-imidazo[4,5-c]quinolin-4-amine Step 8: Synthesis of 2-((4-amino-2-butyl-6,7,8,9-tetrahydro-1H-imidazo[4,5-c]quinolin-1-yl)methyl)-2-methylpropane-1,3-diol

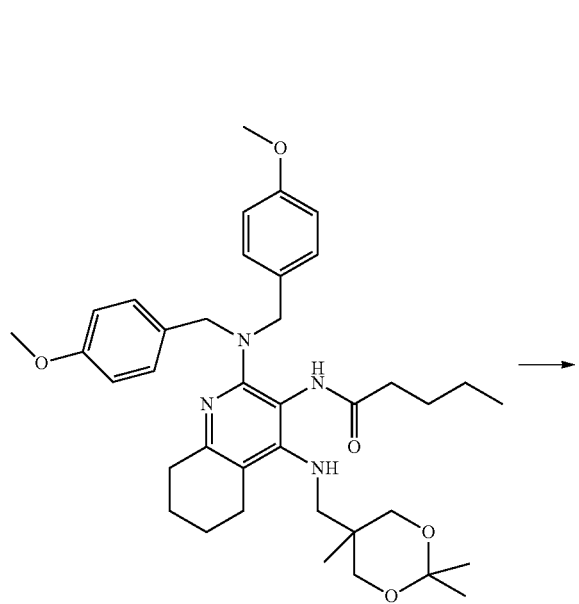

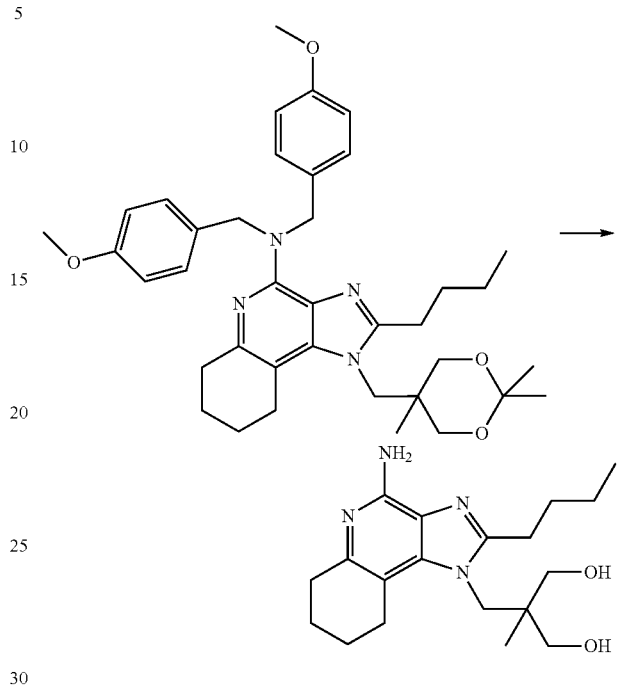

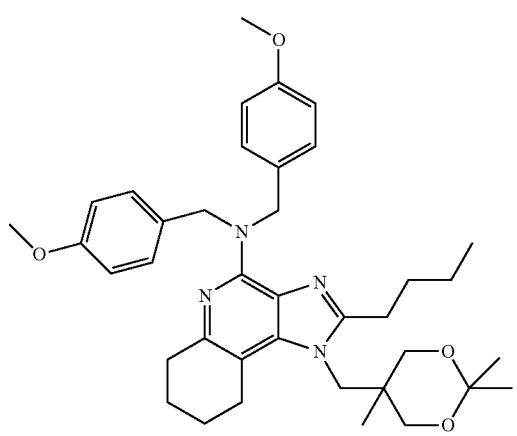

To N-(2-(bis(4-methoxybenzyl)amino)-4-(((2,2,5-trimethyl-1,3-dioxan-5-yl)methyl)amino)-5,6,7,8-tetrahydroquinolin-3-yl)pentanamide (7.86 g, 12.19 mmol) was added ethanol (122 mL) and sodium hydroxide (4.88 g, 60.9 mmol, 3.22 mL, 50% wt solution in water). The reaction was heated at 100 °C. for 48 hours. The reaction was cooled to RT and the solids were filtered, washed with ethanol and dried to provide title compound. Yield: 6.7 g, 10.7 mmol, 87.7%. $^1$H NMR (400 MHz, CHLOROFORM-d) δ ppm 7.26; (d, J=8.59 Hz, 4 H), 6.81; (d, J=8.59 Hz, 4 H), 4.96-5.40; (m, 4 H), 4.39-4.72; (m, 2 H), 3.79; (s, 6 H), 3.41 -3.69; (m, 4 H), 2.63-3.13; (m, 6 H), 1.84; (br s, 4 H), 1.69; (quin, J=7.51 Hz, 2 H), 1.57; (br s, 4 H), 1.46; (s, 6 H), 1.35; (dq, J=14.83, 7.41 Hz, 2 H), 0.89; (t, J=7.41 Hz, 3 H), 0.57; (s, 3 H). LCMS m/z 627.7 [M+H].

To 2-butyl-N,N-bis(4-methoxybenzyl)-1-((2,2,5-trimethyl-1,3-dioxan-5-yl)methyl)-6,7,8,9-tetrahydro-1H-imidazo[4,5-c]quinolin-4- amine (6.70 g, 10.69 mmol) was added toluene (32.4 mL) and concentrated hydrochloric acid (21 mL). The reaction was heated at 60° C. for 3.25 hours. The aqueous layer was washed with toluene, heated to 60° C. and brought to pH 10 with solid potassium carbonate. The reaction was then stirred at 60° C. for 1 hour and 40 minutes followed by cooling to RT. The solids were filtered, rinsed with water and dried under vacuum at 40° C. to provide Example (13). Yield: 2.44 g, 7.04 mmol, 65.9% Yield. $^1$H NMR (400 MHz, DMSO-d$_6$) δ ppm 5.67; (br s, 2 H), 4.78; (br s, 2 H), 4.07-4.45; (m, 2 H), 2.71-3.30; (m, 8 H), 2.66; (br s, 2 H), 1.53-1.93; (m, 6 H), 1.35; (m, J=7.34, 7.34, 7.34, 7.34, 7.34 Hz, 2 H), 0.91; (t, J=7.41 Hz, 3 H), 0.43; (s, 3 H). LCMS m/z 347.3 [M+H].

Example (14): 2-((4-amino-2-butyl-7,8-dihydrocyclopenta[b]imidazo[4,5-d]pyridin-1(6H)-yl)methyl)-2-methylpropane-1,3-diol

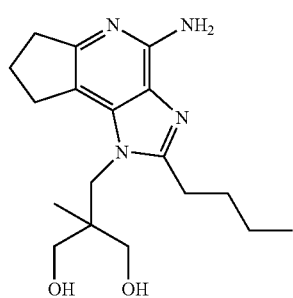 [SMILES: CCCCc1nc2c(N)nc3c(c2n1CC(C)(CO)CO)CCC3]

Prepared in a manner similar to Example 13, starting from 6,7-dihydro-5H-cyclopenta[b]pyridine-2,4-diol. 336 mg prepared (42.5% Yield). Purified by HPLC (Column: Welch Xtimate 75*40 mm*3 um; Mobile phase A: 0.05% NH₄OH in water (v/v); Mobile phase B: Acetonitrile; Gradient: 80% A to 40% A/60% B in 10 min, HOLD at 0% H₂O/100% Acetonitrile for 4 min. Flow: 25 mL/min.). LCMS m/z 333.1 [M+H]⁺. ¹H NMR (400 MHz, DMSO) δ 5.72; (s, 2H), 4.80; (br. s., 2H), 4.14; (s, 2H), 3.25; (br. s., 3H), 2.99-3.34; (m, 3H), 2.88; (br. s., 2H), 2.62-2.78; (m, 2H), 2.02; (apparent quin, J=7.34 Hz, 2H), 1.64-1.75; (m, 2H), 1.35; (apparent qd, J=7.47, 14.74 Hz, 2H), 0.91; (t, J=7.28 Hz, 3H), 0.50; (s, 3H).

Example (15): 2-((4-amino-2-ethyl-1H-imidazo[4,5-c]quinolin-1-yl)methyl)-2-methylpropane-1,3-diol

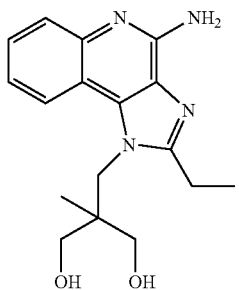 [SMILES: CCc1nc2c(N)nc3ccccc3c2n1CC(C)(CO)CO]

Prepared in a manner similar to 2-((4-amino-2-(ethoxymethyl)-6,7-dimethyl-1H-imidazo[4,5-c]pyridin-1-yl)methyl)-2-methylpropane-1,3- diol, starting from quinoline-2,4-diol. 301 mg prepared. Purified by HPLC (Column: Phenomenex Gemini NX-C18 150*30 mm*5 um; Mobile phase A: 0.05% NH₄OH in water (v/v); Mobile phase B: Acetonitrile; Gradient: 95% A to 55% A/45% B in 7 min, HOLD at 0% H₂O/100% Acetonitrile for 2 min. Flow: 30 mL/min.) ¹H NMR (400 MHz, DMSO-d6) d 8.51; (d, J=8.1 Hz, 1H), 7.58; (d, J=8.3 Hz, 1H), 7.38; (t, J=7.5 Hz, 1H), 7.18; (t, J=7.4 Hz, 1H), 6.43; (s, 2H), 4.98; (br s, 2H), 4.78; (br s, 1H), 4.45; (br s, 1H), 3.19; (br s, 4H), 3.02; (q, J=7.4 Hz, 2H), 1.34; (t, J=7.4 Hz, 3H), 0.55 (s, 3H). LCMS m/z 315.1 [M+H]⁺.

Example (16): 2-((4-amino-2-propyl-1H-imidazo[4,5-c]quinolin-1-yl)methyl)-2-methylpropane-1,3-diol

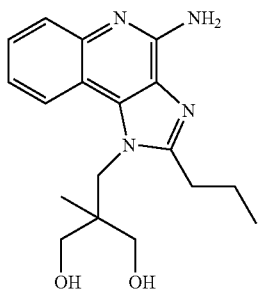 [SMILES: CCCc1nc2c(N)nc3ccccc3c2n1CC(C)(CO)CO]

Prepared in a manner similar to Example 13, starting from quinoline-2,4-diol. 15.8 mg prepared. Purified by HPLC (Column: Waters XBridge C18 19×100, 5 um; Mobile phase A: 0.03% NH₄OH in water (v/v); Mobile phase B: 0.03% NH₄OH Acetonitrile; Gradient: 95% A to 50% A/50% B in 8.5 min, HOLD at 0% H₂O/100% Acetonitrile for 1 min. Flow: 25 mL/min.;). HPLC QC (Column: Waters Atlantis dC18 4.6×50, 5 um; Mobile phase A: 0.05% TFA in water (v/v); Mobile phase B: 0.05% TFA Acetonitrile; Gradient: 95% A to 5% A/95% B in 4.0 min, HOLD at 5% H₂O/95% Acetonitrile for 1 min. Flow: 2 mL/min.; Retention Time: 1.38 min). LCMS m/z 329.5 [M+H]⁺.

Example (17): 2-((4-amino-2-(2-methoxyethyl)-7,8-dihydrocyclopenta[b]imidazo[4,5-d]pyridin-1(6H)-yl)methyl)-2-methylpropane- 1,3-diol

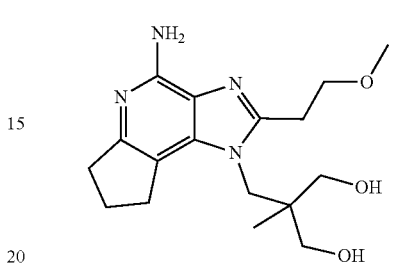

Example 17 was prepared in a manner similar to 2-((4-amino-2-(ethoxymethyl)-6,7-dimethyl-1H-imidazo[4,5-c]pyridin-1-yl)methyl)-2- methylpropane-1,3-diol, starting from 6,7-dihydro-5H-cyclopenta[b]pyridine-2,4-diol. 70 mg prepared. Purified by HPLC (Column: Phenomenex Gemini NX-C18 75*30 mm*3 um; Mobile phase A: 0.05% NH₄OH in water (v/v); Mobile phase B: Acetonitrile; Gradient: 100% A to 70% A/30% B in 7 min, HOLD at 0% H₂O/100% Acetonitrile for 2 min. Flow: 30mL/min.). LCMS m/z 335.1 [M+H]⁺. ¹H NMR (400 MHz, DMSO) δ 5.87; (br. s., 2H), 4.81; (br. s., 2H), 4.17; (br. s., 2H), 3.71; (apparent t, J=6.72 Hz, 2H), 3.30; (br. s., 3H), 3.20-3.28; (m, 4H), 3.23; (s, 3H), 2.68-2.79; (m, 2H), 2.03; (quin, J=7.27 Hz, 2H), 0.50; (s, 3H). 1 proton not observed (obscured).

Example (18): 2-((4-amino-2-(2-methoxyethyl)-6,7,8,9-tetrahydro-1H-imidazo[4,5-c]quinolin-1-yl)methyl)-2-methylpropane-1,3-diol

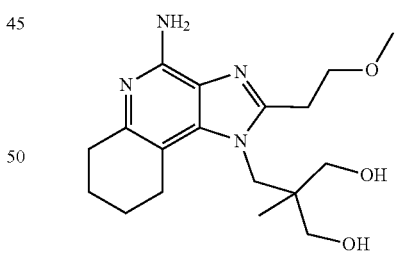

Example (18) was prepared in a manner similar to 2-((4-amino-2-(ethoxymethyl)-6,7-dimethyl-1H-imidazo[4,5-c]pyridin-1-yl)methyl)-2- methylpropane-1,3-diol, starting from 5,6,7,8-tetrahydro-quinoline-2,4-diol. 68 mg prepared. Purified by HPLC (Column: Phenomenex Gemini NX-C18 75*30 mm*3 um; Mobile phase A: 0.05% NH₄OH in water (v/v); Mobile phase B: Acetonitrile; Gradient: 100% A to 60% A/40% B in 7 min, HOLD at 0% H₂O/100% Acetonitrile for 2 min. Flow: 30 mL/min.). ¹H NMR (400 MHz, DMSO-d₆) δ 5.70; (s, 2H), 4.82; (br s, 2H), 4.29; (br s, 2H), 3.69; (br s, 2H), 3.30-2.72; (m, 11H), 2.66; (br s, 2H), 1.74; (br s, 4H), 0.43; (s,3H). LCMS m/z 349.2 [M+H]⁺.

Example (19): 2-((4-amino-2-(2-methoxyethyl)-1H-imidazo[4,5-c]quinolin-1-yl)methyl)-2-methylpropane-1,3-diol

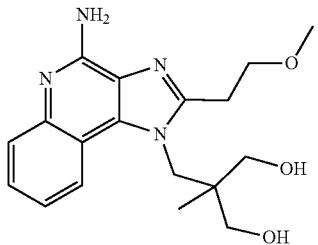 [SMILES: COCCc1nc2c(N)nc3ccccc3c2n1CC(C)(CO)CO]

Example (19) was prepared in a manner similar to 2-((4-amino-2-(ethoxymethyl)-6,7-dimethyl-1H-imidazo[4,5-c]pyridin-1-yl)methyl)-2-methylpropane-1,3-diol, starting from quinoline-2,4-diol. 108 mg prepared. Purified by HPLC (Column: Phenomenex Gemini NX-C18 75*30 mm*3 um; Mobile phase A: 0.05% $NH_4OH$ in water (v/v); Mobile phase B: Acetonitrile; Gradient: 97% A to 57% A/43% B in 7 min, HOLD at 0% $H_2O$/100% Acetonitrile for 2 min. Flow: 25 mL/min.;) LCMS m/z 345.3 [M+H]$^+$. $^1$H NMR (400 MHz, DMSO-$d_6$) δ=8.52; (d, J=8.3 Hz, 1H), 7.58; (dd, J=1.1, 8.3 Hz, 1H), 7.43-7.34; (m, 1H), 7.23-7.14; (m, 1H), 6.45; (s, 2H), 5.00; (t, J=4.8 Hz, 2H), 4.76; (br s, 1H), 4.53; (br s, 1H), 3.79; (br s, 2H), 3.43; (br d, J=5.8 Hz, 3H), 3.30-3.24; (m, 4H), 3.19; (br s, 2H), 0.55; (s, 3H).

Biological Testing

The Examples described were tested for biological activity in functional cellular assays using HEK293 cells stably overexpressing human TLR7 or TLR8. The assays tested for the ability of each Example to stimulate secretion of interferon alpha (IFNα) in human primary blood mono nuclear cells (PBMC).

hTLR7 and hTLR8 Cell Functional Assays

To determine the ability of each Example to activate the human toll like receptor 7 (hTLR7) or human toll like receptor 8 (hTLR8), cell-based reporter systems were utilized. HEK293 cells stably overexpressing either hTLR7 or hTLR8 along with a reporter gene containing an optimized secreted embryonic alkaline phosphatase gene (SEAP), under the control of the IFN-b minimal promoter fused to five NF-κB and AP-1-binding sites, were obtained from Invivogen (HEK-Blue™ hTLR7, cat #Hkb-ht1r7; HEK-Blue™ hTLR8, cat #Hkb-ht1r8). Stimulation of hTLR7 or hTLR8 in these cells activates NF-κB and AP-1 and induces the production of SEAP which can be quantified using an alkaline phosphatase detection reagent.

Cells were maintained in Dulbecco's Modified Eagle Media (DMEM) (containing Fetal Bovine Serum (FBS) heat inactivated (10%), Glutamax (2 mM), Penicillin/Streptomycin, Blasticidin (10 μg/ml), Zeocin (100 μg/ml) and Normocin (100 μg/ml)). On day one of the assay, Examples were prepared using 11-point half-log serial dilutions from a 10mM DMSO stock solution and 50 nl was spotted into 384-well Viewplates (PerkinElmer, cat #6007480). Positive control TLR7/8 agonist and negative control (DMSO, no Example) were also spotted within the assay plate and were used to determine percent effect during the analysis process.

After resuspension in DMEM assay media containing FBS heat inactivated (10%), Glutamax (2 mM) and Penicillin/Streptomycin, 10,000 cells/20 μl/well were added to previously prepared plates. Plates were incubated overnight (16-20 hrs) at 37° C. in a 5% $CO_2$ environment. Prewetted Microclime lids (Labcyte, LLS-0310) were used to prevent evaporation. On day two of the assay, QUANTI-Blue™ detection reagent was prepared by reconstituting QUANTI-Blue™ powder (InvivoGen, Rep-qb1) with 100 ml of sterile water and allowed to equilibrate to 37° C. for 15 minutes. 20 μl of QUANTI-Blue™ detection reagent was added to each well and plates were incubated at room temperature for 180 min. At the end of the incubation, plates were read on an Envision (Perkin Elmer) plate reader capturing absorbance at 650 nm.

Using Positive (TLR7/8 agonist) and Negative (DMSO) controls, the percent (%) effect was calculated for each Example using the following equation:

effect=100−[100*{(Example−Positive Control)/(Negative Control−Positive Control)}]

The % effect at each concentration of each Example was calculated utilizing the ABase software suite (IBDS) and was relative to the amount of SEAP produced in the positive and negative control wells contained within each assay plate. The concentrations and % effect values for each Example were fit using a 4-parameter logistic model in ABase and the concentration of each Example that produced 50% response ($EC_{50}$) was calculated.

INFα Assay from Peripheral Blood Mononuclear Cells (PBMC)

To determine the ability of each Example to induce the release of interferon alpha (IFNα) from freshly isolated peripheral blood mononuclear cells (PBMCs), a Homogeneous Time-Resolved Fluorescence (HTRF) assay was utilized. Human whole blood was collected from healthy donors via vein puncture in accordance with Pfizer protocols (Protocol No. GOHW RDP-01), approved by the Shulman Institutional Review Board. 50 ml of human venous blood sample from individual donors was heparinized by addition to a conical tube containing 714 units of Heparin Sodium Injection MDV (Fresenius Kabi, cat #70041) followed by gentle inversion of the tube several times. Blood was then transferred to a flask, the conical tube was rinsed with 40 ml of PBS containing 2 mM EDTA (PBS-EDTA), and the rinse was added to the blood flask with gently mixing. 30 ml of the diluted blood was added to 3 separate histopaque tubes (Sigma, cat #A0561), applying directly to the frit. Histopaque tubes were then spun for 15 min at 1000×g in a tabletop centrifuge. Following density separation, excess upper phase of plasma was aspirated to within ~5 ml above the interphase and remaining plasma along with the cloudy interphase containing PBMCs were gently decanted into a new conical tube. 15 ml of PBS-EDTA was added to the histopaque tube and swirled gently to remove remaining PBMCs that adhered to the tube wall and this wash was added to the existing PBMCs in the tube. The volume of the tube was brought to 40 ml with PBS-EDTA and tubes were spun at 250×g for 12 minutes at room temperature. After aspiration of the supernatant, the pellet was gently resuspended with 10 ml of PBS-EDTA and centrifuged again at 250×g for 12 minutes. The resulting supernatant was decanted, and the pellet was resuspended in 20 ml of ACK lysing buffer (ThermoFisher, cat #A10492-01) followed by incubation at room temperature for 5 minutes. The volume of each tube was brought to 50 ml with the addition of PBS-EDTA and tubes were spun at 177×g for 12 minutes at room temperature. The PBMC pellet was again resuspended in 10 ml of PBS without EDTA and tubes were spun for a final time at 177×g for 10 minutes. The supernatant was decanted and PBMCs were resuspended in Assay Media (RPMI base media with 10% FBS heat inactivated, 2 mM Glutamax and Penicillin/Streptomycin).

Each Example was prepared for the assay using 11-point half log serial dilutions from a 2.5 mM DMSO stock solution and 400 nl was spotted into 384 well Viewplate (Perkin Elmer, cat #6007480). Positive and negative controls (previously described) were also spotted within the assay plate and were used to determine percent effect during the analysis process. PBMCs were counted and plated at a density of 100,000 cells/100pl/well; plates were covered with a prewet microclime lid to prevent evaporation and incubated for 24 hrs at 37° C. in a 5% $CO_2$ atmosphere. At the end of the incubation, the microclime lid was removed and the plates were spun at 1000 rpm for 5 minutes. 16 µl of conditioned media from the cell plate was transferred into a separate 384 well low-volume plate (Greiner One, 784080). IFNα levels were quantitated using an HTRF® kit (Cisbio, cat #62HIFNAPEG) according to the manufacturer's instructions. The kit supplies two different specific antibodies, one labelled with D2 (acceptor) and the other labelled with cryptate (donor), and detection buffer. The antibody stocks were diluted 1:20 in detection buffer. For one 384 well plate, 62.5 µl of D2 antibody stock and 62.5 µl of cryptate antibody stock was added to 2.375 ml of detection buffer and mixed well. 4 µl of the antibody mix was added to each well containing the conditioned media obtained from the corresponding well of the Viewplate. The low-volume plates were sealed and incubated for 24 hours at room temperature. The HTRF signal was read with an Envision multi-label plate reader (Perkin Elmer) using excitation of 330 nm and emissions of 615 nm and 665 nm. Results were calculated as (665 nm/615 nM ratio)*10,000 and raw data was converted to concentration of IFNα (pg/ml) using the cytokine standard curve. As discussed above, Positive (TLR7/8 agonist) and Negative (DMSO) controls were used to calculate the percent (%) effect for each Example using the following equation:

% effect=100−[100*{(Example−Positive Control)/ (Negative Control−Positive Control)}]

The % effect at each concentration for each Example was calculated utilizing the ABase software suite (IBDS) and was relative to the amount of IFNα produced in the positive and negative control wells contained within each assay plate. The concentrations and % effect values for each Example were fit using a 4-parameter logistic model in ABase and the concentration of Example that produced 50% response ($EC_{50}$) was calculated and provided in Table 1, as the geometric mean $EC_{50}$ when an Example was tested more than once. A blank cell in Table 1 indicates no data was obtained for that Example in that specific assay.

TABLE 1

| Example number | hTLR7 (cell) $EC_{50}$ (µM) | hTLR8 (cell) $EC_{50}$ (µM) | IFNα (PBMC) $EC_{50}$ (µM) |
|---|---|---|---|
| 1 | 0.644 | 2.549 | 0.099 |
| 2 | 0.054 | 0.811 | 0.019 |
| 3 | 0.029 | 0.194 | 0.007 |
| 4 | 0.054 | 0.400 | |
| 5 | 0.042 | 0.273 | |
| 6 | 0.049 | 6.398 | 0.022 |
| 7 | 0.103 | 16.472 | 0.198 |
| 8 | 0.078 | 8.018 | 0.048 |
| 9 | 0.027 | 1.443 | 0.002 |
| 10 | 0.004 | 0.092 | 0.001 |
| 11 | 0.013 | 0.160 | |
| 12 | 0.009 | 0.191 | |
| 13 | 0.009 | 0.104 | 0.0004 |
| 14 | 0.014 | 0.247 | 0.007 |
| 15 | 0.075 | 0.613 | 0.012 |
| 16 | 0.019 | 0.325 | 0.011 |
| 17 | 0.156 | 1.064 | |
| 18 | 0.016 | 0.119 | |
| 19 | 0.009 | 0.310 | |

All publications and patent applications cited in the specification are herein incorporated by reference in their entirety. It will be apparent to those of ordinary skill in the art that certain changes and modifications may be made thereto without departing from the spirit or scope of the appended claims.

The invention claimed is:

1. A method for the treatment of cancer in a subject in need thereof, comprising administering to the subject a therapeutically effective amount of a compound selected from the group consisting of:
2-((4-amino-2-(ethoxymethyl)-6,7-dimethyl-1H-imidazo[4,5-c]pyridin-1-yl)methyl)-2-methylpropane-1,3-diol;
2-((4-amino-2-(ethoxymethyl)-1H-imidazo[4,5-c]quinolin-1-yl)methyl)-2-methylpropane-1,3-diol;
2-((4-amino-2-(ethoxymethyl)-7,8-dihydrocyclopenta[b]imidazo[4,5-d]pyridin-1(6H)-yl)methyl)-2-methylpropane-1,3-diol;
2-((4-amino-2-(ethoxymethyl)-6,7,8,9-tetrahydro-1H-imidazo[4,5-c]quinolin-1-yl)methyl)-2-methylpropane-1,3-diol;
3-(4-amino-2-(ethoxymethyl)-6,7-dimethyl-1H-imidazo[4,5-c]pyridin-1-yl)-2-(methoxymethyl)-2-methylpropan-1-ol;
(R)-3-(4-amino-2-(ethoxymethyl)-6,7-dimethyl-1H-imidazo[4,5-c]pyridin-1-yl)-2-(methoxymethyl)-2-methylpropan-1-ol;
(S)-3-(4-amino-2-(ethoxymethyl)-6,7-dimethyl-1H-imidazo[4,5-c]pyridin-1-yl)-2-(methoxymethyl)-2-methylpropan-1-ol;
2-((4-amino-6,7-dimethyl-2-(2,2,2-trifluoroethyl)-1H-imidazo[4,5-c]pyridin-1-yl)methyl)-2-methylpropane-1,3-diol;
2-((4-amino-2-(ethoxymethyl)-6,7-dimethyl-1H-imidazo[4,5-c]pyridin-1-yl)methyl)-2-ethylpropane-1,3-diol;
2-((4-amino-2-butyl-1H-imidazo[4,5-c]quinolin-1-yl)methyl)-2-methylpropane-1,3-diol;
2-((4-amino-2-butyl-6,7-dimethyl-1H-imidazo[4,5-c]pyridin-1-yl)methyl)-2-methylpropane-1,3-diol; and
2-((4-amino-2-pentyl-1H-imidazo[4,5-c]quinolin-1-yl)methyl)-2-methylpropane-1,3-diol;
or a pharmaceutically acceptable salt thereof,
wherein the cancer is basal cell carcinomas, ovarian cancer, melanoma, non-muscular invasive bladder cancer, breast cancer, or head and neck cancer.

2. The method of claim 1, wherein the cancer is non-muscular invasive bladder cancer.

3. The method of claim 1, wherein the compound is 2-((4-amino-2-(ethoxymethyl)-6,7-dimethyl-1H-imidazo[4, 5-c]pyridin-1-yl)methyl)-2-methylpropane-1,3-diol, or a pharmaceutically acceptable salt thereof.

4. The method of claim 3, wherein the cancer is non-muscular invasive bladder cancer.

5. The method of claim 1, wherein the compound is 2-((4-amino-2-(ethoxymethyl)-6,7-dimethyl-1H-imidazo[4,5-c]pyridin-1-yl)methyl)-2-methylpropane-1,3-diol.

6. The method of claim 5, wherein the cancer is non-muscular invasive bladder cancer.

7. The method of claim 1, wherein the compound is administered with at least one additional therapeutic agent.

8. A method for the treatment of cancer in a subject in need thereof, comprising administering to the subject a therapeutically effective amount of a compound selected from the group consisting of:
2-((4-amino-2-butyl-6,7,8,9-tetrahydro-1H-imidazo[4,5-c]quinolin-1-yl)methyl)-2-methylpropane-1,3-diol;
2-((4-amino-2-butyl-7,8-dihydrocyclopenta[b]imidazo[4,5-d]pyridin-1(6H)-yl)methyl)-2-methylpropane-1,3-diol;
2-((4-amino-2-ethyl-1H-imidazo[4,5-c]quinolin-1-yl)methyl)-2-methylpropane-1,3-diol; and
2-((4-amino-2-propyl-1H-imidazo[4,5-c]quinolin-1-yl)methyl)-2-methylpropane-1,3-diol;

or a pharmaceutically acceptable salt thereof,
wherein the cancer is basal cell carcinomas, ovarian cancer, melanoma, non-muscular invasive bladder cancer, breast cancer, or head and neck cancer.

9. The method of claim 8, wherein the cancer is non-muscular invasive bladder cancer.

10. The method of claim 8, wherein the compound is administered with at least one additional therapeutic agent.

11. The method of claim 1, wherein the compound is 2-((4-amino-2-(ethoxymethyl)-1H-imidazo[4,5-c]quinolin-1-yl)methyl)-2-methylpropane-1,3-diol, or a pharmaceutically acceptable salt thereof.

12. The method of claim 1, wherein the compound is 2-((4-amino-2-(ethoxymethyl)-1H-imidazo[4,5-c]quinolin-1-yl)methyl)-2-methylpropane-1,3-diol.

13. The method of claim 1, wherein the compound is 2-((4-amino-2-butyl-1H-imidazo[4,5-c]quinolin-1-yl)methyl)-2-methylpropane-1,3-diol, or a pharmaceutically acceptable salt thereof.

14. The method of claim 1, wherein the compound is 2-((4-amino-2-butyl-1H-imidazo[4,5-c]quinolin-1-yl)methyl)-2-methylpropane-1,3-diol.

* * * * *